(12) United States Patent
Nelson et al.

(10) Patent No.: US 9,404,147 B2
(45) Date of Patent: Aug. 2, 2016

(54) CLOSED NUCLEIC ACID STRUCTURES

(71) Applicant: Gen-Probe Incorporated, San Diego, CA (US)

(72) Inventors: Norman C. Nelson, San Diego, CA (US); Jijumon Chelliserry, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 240 days.

(21) Appl. No.: 13/720,108

(22) Filed: Dec. 19, 2012

(65) Prior Publication Data

US 2013/0203123 A1 Aug. 8, 2013

Related U.S. Application Data

(60) Provisional application No. 61/577,648, filed on Dec. 19, 2011.

(51) Int. Cl.
*C07H 21/00* (2006.01)
*C12Q 1/68* (2006.01)

(52) U.S. Cl.
CPC .............. *C12Q 1/6811* (2013.01); *C07H 21/00* (2013.01); *C12Q 1/6844* (2013.01); *C12Q 1/6848* (2013.01)

(58) Field of Classification Search
CPC ...................................................... C07H 21/00
USPC ........................................................ 536/25.3
See application file for complete search history.

(56) References Cited

U.S. PATENT DOCUMENTS

| | | | |
|---|---|---|---|
| 6,235,502 B1 | 5/2001 | Weissman et al. |
| 6,828,098 B2 | 12/2004 | Langmore et al. |
| 7,575,860 B2 | 8/2009 | Evans et al. |
| 8,501,405 B2 | 8/2013 | Korlach et al. |
| 2009/0181861 A1 | 7/2009 | Li et al. |
| 2009/0280538 A1 | 11/2009 | Patel et al. |
| 2013/0203123 A1 | 8/2013 | Nelson et al. |
| 2014/0329282 A1 | 11/2014 | Nelson et al. |

FOREIGN PATENT DOCUMENTS

| | | |
|---|---|---|
| EP | 1741787 A1 | 1/2007 |
| WO | 9317127 A1 | 9/1993 |
| WO | 02103054 A1 | 12/2002 |
| WO | 2005056750 A2 | 6/2005 |
| WO | 2009120372 A2 | 10/2009 |
| WO | 2010003153 A2 | 1/2010 |
| WO | 2010086622 A1 | 8/2010 |
| WO | 2013036685 A1 | 9/2012 |
| WO | 2013036668 A1 | 3/2013 |

OTHER PUBLICATIONS

Drmanac et al., "Human Genome Sequencing Using Unchained Base Reads on Self-Assembling DNA Nanoarrays," Science, Jan. 1, 2010, vol. 327, pp. 78-81, American Association for the Advancement of Science, Washington, DC, US.
Drmanac et al., "Supporting Online Material for Human Genome Sequencing Using Unchained Base Reads on Self-Assembling DNA Nanoarrays," Science, Jan. 1, 2010, vol. 327, pp. 78-81, American Association for the Advancement of Science, Washington, DC, US.
Patent Examination Report, Australian Patent Application No. 2012304520, issued Dec. 12, 2014.
Patent Examination Report, Australian Patent Application No. 2013304537, issued Jan. 9, 2015.
Travers et al., "A flexible and efficient template format for circular consensus sequencing and SNP detection," Nucleic Acids Research, published online Jun. 22, 2010, vol. 38, No. 15, Oxford University Press, doi:10.1093/nar/gkq543.
Ho et al. "Structure and Mechanism of RNA Ligase", Structure, Feb. 2004, pp. 327-339, vol. 12, Elsevier Science Ltd.
Silber et al., "Purification and Properties of Bacteriophage T4-Induced RNA Ligase", Proc. Nat. Acad. Sci., Oct. 1972, pp. 3009-3013, vol. 69, No. 10, USA.
Chen et al., "Recognition of an expanded genetic alphabet by type-II restriction endonucleases and their application to analyze polymerase fidelity", Nucleic Acids Research, 2011, pp. 3949-3961, vol. 39, No. 9, Oxford University Press.

*Primary Examiner* — Ardin Marschel
(74) *Attorney, Agent, or Firm* — Jeffrey E. Landes; Joe Liebeschuetz

(57) ABSTRACT

The invention provides compositions and methods for making closed nucleic acid structures in which one or both strands are continuous. The closed nucleic acid structures can be used as sequencing templates among other applications.

6 Claims, 23 Drawing Sheets dU stem-loop primer

SEQUENCE LISTING

```
<160> NUMBER OF SEQ ID NOS: 14

<210> SEQ ID NO 1
<211> LENGTH: 6
<212> TYPE: DNA
<213> ORGANISM: Artificial Sequence
<220> FEATURE:
<223> OTHER INFORMATION: Synthesized

<400> SEQUENCE: 1 gcgccg                                                              6

<210> SEQ ID NO 2
<211> LENGTH: 6
<212> TYPE: DNA
<213> ORGANISM: Artificial Sequence
<220> FEATURE:
<223> OTHER INFORMATION: Synthesized

<400> SEQUENCE: 2 cggcgc                                                              6

<210> SEQ ID NO 3
<211> LENGTH: 24
<212> TYPE: DNA
<213> ORGANISM: Artificial Sequence
<220> FEATURE:
<223> OTHER INFORMATION: Synthesized

<400> SEQUENCE: 3
gggccgtttc ccggtcttaa aaaa                                         24

<210> SEQ ID NO 4
<211> LENGTH: 24
```

```
<212> TYPE: DNA
<213> ORGANISM: Artificial Sequence
<220> FEATURE:
<223> OTHER INFORMATION: Synthesized

<400> SEQUENCE: 4
tggttgtgtc cgcatctgaa aaaa                                    24

<210> SEQ ID NO 5
<211> LENGTH: 63
<212> TYPE: DNA
<213> ORGANISM: Artificial Sequence
<220> FEATURE:
<223> OTHER INFORMATION: Synthesized

<400> SEQUENCE: 5
aagaccggga aacggcccat ctctctcttt tcctcctcct ccgttgttgt tgttgagaga    60
gat                                                                63

<210> SEQ ID NO 6
<211> LENGTH: 63
<212> TYPE: DNA
<213> ORGANISM: Artificial Sequence
<220> FEATURE:
<223> OTHER INFORMATION: Synthesized

<400> SEQUENCE: 6
cagatgcgga cacaaccaat ctctctcttt tcctcctcct ccgttgttgt tgttgagaga    60
gat                                                                63

<210> SEQ ID NO 7
<211> LENGTH: 17
<212> TYPE: DNA
<213> ORGANISM: Artificial Sequence
<220> FEATURE:
<223> OTHER INFORMATION: Synthesized

<400> SEQUENCE: 7
gtaaaacgac ggccagt                                            17

<210> SEQ ID NO 8
<211> LENGTH: 19
<212> TYPE: DNA
<213> ORGANISM: Artificial Sequence
<220> FEATURE:
<223> OTHER INFORMATION: Synthesized

<400> SEQUENCE: 8
ggaaacagct atgaccatg                                          19

<210> SEQ ID NO 9
<211> LENGTH: 24
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 24
<223> OTHER INFORMATION: C = reverse polarity nucleotide

<400> SEQUENCE: 9
taatccgtaa aacgacggcc agtc                                    24

<210> SEQ ID NO 10
```

```
<211> LENGTH: 26
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 26
<223> OTHER INFORMATION: C = reverse polarity nucleotide

<400> SEQUENCE: 10
taatccggaa acagctatga ccatgc                                              26

<210> SEQ ID NO 11
<211> LENGTH: 49
<212> TYPE: DNA
<213> ORGANISM: Artificial Sequence
<220> FEATURE:
<223> OTHER INFORMATION: Synthesized

<400> SEQUENCE: 11
tctctctctt ttcctcctcc tccgttgttg ttgttgagag agataatcc                     49

<210> SEQ ID NO 12
<211> LENGTH: 6
<212> TYPE: DNA
<213> ORGANISM: Artificial Sequence
<220> FEATURE:
<223> OTHER INFORMATION: Synthesized

<400> SEQUENCE: 12 taatcc                                                                     6

<210> SEQ ID NO 13
<211> LENGTH: 10
<212> TYPE: DNA
<213> ORGANISM: Artificial Sequence
<220> FEATURE:
<223> OTHER INFORMATION: Synthesized

<400> SEQUENCE: 13
ttcgcggcaa                                                                10

<210> SEQ ID NO 14
<211> LENGTH: 10
<212> TYPE: DNA
<213> ORGANISM: Artificial Sequence
<220> FEATURE:
<223> OTHER INFORMATION: Synthesized

<400> SEQUENCE: 14
ttgccgcgaa                                                                10
```

CLOSED NUCLEIC ACID STRUCTURES

CROSS-REFERENCE TO RELATED APPLICATIONS

The present application is a non-provisional of and claims the benefit of U.S. Provisional Application No. 61/577,648, filed Dec. 19, 2011, incorporated by reference in its entirety for all purposes.

REFERENCE TO A SEQUENCE LISTING

This application includes an electronic sequence listing in a file named 427766_SEQLST.TXT, created May 23, 2016, and containing 2,702 bytes, which is hereby incorporated by reference in its entirety for all purposes.

BACKGROUND

Closed nucleic acid structures are useful for a number of techniques, including sequencing and amplification methods. Closed nucleic acid structures have also been used as detection probes in various diagnostic methods. Formation of such structures can be complex and time-consuming. Synthesis of such structures is often associated with low efficiency, side product formation, chimeric product formation and low yields. One type of closed nucleic acid structure is formed by ligating hairpin loop adapters to the ends of a double-stranded target nucleic acid as in the Pacific Biosciences' SMRTbell™ template. Such a template is used to give alternating reads of both target strands interspersed by the adapters in a next-generation sequencing method. Other closed nucleic acid structures include closed stem-loops or pad-locks. There is a need for improved methods for generating closed nucleic acid structures, wherein the improvements include simpler, more rapid and more efficient methods for generating these structures, methods that provide a high yield of useful template, methods that reduce side product formation, and methods that reduce chimeric product formation.

BRIEF DESCRIPTION OF THE FIGURES

In FIG. 15A, a pair of primers having sequence tags is used to generate an amplified nucleic acid having defined ends, either strand of which can be ligated with a stem-loop adaptor to generate a closed nucleic acid structure. FIG. 15B depicts use of blocking oligonucleotides to facilitate formation of the closed nucleic acid structure. FIG. 15C depicts a variation on the method shown in FIG. 15A in which the amplification primers do not include sequence tags and two stem-loop adaptors instead of one are used in the subsequent steps. FIGS. 15D and 15E depict variations on the method shown in FIG. 15C in which there is an additional step of primer extension. The primer used in the extension step can hybridize to a strand of amplified nucleic acid having defined ends, at a position upstream of the 3' end of the strand, as depicted in FIG. 15F, FIGS. 15G and 15H depict variations of the method shown in FIGS. 15E and 15D, respectively, in which there is no amplification step and the template is single-stranded nucleic acid that has undefined ends.

In FIG. 20A, the 3' blocked oligonucleotides include deoxyribo-uracil nucleobase units.

SUMMARY OF THE CLAIMED INVENTION

Figure 1:
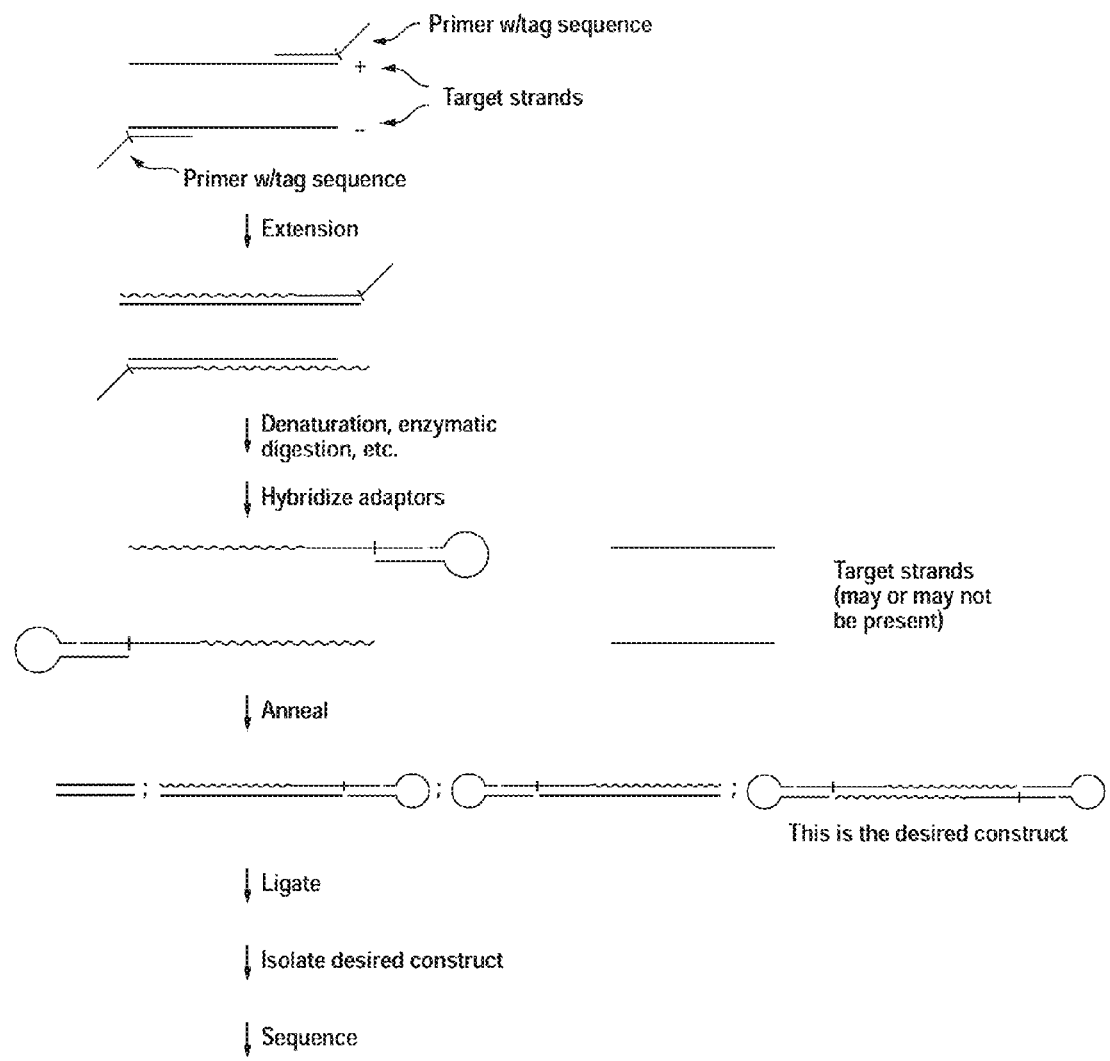
FIG. 1 illustrates an exemplary form of method 1 for generating a closed nucleic acid structure using a pair of primers and a pair of corresponding adaptors.

In one aspect, the invention provides methods of forming a closed nucleic acid structure from a target nucleic acid, comprising: (a) denaturing a target nucleic acid; (b) annealing a primer pair to opposing strands of the denatured target nucleic acid, each of the primers having a 5' phosphate group, each of the primers having a 3' segment and a 5' segment, the 3' segments of the primers being target-binding segments; (c) extending the primers with a nucleic acid polymerase to obtain primer-extended target nucleic acids, some of which have a strand with an overhanging 5' segment from the first primer and others of which have an opposing strand with an overhanging 5' segment from the second primer; (d) denaturing the primer-extended target nucleic acids; (e) annealing a first adaptor and a second adaptor, both having a 5' region and a 3' region, to the denatured primer-extended target nucleic acids to form an adaptor-capped nucleic acid having one strand comprising the 5' segment from the first primer and an opposing strand comprising the 5' segment from the second primer, and adaptors annealed to the 5' segments of the primers at both ends of the adaptor-capped nucleic acid; wherein the 3' region of the adaptor comprises a stem-loop structure, the 5' region of the adaptor having a 5' phosphate group, and the 5' region of the first adaptor is complementary to the 5' segment of the first primer and the 5' region of the second adaptor is complementary to the 5' segment of the second primer; and (f) contacting the adaptor-capped nucleic acid with a ligase which seals a nick in the adaptor-capped nucleic acid, thereby forming a closed nucleic acid structure.

In another aspect, the invention provides methods of forming a closed nucleic acid structure from target nucleic acid, comprising: (a) denaturing a target nucleic acid; (b) annealing a primer pair to opposing strands of the denatured target nucleic acid, each of the primers having a 3' segment and a 5' segment, the 3' segments of the primers being target-binding segments, the 5' segments being complementary in opposing orientations, a first of the primers having a 5' phosphate group and the second of the primers lacking a 5' phosphate and/or having a shorter 5' segment than the first primer; (c) extending the primers with a nucleic acid polymerase to obtain primer-extended target nucleic acids, some of which have a strand with an overhanging 5' segment from the first primer and others of which have an opposing strand with an overhanging 5' segment from the second primer; (d) denaturing the primer-extended target nucleic acids; (e) annealing strands of the denatured primer-extended target nucleic acids having overhanging 5' segments, wherein strands and opposing strands anneal to one another and circularize by annealing of the 5' segments thereby forming a closed nucleic acid structure; and (f) contacting the closed nucleic acid structure with a ligase which seals a nick between the 5' phosphate group of the first primer and an adjacent 3' hydroxyl group leaving the closed nucleic acid structure with a single nick or gap between the 5' segment of the second primer and a 3' hydroxyl of an adjacent nucleotide.

In another aspect, the invention provides methods of forming a closed nucleic acid structure from a target nucleic acid, comprising: (a) contacting a target nucleic acid with a primer pair under amplification conditions, each of the primers having a 5' phosphate group, each of the primers having a 3' segment and a 5' segment, the 3' segments of the primers being target-binding segments; the first 3'→5' nucleobase unit in the 5' segment is an extension blocker; wherein the extension blocker blocks nucleobase unit extension by a nucleic acid polymerase when the 5' segment serves as a template for nucleobase unit extension; thereby forming an amplified target nucleic acid having a strand comprising an overhanging 5' segment from the first primer and an opposing strand comprising an overhanging 5' segment from the second primer; (b) annealing a first adaptor and a second adaptor, both having a 5' region and a 3' region, to the amplified target nucleic acids to form an adaptor-capped nucleic acid, wherein the 3' region of the adaptor comprises a stem-loop structure, the 5' region of the adaptor having a 5' phosphate group, and the 5' region of the first adaptor is complementary to the 5' segment of the first primer and the 5' region of the second adaptor is complementary to the 5' segment of the second primer; and (c) contacting the adaptor-capped nucleic acid with a ligase which seals a nick in the adaptor-capped nucleic acid thereby forming a closed nucleic acid structure.

In another aspect, the invention provides methods of forming a closed nucleic acid structure from a target nucleic acid, comprising: (a) contacting a target nucleic acid with a primer pair under amplification conditions, each of the primers having a 3' segment and a 5' segment, the 3' segments of the primers being target-binding segments, the 5' segments being complementary in opposing orientations, a first of the primers having a 5' phosphate group and the second of the primers lacking a 5' phosphate and/or having a shorter 5' segment than the first primer; the first 3'→5' nucleobase unit in the 5' segment is an extension blocker; wherein the extension blocker blocks nucleobase unit extension by a nucleic acid polymerase when the 5' segment serves as a template for nucleobase unit extension, thereby forming an amplified target nucleic acids having a strand comprising an overhanging 5' segment from the first primer and an opposing strand comprising an overhanging 5' segment from the second primer; (b) annealing an overhanging 5' segment from the first primer of one strand of the amplified target nucleic acid and an overhanging 5' segment from the second primer of the opposing strand of the same amplified target nucleic acid thereby forming an annealed target nucleic acid; and (c) contacting the annealed target nucleic acid with a ligase which seals a nick between the 5' phosphate group of the first primer and an adjacent 3' hydroxyl group leaving the closed nucleic acid structure with a single nick or gap between the 5' segment of the second primer and a 3' hydroxyl of an adjacent nucleotide.

In certain embodiments, the extension blocker is a modified nucleobase unit that blocks nucleobase unit extension by a nucleic acid polymerase when the 5' segment of an extension blocking primer serves as a template for nucleobase unit extension in the absence of a partnering nucleobase unit that base pairs with the extension blocker; and the nucleobase unit extension is not blocked by the extension blocker in the presence of a partnering nucleobase unit that base pairs with the extension blocker. In certain related embodiments, the amplification conditions do not contain a partnering nucleobase unit. In other embodiments, the extension blocker is a reversibly modified nucleobase unit that blocks nucleobase unit extension by a nucleic acid polymerase when the 5' segment serves as a template for nucleobase unit extension. In other embodiments, the extension blocker is one or more ribonucleotide units and the nucleic acid polymerase is a DNA dependent DNA polymerase. In certain embodiments, the extension blocker is isoC and the partnering nucleobase unit is isoG. In other embodiments, the extension blocker is isoG and the partnering nucleobase unit is isoC. In certain embodiments, the extension blocker is selected from the group consisting of: nucleotides with hydrolysis resistant modifications at the 2' carbon atom, nucleotides with O-linked triisopropylsilyl groups at the 2' carbon atom, nucleotides with O-linked tert-Butyl-dimethylsilyl groups at the 2' carbon atom; nucleotides with O-linked alkyl groups at the 2' carbon atom, and an A, C, T/U, or G nucleotide with a —$OSiC_6$ group at the 2' carbon atom.

In certain embodiments, the blocking group member of the extension blocker nucleotide is removed so that nucleobase unit extension is not blocked by the extension blocker. In other embodiments, an RNA dependent DNA polymerase is used so that nucleobase unit extension is not blocked by the extension blocker.

In certain embodiments, the closed nucleic acid is used in a reaction that includes the step of performing a nucleobase unit extension by a nucleic acid polymerase, wherein the extension blocker does not block nucleobase unit extension by a nucleic acid polymerase. In certain embodiments, the closed nucleic acid structure is used in a sequencing reaction. In certain embodiments, nucleobase unit extension blocking by the extension blocker is reversed.

In another aspect, the invention provides methods of forming a closed nucleic acid structure from a target nucleic acid, comprising: (a) denaturing a target nucleic acid; (b) annealing a non-extendible blocker pair, a displacer pair, and a primer pair to opposing strands of the denatured target nucleic acid, each of the primers having a 3' segment and a 5' segment, the 3' segments of the primers being target-binding segments, the 5' segments being complementary in opposing orientations, a first of the primers having a 5' phosphate group and the second of the primers lacking a 5' phosphate and/or having a shorter 5' segment than the first primer; wherein the blocker binds to the denatured target nucleic acid downstream of the primer, and the displacer binds to the denatured target nucleic acid upstream of the primer; (c) extending the primers with a nucleic acid polymerase to obtain primer-extended target nucleic acids, some of which have a strand with an overhanging 5' segment from the first primer and others of which have an opposing strand with an overhanging 5' segment from the second primer; wherein the extension of the primers is terminated downstream by the blocker pair; (d) extending the displacers with a nucleic acid polymerase, wherein the extensions of the displacers displace and release the primer-extended target nucleic acids; (e) annealing strands of the displaced primer-extended target nucleic acids having overhanging 5' segments, wherein strands and opposing strands anneal to one another and circularize by annealing of the 5' segments, thereby forming a closed nucleic acid structure; and (f) contacting the closed nucleic acid structure with a ligase which seals a nick between the 5' phosphate group of the first primer and an adjacent 3' hydroxyl group leaving the closed nucleic acid structure with a single nick or gap between the 5' segment of the second primer and a 3' hydroxyl of an adjacent nucleotide.

In another aspect, the invention provides methods of forming a closed nucleic acid structure from a target nucleic acid, comprising: (a) denaturing a target nucleic acid; (b) annealing a non-extendible blocker pair, and a primer pair to opposing strands of the denatured target nucleic acid, each of the primers having a 3' segment and a 5' segment, the 3' segments of the primers being target-binding segments, the 5' segments being complementary in opposing orientations, a first of the primers having a 5' phosphate group and the second of the primers lacking a 5' phosphate and/or having a shorter 5' segment than the first primer; wherein the blocker binds to the denatured target nucleic acid downstream of the primer; (c) extending the primers with a nucleic acid polymerase to obtain primer-extended target nucleic acids, some of which have a strand with an overhanging 5' segment from the first primer and others of which have an opposing strand with an overhanging 5' segment from the second primer; wherein the extension of the primers is blocked by the blocker pair; (d) denaturing the primer-extended target nucleic acids; (e) annealing strands of the denatured primer-extended target nucleic acids having overhanging 5' segments, wherein strands and opposing strands anneal to one another and circularize by annealing of the 5' segments thereby forming a closed nucleic acid structure; and (f) contacting the closed nucleic acid structure with a ligase which seals a nick between the 5' phosphate group of the first primer and an adjacent 3' hydroxyl group leaving the closed nucleic acid structure with a single nick or gap between the 5' segment of the second primer and a 3' hydroxyl of an adjacent nucleotide.

In another aspect, the invention provides methods of forming a closed nucleic acid structure from a target nucleic acid, comprising: (a) denaturing a target nucleic acid; (b) annealing a non-extendible blocker pair, a displacer pair, and a primer pair to opposing strands of the denatured target nucleic acid, each of the primers having a 5' phosphate group, each of the primers having a 3' segment and a 5' segment, the 3' segments of the primers being target-binding segments; wherein the blocker binds to the denatured target nucleic acid downstream of the primer, and the displacer binds to the denatured target nucleic acid upstream of the primer; (c) extending the primers with a nucleic acid polymerase to obtain primer-extended target nucleic acids, some of which have a strand with an overhanging 5' segment from the first primer and others of which have an opposing strand with an overhanging 5' segment from the second primer; wherein the extension of the primers is blocked by the blocker pair; (d) extending the displacers with a nucleic acid polymerase, wherein the extensions of the displacers displace and release the primer-extended target nucleic acids; (e) annealing strands and opposing strands of the displaced primer-extended target nucleic acids having overhanging 5' segments, and a first adaptor and a second adaptor, both having a 5' region and a 3' region, to form an adaptor-capped nucleic acid having one strand comprising the 5' segment from the first primer and an opposing strand comprising the 5' segment from the second primer, and adaptors annealed to the 5' segments of the primers at both ends of the adaptor-capped nucleic acid; wherein the 3' region of the adaptor comprises a stem-loop structure, the 5' region of the adaptor having a 5' phosphate group, and the 5' region of the first adaptor is complementary to the 5' segment of the first primer and the 5' region of the second adaptor is complementary to the 5' segment of the second primer; and (f) contacting the adaptor-capped nucleic acid with a ligase which seals a nick in the adaptor-capped nucleic acid thereby forming a closed nucleic acid structure.

In another aspect, the invention provides methods of forming a closed nucleic acid structure from a target nucleic acid, comprising: (a) denaturing a target nucleic acid; (b) annealing a non-extendible blocker pair, and a primer pair to opposing strands of the denatured target nucleic acid, each of the primers having a 5' phosphate group, each of the primers having a 3' segment and a 5' segment, the 3' segments of the primers being target-binding segments; wherein the blocker binds to the denatured target nucleic acid downstream of the primer; (c) extending the primers with a nucleic acid polymerase to obtain a primer-extended target nucleic acids, some of which have a strand with an overhanging 5' segment from the first primer and others of which have an opposing strand with an overhanging 5' segment from the second primer; wherein the extension of the primers is blocked by the blocker pair; (d) denaturing the primer-extended target nucleic acids; (e) annealing strands and opposing strands of the denatured primer-extended target nucleic acids having overhanging 5' segments, and a first adaptor and a second adaptor, both having a 5' region and a 3' region, to the denatured primer-extended target nucleic acids to form an adaptor-capped nucleic acid having one strand comprising the 5' segment from the first primer and an opposing strand comprising the 5' segment from the second primer, and adaptors annealed to the 5' segments of the primers at both ends of the adaptor-capped nucleic acid; wherein the 3' region of the adaptor comprises a stem-loop structure, the 5' region of the adaptor having a 5' phosphate group, and the 5' region of the first adaptor is complementary to the 5' segment of the first primer and the 5' region of the second adaptor is complementary to the 5' segment of the second primer; and (f) contacting the adaptor-capped nucleic acid with a ligase which seals a nick in the adaptor-capped nucleic acid, thereby forming a closed nucleic acid structure.

In another aspect, the invention provides methods of forming a closed nucleic acid structure from a target nucleic acid, comprising: (a) denaturing a target nucleic acid; (b) annealing a non-extendible blocker pair, a displacer pair, and a primer pair to opposing strands of the denatured target nucleic acid, each of the primers having a 5' phosphate group, each of the primers having a 3' segment and a 5' segment, the 3' segments of the primers being target-binding segments, the 5' segments comprises a stem-loop structure; wherein the blocker binds to the denatured target nucleic acid downstream of the primer, and the displacer binds to the denatured target nucleic acid upstream of the primer; (c) extending the primers with a nucleic acid polymerase to obtain a primer-extended target nucleic acids, some of which have a strand with an overhanging 5' segment stem-loop from the first primer and others of which have an opposing strand with an overhanging 5' segment stem-loop from the second primer; wherein the extension of the primers are blocked by the blocker pair; (d) extending the displacers with a nucleic acid polymerase, wherein the extensions of the displacers displace and release the primer-extended target nucleic acids; (e) annealing strands and opposing strands of the displaced primer-extended target nucleic acids having overhanging 5' segment stem-loops to obtain a closed nucleic acid structure; and (f) contacting the template with a ligase which seals a nick in the closed nucleic acid structure.

In another aspect, the invention provides methods of forming a closed nucleic acid structure from a target nucleic acid, comprising: (a) denaturing a target nucleic acid; (b) annealing a non-extendible blocker pair, and a primer pair to opposing strands of the denatured target nucleic acid, each of the primers having a 5' phosphate group, each of the primers having a 3' segment and a 5' segment, the 3' segments of the primers being target-binding segments, the 5' segments comprises a stem-loop structure; wherein the blocker binds to the denatured target nucleic acid downstream of the primer; (c) extending the primers with a nucleic acid polymerase to obtain primer-extended target nucleic acids, some of which have a strand with an overhanging 5' segment stem-loop from the first primer and others of which have an opposing strand with an overhanging 5' segment stem-loop from the second primer; wherein the extension of the primers are blocked by the blocker pair; (d) denaturing the primer-extended target nucleic acids; (e) annealing strands and opposing strands of the denatured primer-extended target nucleic acids having overhanging 5' segment stem-loops to obtain a closed nucleic acid structure; and (f) contacting the closed nucleic acid structure with a ligase which seals a nick in the template.

In another aspect, the invention provides methods of forming a closed nucleic acid structure from a target nucleic acid, comprising: (a) denaturing a target nucleic acid; (b) annealing a non-extendible blocker pair, a displacer pair, and a primer pair to opposing strands of the denatured target nucleic acid, each of the primers having a 5' phosphate group, each of the primers having a 3' segment and a 5' segment, the 3' segments of the primers being target-binding segments, the 5' segments comprises a stem-loop structure; wherein the blocker binds to the denatured target nucleic acid downstream of the primer, and the displacer binds to the denatured target nucleic acid upstream of the primer; (c) extending the primers with a nucleic acid polymerase to obtain primer-extended target nucleic acids, some of which have a strand with an overhanging 5' segment stem-loop from the first primer and others of which have an opposing strand with an overhanging 5' segment stem-loop from the second primer; wherein the extension of the primers are blocked by the blocker pair; (d) extending the displacers with a nucleic acid polymerase, wherein the extensions of the displacers displace and release the primer-extended target nucleic acids; (e) amplifying the displaced primer-extended target nucleic acids with the primer pair under PCR conditions; during the extension cycles of the amplification, the primers extend through the 5' stem-loop region of the primer-extended target nucleic acids, resulting in an amplified nucleic acid having a stem-loop at both ends, some of which have a strand comprising a 5' stem-loop from the first primer and a 3' stem-loop having a sequence complementary to the 5' stem-loop from the second primer, others of which have an opposing strand comprising a 5' stem-loop from the second primer and a 3' stem-loop having a sequence complementary to the 5' stem-loop from the first primer; (f) annealing the strands and opposing strands of the amplified nucleic acids to obtain a closed nucleic acid structure; and (g) contacting the closed nucleic acid structure with a ligase which seals a nick between the 5' phosphate group of a 5' stem-loop and an adjacent 3' hydroxyl group of a 3' stem-loop from the opposing strand.

In another aspect, the invention provides methods of forming a closed nucleic acid structure from a target nucleic acid, comprising: (a) denaturing a target nucleic acid; (b) annealing a non-extendible blocker pair, and a primer pair to opposing strands of the denatured target nucleic acid, each of the primers having a 5' phosphate group, each of the primers having a 3' segment and a 5' segment, the 3' segments of the primers being target-binding segments, the 5' segments comprises a stem-loop structure; wherein the blocker binds to the denatured target nucleic acid downstream of the primer, (c) extending the primers with a nucleic acid polymerase to obtain a primer-extended target nucleic acids, some of which have a strand with an overhanging 5' segment stem-loop from the first primer and others of which have an opposing strand with an overhanging 5' segment stem-loop from the second primer; wherein the extension of the primers are blocked by the blocker pair; (d) denaturing the primer-extended target nucleic acids; (e) amplifying the denatured primer-extended target nucleic acids with the primer pair under PCR conditions; during the extension cycles of the amplification, the primers extend through the 5' stem-loop region of the denatured primer-extended target nucleic acids, resulting in an amplified nucleic acid having a stem-loop at both ends, some of which have a strand comprising a 5' stem-loop from the first primer and a 3' stem-loop having a sequence complementary to the 5' stem-loop from the second primer, others of which have an opposing strand comprising a 5' stem-loop from the second primer and a 3' stem-loop having a sequence complementary to the 5' stem-loop from the first primer; (f) annealing the strands and opposing strands of the amplified nucleic acids to obtain a closed nucleic acid structure; and (g) contacting the closed nucleic acid structure with a ligase which seals a nick between the 5' phosphate group of a 5' stem-loop and an adjacent 3' hydroxyl group of a 3' stem-loop from the opposing strand.

In another aspect, the invention provides methods of forming a closed nucleic acid structure from a target nucleic acid, comprising: (a) contacting a target nucleic acid with a primer pair under PCR conditions, each of the primers having a 5' phosphate group, each of the primers having a 3' segment and a 5' segment, the 3' segments of the primers being target-binding segments, the 5' segments comprises a stem-loop structure, the first 3'→5' nucleobase unit in the 5' segment is an extension blocker; wherein the extension blocker blocks nucleobase unit extension by a nucleic acid polymerase when the 5' segment serves as a template for nucleobase unit extension, thereby forming an amplified target nucleic acid having a strand comprising an overhanging 5' segment stem-loop from the first primer and an opposing strand comprising an overhanging 5' segment stem-loop from the second primer; wherein the extension blocker blocks nucleobase unit extension by a nucleic acid polymerase when the 5' segment serves as a template for nucleobase unit extension in the absence of a partnering nucleobase unit that base pairs with the extension blocker, the nucleobase unit extension is not blocked by the extension blocker in the presence of a partnering nucleobase unit that base pairs with the extension blocker; and wherein the PCR conditions do not contain a partnering nucleobase unit; (b) contacting the amplified target nucleic acid with a ligase which seals a nick between the 5' phosphate group of a 5' stem-loop and an adjacent 3' hydroxyl group of a 3' stem-loop from the opposing strand thereby forming a closed nucleic acid structure.

In certain embodiments, the extension blocker is isoC and the partnering nucleobase unit is isoG. In other embodiments, the extension blocker is isoG and the partnering nucleobase unit is isoC.

In another aspect, the invention provides methods of forming a closed nucleic acid structure from a target nucleic acid, comprising: (a) contacting a target nucleic acid with a primer pair under PCR conditions, each of the primers having a 5' phosphate group, each of the primers having a 3' segment and a 5' segment, the 3' segments of the primers being target-binding segments, the 5' segments comprises a stem-loop structure, the first 3'→5' nucleobase unit in the 5' segment is an extension blocker; wherein the extension blocker blocks nucleobase unit extension by a nucleic acid polymerase when the 5' segment serves as a template for nucleobase unit extension, thereby forming an amplified target nucleic acid having a strand comprising an overhanging 5' segment stem-loop from the first primer and an opposing strand comprising an overhanging 5' segment stem-loop from the second primer; wherein the extension blocker blocks nucleobase unit extension by a nucleic acid polymerase when the 5' segment serves as a template for nucleobase unit extension in the absence of a partnering nucleobase unit that base pairs with the extension blocker, the nucleobase unit extension is not blocked by the extension blocker in the presence of a partnering nucleobase unit that base pairs with the extension blocker; and wherein the PCR conditions contain a partnering nucleobase unit; and (c) contacting the amplified target nucleic acid with a ligase which seals a nick between the 5' phosphate group of a 5' stem-loop and an adjacent 3' hydroxyl group of a 3' stem-loop from the opposing strand thereby forming a closed nucleic acid structure.

In certain embodiments, the extension blocker is isoC and the partnering nucleobase unit is isoG. In other embodiments, the extension blocker is isoG and the partnering nucleobase unit is isoC.

In another aspect, the invention provides methods of forming a closed nucleic acid structure from a target nucleic acid, comprising: (a) annealing a non-extendible blocker, a displacer, and a primer to a target nucleic acid, the primer having a duplex region flanked by a first overhanging 3' segment in a first strand and a second overhanging 3' segment in an opposing strand, the first overhanging 3' segment being target-binding segment, wherein the first strand having a 5' phosphate group, wherein the blocker binds to the denatured target nucleic acid downstream of the primer, and the displacer binds to the denatured target nucleic acid upstream of the primer, and the second overhanging 3' segments of the primer having a sequence of that of a region in the target nucleic acid upstream of and adjacent to the blocker; (b) extending the first overhanging 3' segment of the primer with a nucleic acid polymerase to obtain a primer-extended target nucleic acid; wherein the extension of the primer is blocked by the blocker, and a 3' end region of the primer-extended target nucleic acid is complementary to the second overhanging 3' segment of the primer; (c) extending the displacer with a nucleic acid polymerase, wherein the extensions of the displacers displace and release the primer-extended target nucleic acid; (d) annealing the second overhanging 3' segment to its complementary region at the 3' end of the primer-extended target nucleic acid, thereby forming a closed nucleic acid structure; and (e) contacting the closed nucleic acid structure with a ligase which seals a nick in the closed nucleic acid structure.

In another aspect, the invention provides methods of forming a closed nucleic acid structure from a target nucleic acid, comprising: (a) annealing a non-extendible blocker, and a primer to a target nucleic acid, the primer having a duplex region flanked by a first overhanging 3' segment in a first strand and a second overhanging 3' segment in an opposing strand, the first overhanging 3' segment being target-binding segment, wherein the first strand having a 5' phosphate group, wherein the blocker binds to the denatured target nucleic acid downstream of the primer, and the second overhanging 3' segments of the primer having a sequence of that of a region in the target nucleic acid upstream of and adjacent to the blocker; (b) extending the first overhanging 3' segments of the primer with a nucleic acid polymerase to obtain a primer-extended target nucleic acid; wherein the extension of the primer is blocked by the blocker, and a 3' end region of the primer-extended target nucleic acid is complementary to the second overhanging 3' segments of the primer; (c) denaturing the primer-extended target nucleic acid; (d) annealing the second overhanging 3' segment to its complementary region at the 3' end of the primer-extended target nucleic acid, thereby forming a closed nucleic acid structure; and (e) contacting the closed nucleic acid structure with a ligase which seals a nick in the closed nucleic acid structure.

In another aspect, the invention provides methods of forming a closed nucleic acid structure from a target nucleic acid, comprising: (a) contacting a target nucleic acid with a primer pair under PCR conditions, each of the primers having a duplex region flanked by a first overhanging 3' segment in a first strand and a second overhanging 3' segment in an opposing strand, the first overhanging 3' segment being target-binding segment, wherein the first strand having a 5' phosphate group, the first 3'→5' nucleobase unit in the 5' segment is an extension blocker; wherein the extension blocker blocks nucleobase unit extension by a nucleic acid polymerase when the 5' segment serves as a template for nucleobase unit extension, thereby forming an amplified target nucleic acid having a strand comprising a duplex region and a second overhanging 3' segment from the first primer and an opposing strand comprising a duplex region and a second overhanging 3' segment from the second primer; wherein the extension blocker blocks nucleobase unit extension by a nucleic acid polymerase when the 5' segment serves as a template for nucleobase unit extension in the absence of a partnering nucleobase unit that base pairs with the extension blocker, the nucleobase unit extension is not blocked by the extension blocker in the presence of a partnering nucleobase unit that base pairs with the extension blocker; wherein the PCR conditions do not contain a partnering nucleobase unit; (b) denaturing the amplified target nucleic acid; wherein the denaturing separates the second strand of the first primer and the second strand of the second primer from the amplified target nucleic acid, resulting in a first denatured strand having a 5' segment from the first strand of the first primer and a second denatured strand having a 5' segment from the first strand of the second primer; (c) annealing the second strand of the first primer to the first denatured strand, wherein the 5' segment of the second strand of the first primer hybridizes to the 5' segment of the first strand of the first primer from the first denatured strand, and the 3' segment of the second strand of the first primer hybridizes to its complementary region at the 3' end of the first denatured strand; and/or annealing the second strand of the second primer to the second denatured strand, wherein the 5' segment of the second strand of the second primer hybridizes to the 5' segment of the first strand of the second primer from the second denatured strand, and the 3' segment of the second strand of the second primer hybridizes to its complementary region at the 3' end of the second denatured strand; and (d) contacting the annealed nucleic acids with a ligase which seals a nick between the 5' phosphate group of the first denatured strand and the adjacent 3' hydroxyl group from the 3' end of the first denatured strand; and/or a nick between the 5' phosphate group of the second denatured strand and the adjacent 3' hydroxyl group from the 3' end of the second denatured strand; thereby forming a closed nucleic acid structure.

In certain embodiments, the first overhanging 3' segment of the first primer is the same as the second overhanging 3' segment of the second primer. In certain embodiments, the first overhanging 3' segment of the second primer is the same as the second overhanging 3' segment of the first primer.

In another aspect, the invention provides methods of forming a closed nucleic acid structure from a target nucleic acid, comprising: (a) contacting a target nucleic acid with a primer pair under PCR conditions, each of the primers having a 5' phosphate group, each of the primers having a 3' segment and a 5' segment, the 3' segments of the primers being target-binding segments, the 5' segments being non-complementary to one another, thereby forming an amplified nucleic acid; (b) contacting the amplified nucleic acid with a nucleic acid polymerase having a 3' to 5' exonuclease activity and one or more nucleobase units in solution, wherein the polymerase with exonuclease activity digests at least parts of the amplified nucleic acid complementary to the 5' segments of the primers, the digested nucleobase units of the parts complementary to the 5' segments being of a type different than the one or more nucleobase units in solution; (c) annealing a first adaptor and a second adaptor, both having a 5' region and a 3' region, to the digested nucleic acids to form an adaptor-capped nucleic acid, wherein the 3' region of the adaptor comprises a stem-loop structure, the 5' region of the adaptor having a 5' phosphate group, and the 5' region of the first adaptor is complementary to the 5' segment of the first primer and the 5' region of the second adaptor is complementary to the 5' segment of the second primer; and (d) contacting the adaptor-capped nucleic acid with a ligase which seals a nick between the 5' phosphate group of the adaptors and an adjacent 3' hydroxyl group from the digested nucleic acids and/or a nick between the 5' phosphate group of the 5' segment of the digested nucleic acids and an adjacent 3' hydroxyl group from the 3' region of the adaptor thereby forming a closed nucleic acid structure.

In certain embodiments, the nucleic acid polymerase is a DNA polymerase. In certain embodiments, the nucleic acid polymerase is a T4 DNA polymerase. In certain embodiments, each primer further comprises a cushion segment between the 5' segment and the 3' segment, the cushion segment including at least one nucleobase unit complementary to a type of the one or more nucleobase units in solution, whereby the exonuclease digestion terminates at or in the complements of the cushion segments in the amplified nucleic acid. In certain embodiments, the cushion segment nucleobase unit(s) consist of a single type of canonical nucleobase unit, and the 5' segment nucleobase units consist of the three canonical nucleobase types other than the single type of canonical nucleobase. In certain embodiments, a 5' segment or cushion segment of the first and/or second primer includes one or more non-canonical nucleobase units.

In another aspect, the invention provides methods of forming a closed nucleic acid structure from a target nucleic acid, comprising: (a) contacting a target nucleic acid with a primer pair under PCR conditions, each of the primers having a 5' phosphate group, thereby forming an amplified nucleic acid comprising a segment of the target nucleic acid flanked by the primers duplexed with their complementary segments; (b) contacting the amplified nucleic acid with a terminal deoxynucleotidyl transferase (TdT) and a first deoxynucleotide thereby extending the 3' ends of the amplified nucleic acid with a homo-oligomeric tail comprising the first deoxynucleotide; (c) annealing an adaptor having a 5' region and a 3' region to the extended nucleic acid, the 5' region of the adaptor having a 5' phosphate group and comprising a stem-loop structure, and the 3' region of the adaptor being complementary to the homo-oligomeric tail of the extended nucleic acid, wherein the 3' region of the adaptor hybridizes to the homo-oligomeric tail thereby forming an adaptor-capped nucleic acid; (d) contacting the adaptor-capped nucleic acid with the first deoxynucleotide and/or a second deoxynucleotide which is complementary to the first deoxynucleotide, and a DNA polymerase, thereby filling in any gap in the adaptor-capped nucleic acid with the first or the second deoxynucleotide; and (e) contacting the closed nucleic acid structure with a ligase which seals nicks in the closed nucleic acid structure.

In certain embodiments, the first deoxynucleotide is dATP, and the second deoxynucleotide is dTTP/dUTP. In certain embodiments, the DNA polymerase is a T4 DNA polymerase.

In certain embodiments, the 5' segments of the primers used in any of the foregoing methods of the invention are the same. In other embodiments, the 5' segments of the primers used in any of the foregoing methods are complementary in opposing orientations. In still other embodiments, the 5' segments of the primers used in any of the foregoing methods are not complementary in opposing orientations. In certain embodiments, the 5' segments of the primers used in any of the foregoing methods have different sequence and/or length. For example, in certain embodiments, the 5' segment of the first primer is longer than the 5' segment of the second primer resulting in a gap between the 5' end of the second primer and a 3' hydroxyl of an adjacent nucleotide in the amplified nucleic acid. In certain embodiments, the 5' segment of the first primer is longer than the 5' segment of the second primer by four nucleobase units and the gap is four nucleobase units.

In certain embodiments, the primer(s) used in any of the foregoing methods is extended in one cycle of extension reaction. In certain embodiments, the PCR conditions of any of the foregoing methods including at least ten thermocycles.

In certain embodiments, the first and second adaptors used in any of the foregoing methods are the same. In certain embodiments, the 5' regions of the first and second adaptors are the same. In other embodiments, the 5' regions of the first and second adaptors have different sequence and/or length. In certain embodiments, the 5' regions of the first and second adaptors are not complementary in opposing orientations.

In another aspect, the invention provides methods of forming a closed nucleic acid structure comprising a segment of a target nucleic acid, comprising: (a) contacting a target nucleic acid with a linear primer pair under amplification conditions, each of the primers of the pair having a 3' segment and a 5' segment, the 3' segments of the primers being target-binding segments; thereby forming a double-stranded amplified nucleic acid comprising duplex target nucleic acid flanked by the primers of the pair duplexed with their complementary segments; (b) denaturing the amplified nucleic acid and contacting at least one strand of the denatured amplified nucleic acid with a stem-loop primer having a phosphate group on the 5' end, a 5' segment having a stem-loop structure, and a 3' segment having a proximal 3' sub-segment and a distal 3' sub-segment, wherein the proximal 3' segment and the 5' segment of a first primer of the linear primer pair have a common sequence, and wherein the distal 3' segment and the 5' segment of the second primer of the linear primer pair have a common sequence; (c) annealing the distal 3' segment of the stem-loop primer to the complement of the 5' segment of the second primer in the at least one strand of the denatured amplified nucleic acid, thereby providing a template for extension from the stem-loop primer; (d) forming an extended strand duplexed to an amplified nucleic acid strand, the extended strand comprising from 5'-3' the stem-loop primer, a strand of the target nucleic acid, and a segment complementary to the first primer, the 5' end being the phosphorylated 5' end of the stem-loop primer and the 3' end having a 3' hydroxyl group; (e) denaturing the extended strand from the amplified nucleic acid strand; (f) allowing the extended strand to hybridize intramolecularly by annealing of a segment at its 3' end to the proximal 3' sub-segment of the stem-loop primer, thereby forming a circularized nucleic acid having a nick separating the 5' phosphate group and the 3' hydroxyl group; and (g) providing a ligase that seals the nick between the 5' phosphate group and the 3' hydroxyl group, thereby forming a closed nucleic acid structure.

In certain embodiments, one or both of the primers in the linear primer pair is attached to a solid support. In certain embodiments, the 5' segment of one or both of the primers in the linear primer pair is a target-binding segment. In certain embodiments, the stem-loop primer includes an addition segment between the 5' and 3' segments, wherein the additional segment comprises or consists of 1, 2, 3, 4, or more T nucleobase units.

In another aspect, the invention provides methods of forming a closed nucleic acid structure comprising a segment of a target nucleic acid, comprising: (a) contacting a target nucleic acid with a primer pair under amplification conditions, each of the primers of the pair including a 5' phosphate group and a 3' segment, the 3' segments of the primers being target-binding segments; thereby forming an amplified nucleic acid comprising duplex target nucleic acid flanked by the primers of the pair duplexed with their complementary segments, wherein each strand of the amplified nucleic acid includes a 5' phosphate group and a 3' hydroxyl group; (b) denaturing the amplified nucleic acid and contacting a strand of the denatured amplified nucleic acid with a stem-loop adaptor having a 5' phosphate group, a 5' segment, a 3' segment having a stem-loop structure, and a 3' hydroxyl group, wherein the 5' segment is complementary to a segment at the 5' end of the amplified nucleic acid strand; (c) annealing the 5' segment of the stem-loop adaptor to the 5' end segment of the amplified nucleic acid strand, thereby forming a partially duplex, two-stranded intermediate structure wherein the 5' phosphate group of the amplified nucleic acid strand is separated by a nick from the 3' hydroxyl group of the stem-loop adaptor; and (d) providing a ligase that seals the nick between the 5' phosphate group of the amplified nucleic acid strand and the 3' hydroxyl group of the stem-loop adaptor and additionally links the 5' phosphate group of the stem-loop adaptor to the 3' hydroxyl group of the amplified nucleic acid strand, thereby forming a closed nucleic acid structure.

In certain embodiments, a segment of the amplified nucleic acid strand located immediately adjacent and internal to the 5' end segment is complementary to a segment at the 3' end of the amplified nucleic acid strand. In certain embodiments, at least the 3'-most nucleobase unit of the 3' end segment is complementary to the 5'-most nucleobase unit of the segment adjacent to the 5' end segment. In certain embodiments, the 3' end segment of the amplified nucleic acid strand is capable of forming at least 2, 3, or 4 nucleobase unit pairs with the segment adjacent to the 5' end segment. In certain embodiments, at least a first primer of the pair includes a 5' segment located between the 5' phosphate group and the 3' segment. In certain embodiments, the 5' segment of the first primer of the pair includes a sequence which is complementary to the 5' segment of the stem-loop adaptor. In certain embodiments, the first primer of the pair includes an additional segment between the 5' and 3' segments, wherein the additional segment is complementary to a segment at the 3' end of the amplified nucleic acid strand.

In certain embodiments, the foregoing methods further comprise: (e) contacting a complementary strand of the denatured amplified nucleic acid with a second stem-loop adaptor having a 5' phosphate group, a 5' segment, a 3' segment having a stem-loop structure, and a 3' hydroxyl group, wherein the 5' segment is complementary to a segment at the 5' end of the complementary amplified nucleic acid strand; (f) annealing the 5' segment of the second stem-loop adaptor to the 5' end segment of the denatured complementary amplified nucleic acid strand, thereby forming a partially duplex, two-stranded nucleic acid structure wherein the 5' phosphate group of the complementary amplified nucleic acid strand is separated by a nick from the 3' hydroxyl group of the second stem-loop adaptor; and (g) providing a ligase that seals the nick between the 5' phosphate group of the complementary amplified nucleic acid strand and the 3' hydroxyl group of the second stem-loop adaptor and additionally links the 5' phosphate group of the second stem-loop adaptor to the 3' hydroxyl group of the complimentary amplified nucleic acid strand, thereby forming a closed nucleic acid structure.

In certain embodiments, a segment of the complementary amplified nucleic acid strand located immediately adjacent and internal to the 5' end segment is complementary to a segment at the 3' end of the complimentary amplified nucleic acid strand. In certain embodiments, the second primer of the pair includes a 5' segment located between the 5' phosphate group and the 3' segment. In certain embodiments, the 5' segment of the second primer of the pair includes a sequence tag which is complementary to the 5' segment of the second stem-loop adaptor. In certain embodiments, the second primer of the pair includes an additional segment between the 5' and 3' segments, wherein the additional segment is complementary to a segment at the 3' end of the complementary amplified nucleic acid strand. In certain embodiments, the steps (e), (f), and (g) are performed in parallel or in series with steps (b), (c), and (d). In certain embodiments, the steps (e), (f), and (g) are performed in reaction mixtures which are the same reaction mixtures in which with steps (b), (c), and (d), respectively, are performed.

In another aspect, the invention provides methods of forming a closed nucleic acid structure comprising a segment of a target nucleic acid, comprising: (a) contacting a target nucleic acid with a primer having a 5' phosphate group and a 3' segment, the 3' segment being a target-binding segment; (b) annealing the 3' segment of the primer to the target nucleic acid, thereby forming a template for extension from the primer; (c) forming an extended nucleic acid strand duplexed to the target nucleic acid, the extended strand comprising from 5'-3' the primer and a segment complementary to the target nucleic acid, the 5' end of the extended strand being the phosphorylated 5' end of the primer and the 3' end of the extended strand having a 3' hydroxyl group; (d) denaturing the extended strand from the template nucleic acid and contacting the extended strand with a stem-loop adaptor having a 5' phosphate group, a 5' segment, a 3' segment having a stem-loop structure, and a 3' hydroxyl group, wherein the 5' segment is complementary to a segment at the 5' end of the extended strand; (e) annealing the 5' segment of the stem-loop adaptor to the 5' segment of the extended strand, thereby forming a partially duplex, two-stranded intermediate structure wherein the 5' phosphate group of the extended strand is separated by a nick from the 3' hydroxyl group of the stem-loop adaptor; and (f) providing a ligase that seals the nick between the 5' phosphate group of the extended strand and the 3' hydroxyl group of the stem-loop adaptor and additionally links the 5' phosphate group of the stem-loop adaptor to the 3' hydroxyl group of the extended strand, thereby forming a closed nucleic acid structure.

In certain embodiments, a segment of the extended strand located immediately adjacent and internal to the 5' end segment is complementary to a segment at the 3' end of the extended strand. In certain embodiments, at least the 3'-most nucleobase unit of the 3' end segment is complementary to the 5'-most nucleobase unit of the segment adjacent to the 5' end segment. In certain embodiments, the 3' end segment of the extended strand is capable of forming at least 2, 3, or 4 nucleobase unit pairs with the segment adjacent to the 5' end segment. In certain embodiments, the primer includes a 5' segment located between the 5' phosphate group and the 3' segment. In certain embodiments, the 5' segment of the primer includes a sequence which is complementary to the 5' segment of the stem-loop adaptor. In certain embodiments, the primer includes an additional segment between the 5' and 3' segments, wherein the additional segment is complementary to a segment at the 3' end of the extended strand.

In another aspect, the invention provides methods of forming a closed nucleic acid structure comprising a segment of a target nucleic acid, comprising: (a) contacting a target nucleic acid with a primer having a 5' phosphate group and a 3' segment, the 3' segment being a target-binding segment; (b) annealing the 3' segment of the primer to the target nucleic acid, thereby forming a template for extension from the primer; (c) forming an extended nucleic acid strand duplexed to the target nucleic acid, the extended strand comprising from 5'-3' the primer and a segment complementary to the target nucleic acid, the 5' end of the extended strand being the phosphorylated 5' end of the primer and the 3' end of the extended strand having a 3' hydroxyl group; (d) denaturing the extended strand from the target nucleic acid and contacting the extended strand with a stem-loop adaptor having a 5' phosphate group, a 5' segment having a stem-loop structure, a 3' segment, and a 3' hydroxyl group, wherein the 3' segment is complementary to a segment located at the 3' end of the extended strand; (e) annealing the 3' segment of the stem-loop adaptor to the 3' end segment of the extended strand, thereby forming a partially duplex, two-stranded intermediate structure wherein the 5' phosphate group stem-loop adaptor is separated by a nick from the 3' hydroxyl group of the extended strand; and (f) providing a ligase that seals the nick between the 5' phosphate group of the extended strand and the 3' hydroxyl group of the stem-loop adaptor and additionally links the 5' phosphate group of the stem-loop adaptor to the 3' hydroxyl group of the extended strand, thereby forming a closed nucleic acid structure.

In certain embodiments, a segment of the extended strand located immediately adjacent and internal to the 3' end segment is complementary to a segment at the 5' end of the extended strand. In certain embodiments, at least the 5'-most nucleobase unit of the 5' end segment is complementary to the 3'-most nucleobase unit of the segment adjacent to the 3' end segment. In certain embodiments, the 5' end segment of the extended strand is capable of forming at least 2, 3, or 4 nucleobase unit pairs with the segment adjacent to the 3' end segment. In certain embodiments, the primer includes a 5' segment located between the 5' phosphate group and the 3' segment. In certain embodiments, the 5' segment of the primer includes a sequence which is complementary to a segment of the extended strand located immediately adjacent and internal to the 3' end segment. In certain embodiments, the stem-loop adaptor includes an additional segment between the 5' and 3' segments, wherein the additional segment comprises or consists of 1, 2, 3, 4, or more T nucleobase units. In certain embodiments, the template nucleic acid is single-stranded nucleic acid. In certain embodiments, the template nucleic acid has defined ends. In certain embodiments, the template nucleic acid is amplified nucleic acid that has been denatured or genomic DNA that has been cut with at least one restriction endonuclease and denatured. In certain embodiments, the template nucleic acid does not have defined ends and step (c) is performed in the presence of a blocker oligonucleotide that hybridizes to the template nucleic acid at a position located 5' to the position on the template nucleic acid to which the primer hybridizes. In certain embodiments, the primer anneals to a segment of the template nucleic acid located internal to at least the 3'-most base of the template nucleic acid.

In another aspect, the invention provides methods of forming a closed nucleic acid structure comprising a target nucleic acid, comprising: (a) contacting a target nucleic acid with a first primer having a 3' target-binding segment, thereby forming a template for extension from the first primer; (b) forming a first extended nucleic acid strand duplexed to the target nucleic acid, the first extended strand comprising from 5'-3' the first primer and a segment complementary to the target nucleic acid; c) denaturing the first extended strand from the target nucleic acid and contacting the first extended strand with a second primer having a 5' phosphate group and a 3' segment complementary to a segment of the first extended strand; (d) annealing the 3' segment of the second primer to the first extended strand, thereby forming a template for extension from the second primer; (e) forming a second extended nucleic acid strand duplexed to the first extended strand, the second extended strand comprising from 5'-3' the second primer, a segment complementary to the first extended strand and having a common sequence with the target nucleic acid, and a segment complementary to the first primer, the 5' end of the second extended strand being the phosphorylated 5' end of the second primer and the 3' end of the second extended strand having a 3' hydroxyl group; (f) denaturing the second extended strand from the first extended strand and contacting the second extended strand with an bridging oligonucleotide having a 5' segment and a 3' segment, the 5' segment being complementary to a segment at the 5' end of the second extended strand and the 3' segment being complementary to a segment at the 3' end of the second extended strand; (g) annealing the 5' segment of the bridging oligonucleotide to the 5' segment of the second extended strand and the 3' segment of the bridging oligonucleotide to the 3' segment of the second extended strand, thereby forming a partially duplex, two-stranded intermediate wherein the 5' phosphate group of the second extended strand is separated by a nick from the 3' hydroxyl group of the second extended strand; and (h) providing a ligase that seals the nick between the 5' phosphate and 3' hydroxyl groups of the second extended strand, thereby forming a closed nucleic acid structure.

In certain embodiments, the first primer includes a 5' segment that has a common sequence with the 5' segment of the bridging oligonucleotide. In certain embodiments, the second primer includes a 5' segment complementary to the 5' segment of the bridging oligonucleotide. In certain embodiments, the bridging oligonucleotide includes an additional segment between the 5' and 3' segments, and wherein the additional segment comprises or consists of 1, 2, 3, 4, or more T nucleobase units. In certain embodiments, the target nucleic acid is single stranded. In certain embodiments, the target nucleic acid is part of a duplex. In certain embodiments, the first primer displaces the complementary strand of the duplex.

In certain embodiments, the methods further comprise: (i) contacting a strand complementary to the target nucleic acid in the target nucleic acid duplex with the second primer, thereby forming a template for extension from the second primer; (j) forming a third extended nucleic acid strand duplexed to the strand complementary to the target nucleic acid, the third extended strand comprising from 5'-3' the second primer and a segment having a common sequence with the target nucleic acid; (k) denaturing the third extended strand from the strand complementary to the target nucleic acid and contacting the third extended strand with the first primer, wherein the first primer includes a 5' phosphate group; (l) annealing the 3' segment of the first primer to the third extended strand, thereby forming a template for extension from the first primer; (m) forming a fourth extended nucleic acid strand duplexed to the third extended strand, the fourth extended strand comprising from 5'-3' the first primer, a segment complementary to the third extended strand and having a sequence complementary to the target nucleic acid, and a segment complementary to the second primer, the 5' end of the fourth extended strand being the phosphorylated 5' end of the first primer and the 3' end of the fourth extended strand having a 3' hydroxyl group; (n) denaturing the fourth extended strand from the third extended strand and contacting the fourth extended strand with a second bridging oligonucleotide having a 5' segment and a 3' segment, the 5' segment being complementary to a segment at the 5' end of the fourth extended strand and the 3' segment being complementary to a segment at the 3' end of the fourth extended strand; (o) annealing the 5' segment of the second bridging oligonucleotide to the 5' segment of the fourth extended strand and the 3' segment of the second bridging oligonucleotide to the 3' segment of the fourth extended strand, thereby forming a partially duplex, two-stranded intermediate wherein the 5' phosphate group of the fourth extended strand is separated by a nick from the 3' hydroxyl group of the fourth extended strand; and (p) providing a ligase that seals the nick between the 5' phosphate and 3' hydroxyl groups of the fourth extended strand, thereby forming a closed nucleic acid structure. In certain embodiments, steps (a), (b), (c), (d), (e), (f), (g), and (h) are performed at the same time as steps (i), (j), (k), (l), (m), (n), (o), and (p), respectively. In other embodiments, steps (a), (b), (c), (d), (e), (f), (g), and (h) are performed in reaction mixtures that are the same reaction mixtures in which steps (i), (j), (k), (l), (m), (n), (o), and (p), are respectively performed.

In certain embodiments, the first and/or second primer is attached to a solid support. In certain embodiments, the bridging oligonucleotide or second bridging oligonucleotide is attached to a solid support.

In another aspect, the invention provides methods of forming a closed nucleic acid structure comprising a target nucleic acid, comprising: (a) contacting a target nucleic acid with a primer pair under amplification conditions, each of the primers having a 3' segment and a 5' segment, the 5' segments each having a stem-loop structure and the 3' segments being target-binding segments, wherein the 3' and 5' segments are linked by an intervening segment comprising at least one deoxyribouracil (dU) base; thereby forming a double-stranded amplified nucleic acid comprising duplex target nucleic acid flanked by the primers duplexed with their complementary segments; (b) excising the dU bases from the amplified nucleic acid, wherein the method of excision further removes any bases on the same strand of the amplified nucleic acid located 5' to a dU base; thereby leaving each end of the excised nucleic acid with a 5' phosphate group and a single-stranded 3' overhang having a 3' hydroxyl group, each 3' overhang complementary to the 5' and intervening segments of one of the primers of the primer pair; (c) allowing each 3' overhang of the excised nucleic acid to hybridize intramolecularly into a stem-loop structure, whereby the 3' hydroxyl group of each 3' overhang becomes positioned adjacent to, but separated by a nick from, a 5' phosphate group; and (d) providing a ligase that seals nicks between the 3' hydroxyl and adjacent 5' phosphate groups; thereby forming a closed nucleic acid structure wherein the two strands of the duplex target nucleic acid are joined to one another by the stem-loop structures.

In certain embodiments, the digestion involves treating the amplified nucleic acid with a uracil DNA glycosidase (UNG) and an endonuclease. In certain embodiments, the endonuclease is T4 endonuclease or DNA glycosylase-lyase endo VIII.

In another aspect, the invention provides methods of forming a closed nucleic acid structure comprising a target nucleic acid, comprising: (a) contacting a target nucleic acid with a primer pair under PCR conditions, each of the primers having a 5' segment and a 3' segment, the 3' segment being a target-binding segment linked to the 5' segment by an intervening segment comprising at least one deoxyribo-uracil (dU) base; thereby forming a double-stranded amplified nucleic acid comprising duplex target nucleic acid flanked by the primers duplexed with their complementary segments; (b) excising the dU bases from the amplified nucleic acid, wherein the method of excising also removes any bases on the same strand of the amplified nucleic acid located 5' to a dU base; thereby leaving each end of the excised nucleic acid with a 5' phosphate and a single-stranded 3' overhang having a 3' hydroxyl, each 3' overhang complementary to the 5' segment of one of the primers of the primer pair; (c) annealing a pair of stem-loop adaptors to the excised nucleic acid, each of the adaptors having a 3' segment and a 5' segment, the 5' segments each having a 5' phosphate and a stem-loop structure, wherein the 3' segments of the adaptors are complementary to and anneal to the 3' overhangs of the excised nucleic acid; and (d) providing a ligase that seals nicks between the ends of the adaptors and the ends of the excised nucleic acid; thereby forming a closed nucleic acid structure wherein the two strands of the duplex target nucleic acid are joined to one another by the stem-loop structures.

In certain embodiments, the digestion involves treating the amplified nucleic acid with a uracil DNA glycosidase (UNG) and an endonuclease. In certain embodiments, the endonuclease is T4 endonuclease or DNA glycosylase-lyase endo VIII. In certain embodiments, the stem-loop adaptors include an additional segment between the 5' and 3' segments, wherein the additional segment comprises or consists of 1, 2, 3, 4, or more T nucleobase units.

In another aspect, the invention provides methods of forming a closed nucleic acid structure comprising a target nucleic acid, comprising: (a) providing a denatured target nucleic acid, each strand of the denatured target nucleic acid having a 5' phosphate and a 3' segment; (b) contacting the strands of the denatured target nucleic acid with a pair of 3' blocked stem-loop oligonucleotides, each oligonucleotide having a 3' segment and a 5' segment, the 3' segments being complementary to the 3' segments of the denatured target nucleic acid strands and the 5' segments each having a sequence capable of forming a stem-loop structure; (c) annealing the 3' segments of the 3' blocked stem-loop oligonucleotides to the 3' segments of the denatured target nucleic acid strands, whereby each oligonucleotide provides a template for extension of the denatured target nucleic acid strand to which it is annealed; (d) extending the denatured target nucleic acid strands to form 3' extended nucleic acid strands, each 3' extended nucleic acid strand having from 5'-3' a 5' phosphate group, a strand of the target nucleic acid, a 3' extension complementary to the 5' segment of a 3' blocked stem-loop oligonucleotide, and a 3' hydroxyl group; (e) separating the 3' blocked stem-loop oligonucleotides from the 3' extended nucleic acid strands; (f) allowing intramolecular hybridization of the 3' extensions of the 3' extended nucleic acid strands and intermolecular hybridization between the 3' extended nucleic acid strands; thereby forming a target nucleic acid duplex having 3' extensions, wherein the 3' extensions have stem-loop structures and the 5' phosphate group of each strand in the duplex is separated from the 3' hydroxyl of the other strand by a nick; and (g) providing a ligase that seals the nicks, thereby forming a closed nucleic acid structure including the two strands of the target nucleic acid joined to one another by stem-loop structures.

In certain embodiments, the 3' blocked stem-loop oligonucleotides contain deoxyribo-uracil and are separated from the extended target nucleic acid strands by digestion with a uracil DNA glycosidase (UNG) and an endonuclease. In certain embodiments, the 3' blocked stem-loop oligonucleotides comprise an affinity label. In certain embodiments, the affinity label is biotin. In certain embodiments, the 3' blocked stem-loop oligonucleotides are linked to a solid support. In certain embodiments, the 3' blocked stem-loop oligonucleotides are separated from the 3' extended nucleic acid strands by denaturation and purification.

In another aspect, the invention provides methods of forming a closed nucleic acid structure comprising a target nucleic acid, comprising: (a) providing a denatured target nucleic acid, at least one strand of the denatured target nucleic acid having a 5' phosphate group, a 5' segment, and a 3' segment; (b) contacting the strand of the denatured target nucleic acid with a 3' blocked stem-loop oligonucleotide having a 5' segment, a 3' segment, and an intervening segment that links the 5' and 3' segments, the 3' segment being complementary to the 3' segment of the denatured target nucleic acid strand, the 5' segment having a sequence capable of forming a stem-loop structure, and the intervening segment having a common sequence with the 5' segment of the denatured target nucleic acid strand; (c) annealing the 3' segment of the 3' blocked stem-loop oligonucleotide to the 3' segment of the denatured target nucleic acid strand, whereby the oligonucleotide provides a template for extension of the denatured target nucleic acid strand; (d) extending the denatured target nucleic acid strand to form a 3' extended nucleic acid strand having from 5'-3' a 5' phosphate group, the target nucleic acid strand, a 3' extension complementary to the 5' and intervening segments of the 3' blocked stem-loop oligonucleotide, and a 3' hydroxyl group; (e) separating the 3' blocked stem-loop oligonucleotide from the 3' extended nucleic acid strand; (f) allowing intramolecular hybridization of the 3' extended nucleic acid strand; thereby forming a nicked intermediate wherein a portion of the 3' extension has a stem-loop structure and another portion of the 3' extension is hybridized to the 5' segment of the target nucleic acid strand such that the 5' phosphate and 3' hydroxyl groups of the extended nucleic acid strand are separated by a nick; and (g) providing a ligase that seals the nick, thereby forming a closed nucleic acid structure including the strand of target nucleic acid circularized by a stem-loop structure.

In certain embodiments, the 3' blocked stem-loop oligonucleotide contains deoxyribo-uracil and is separated from the extended target nucleic acid strand by digestion with a uracil DNA glycosidase (UNG) and an endonuclease. In certain embodiments, the 3' blocked stem-loop oligonucleotide comprises an affinity label. In certain embodiments, the affinity label is biotin. In certain embodiments, the 3' blocked stem-loop oligonucleotide is linked to a solid support. In certain embodiments, the 3' blocked stem-loop oligonucleotide is separated from the 3' extended nucleic acid strand by denaturation and purification.

In another aspect, the invention provides methods of forming a closed nucleic acid structure comprising a target nucleic acid, comprising: (a) providing a denatured target nucleic acid, each strand of the denatured target nucleic acid having a 5' phosphate and a 3' segment; (b) contacting the strands of the denatured target nucleic acid with a pair of 3' blocked oligonucleotides, each oligonucleotide having a 3' segment and a 5' segment, the 3' segments being complementary to the 3' segments of the strands of the denatured target nucleic acid; (c) annealing the 3' segments of the 3' blocked oligonucleotides to the 3' segments of the denatured target nucleic acid strands, whereby each 3' blocked oligonucleotide provides a template for extension of the denatured target nucleic acid strand to which it is annealed; (d) extending the denatured target nucleic acid strands to form 3' extended nucleic acid strands, each 3' extended nucleic acid strand having from 5'-3' a 5' phosphate group, a strand of the target nucleic acid, a 3' extension complementary to the 5' segment of a 3' blocked oligonucleotide, and a 3' hydroxyl group; (e) contacting a duplex nucleic acid intermediate formed by annealing of the 3' extended nucleic acid strands to one another with a pair of stem-loop adaptors, each adaptor having a 3' segment and a 5' segment, the 5' segments each having a 5' phosphate group and a sequence capable of forming a stem-loop structure and the 3' segments being complementary to the 3' extensions of the duplex nucleic acid intermediate and ending in a 3' hydroxyl group; (f) annealing the 3' segments of the stem-loop adaptors to the 3' extensions of the duplex target nucleic acid; and (g) providing a ligase that seals nicks between the ends of the stem-loop adaptors and the ends of duplex target nucleic acid, thereby forming a closed nucleic acid structure including the two strands of the target nucleic acid joined to one another by stem-loop structures.

In certain embodiments, following step (d), the method comprises: (i) separating the 3' blocked oligonucleotides from the 3' extended nucleic acid strands; and (ii) allowing intermolecular hybridization between the 3' extended nucleic acid strands; thereby forming a duplex nucleic acid intermediate having at each end a 5' phosphate group and a single-stranded 3' extension ending in a 3' hydroxyl group, wherein the 3' extensions are complementary to the 5' segments of the 3' blocked oligonucleotides.

In certain embodiments, the 3' blocked oligonucleotides contain deoxyribo-uracil and are separated from the extended target nucleic acid strands by digestion with a uracil DNA glycosidase (UNG) and an endonuclease. In certain embodiments, the 3' blocked oligonucleotides comprise an affinity label. In certain embodiments, the affinity label is biotin. In certain embodiments, the 3' blocked oligonucleotides are linked to a solid support. In certain embodiments, the 3' blocked oligonucleotides are separated from the extended nucleic acid strands by denaturation and purification. In certain embodiments, the 5' and 3' segments of the stem-loop adaptors are linked by a segment consisting of 0 to 4 thymine nucleobase units.

In another aspect, the invention provides methods of forming a closed nucleic acid structure comprising a target nucleic acid, comprising: (a) providing a denatured target nucleic acid, at least one strand of the denatured target nucleic acid having a 5' phosphate, a 5' segment, and a 3' segment; (b) contacting the strand of the denatured target nucleic acid with a 3' blocked oligonucleotide having a 5' segment, a 3' segment, and an intervening segment that links the 5' and 3' segments, the 3' segment being complementary to the 3' end segment of the denatured target nucleic acid strand and the intervening segment having a common sequence with the 5' segment of the denatured target nucleic acid strand; (c) annealing the 3' segment of the 3' blocked oligonucleotide to the 3' segment of the denatured target nucleic acid strand, whereby the 3' blocked oligonucleotide provides a template for extension of the denatured target nucleic acid strand; (d) extending the denatured target nucleic acid strand to form a 3' extended nucleic acid strand having from 5'-3' a 5' phosphate group, the target nucleic acid strand, a 3' extension complementary to the 5' and intervening segments of the 3' blocked oligonucleotide, and a 3' hydroxyl group; (e) separating the 3' blocked oligonucleotide from the 3' extended nucleic acid strand; (f) contacting the 3' extended nucleic acid with a stem-loop adaptor having a 3' segment and a 5' segment, the 5' segment having a 5' phosphate group and a sequence capable of forming a stem-loop structure and the 3' segment having a common sequence with the 3' segment of the 3' blocked oligonucleotide and ending in a 3' hydroxyl group; (g) allowing the 3' extended nucleic acid strand to intermolecularly hybridize with the stem-loop adaptor and intramolecularly hybridize with itself; thereby forming a nicked intermediate wherein the 3' extended nucleic acid strand has a stem-loop structure, the 5' phosphate group of the 3' extended nucleic acid strand is separated from the 3' hydroxyl group of the stem-loop adaptor by a nick, and the 5' phosphate group of the stem-loop adaptor is separated from the 3' hydroxyl group of the 3' extended nucleic acid strand by a nick; and (h) providing a ligase that seals nicks between the ends of the stem-loop adaptor and the ends of the 3' extended nucleic acid, thereby forming a closed nucleic acid structure including the strand of the target nucleic acid circularized by a stem-loop structure.

In certain embodiments, the 3' blocked oligonucleotide contains deoxyribo-uracil and is separated from the extended target nucleic acid strand by digestion with a uracil DNA glycosidase (UNG) and an endonuclease. In certain embodiments, the 3' blocked oligonucleotide comprises an affinity label. In certain embodiments, the affinity label is biotin. In certain embodiments, the 3' blocked oligonucleotide is linked to a solid support. In certain embodiments, the 3' blocked oligonucleotide is separated from the 3' extended nucleic acid strand by denaturation and purification.

In another aspect, the invention provides methods of forming a closed nucleic acid structure comprising a target nucleic acid, comprising: (a) providing a denatured target nucleic acid, each strand of the denatured target nucleic acid having a 3' segment and at least one strand of the denatured target nucleic acid having a 5' phosphate; (b) contacting the strands of the denatured target nucleic acid with a pair of 3' blocked oligonucleotides, each oligonucleotide of the pair having 5' and 3' segments, the 3' segments of the oligonucleotides being complementary to the 3' segments of the target nucleic acid strands and the 5' segments of the oligonucleotides being complementary in opposing orientations, wherein a first oligonucleotide of the pair further comprises an additional intervening segment linking the 5' and 3' segments; (c) annealing the 3' segments of the oligonucleotides to the 3' segments of the target nucleic acid strands, whereby each 3' blocked oligonucleotide provides a template for extension of the target nucleic acid strand to which it is annealed; (d) extending the target nucleic acid strands to form 3' extended target nucleic acid strands, a first 3' extended target nucleic acid strand comprising from 5'-3' a 5' phosphate group, a strand of the target nucleic acid, a 3' extension complementary to the 5' and intervening segments of the first oligonucleotide, and a 3' hydroxyl group, a second 3' extended target nucleic acid strand comprising from 5'-3' a complement strand of the target nucleic acid, a 3' extension complementary to the 5' segment of the second oligonucleotide, and a 3' hydroxyl group; (e) separating the 3' blocked oligonucleotides from the 3' extended target nucleic acid strands; (f) allowing intermolecular hybridization between the 3' extended target nucleic acid strands; thereby forming a duplex target nucleic acid having 3' extensions, wherein the segments of the 3' extensions complementary to the 5' segments of the first and second oligonucleotides are hybridized to one another, creating a circularized nucleic acid intermediate having a nicked duplex segment and a single-stranded segment complementary to the intervening segment of the first oligonucleotide, wherein the nick in the duplex segment separates the 5' phosphate and 3' hydroxyl groups of the first 3' extended target nucleic acid strand; and (g) providing a ligase that seals the nick in the circularized nucleic acid intermediate; thereby forming a closed nucleic acid structure comprising a single-stranded segment and a duplex segment, wherein the duplex segment includes the target nucleic acid.

In certain embodiments, the 3' blocked oligonucleotides contain deoxyribo-uracil and are separated from the 3' extended target nucleic acid strands by digestion with a uracil DNA glycosidase (UNG) and an endonuclease. In certain embodiments, the 3' blocked oligonucleotides comprise an affinity label. In certain embodiments, the affinity label is biotin. In certain embodiments, the 3' blocked oligonucleotides are linked to a solid support. In certain embodiments, the 3' blocked oligonucleotides are separated from the extended target nucleic acid strands by denaturation and purification. In certain embodiments, providing a denatured target nucleic acid comprises contacting a target nucleic acid with an amplification primer pair under PCR conditions, each of the amplification primers having a 3' target-binding segment. In certain embodiments, one or both of the amplification primers has a 5' phosphate group. In certain embodiments, the intervening segment of the first 3' blocked oligonucleotide is four nucleobase units in length.

In another aspect, the invention provides methods of forming a closed nucleic acid structure comprising a target nucleic acid, comprising: (a) providing a denatured target nucleic acid; (b) contacting the strands of the denatured target nucleic acid with a pair of primers and a pair of 3' blocked oligonucleotides under PCR conditions, each primer having a 5' phosphate group and a 3' target-binding segment and each 3' blocked oligonucleotide having a 5' segment and a 3' target-binding segment, wherein the 3' target-binding segments of the oligonucleotides are complementary to 3' end segments of an amplicon produced by the primer pair; thereby forming a 3' extended target nucleic acid duplex, each strand of the duplex comprising a 5' phosphate group, a segment of the target nucleic acid, a 3' extension complementary to the 5' segment of a 3' blocked oligonucleotide, and a 3' hydroxyl group; (c) contacting the 3' extended target nucleic acid duplex with a pair of stem-loop adaptors, each of the adaptors having a 3' segment and a 5' segment, the 5' segments each having a 5' phosphate group and a stem-loop structure and the 3' segments each ending in a 3' hydroxyl group and being complementary to a 3' extensions of a strand of the 3' extended nucleic acid duplex; (d) annealing the 3' segments of the stem-loop adaptors to the 3' extensions of the 3' extended target nucleic acid duplex; and (e) providing a ligase that seals nicks between the ends of the primers and the ends of the 3' extended target nucleic acid duplex, thereby forming a closed nucleic acid structure including a double-stranded segment of the target nucleic acid wherein the strands are joined to one another by stem-loop structures.

The target nucleic acid in any of the foregoing methods can be a genomic DNA molecule. Alternatively, the target nucleic acid can be a cDNA molecule. In some embodiments of any of the foregoing methods, the target nucleic acid is a RNA molecule. In other embodiments, the target nucleic acid is a PCR product.

In certain embodiments of any of the foregoing methods, the ligase is a DNA ligase. In certain embodiments, the ligase is a T4 DNA ligase.

In certain embodiments of any of the foregoing methods, each of the primers has a 5' segment of at least 5 nucleobase units. In certain embodiments, each of the primers has a 3' segment of at least 10 nucleobase units.

DEFINITIONS

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobases. Nucleobases can be conventional DNA or RNA bases (A, G, C, T, U), base analogs, e.g., inosine, 5-nitroindazole and others (The Biochemistry of the Nucleic Acids 5-36, Adams et al., ed., 11.sup.th ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxyguanosine, 4-ethyl-2'-deoxycytidine (Nguyen et al., 1998, Nucl. Acids Res. 26(18):4249-58), 4,6-difluorobenzimidazole and 2,4-difluorobenzene nucleoside analogues (Kiopffer & Engels, 2005, Nucleosides Nucleotides Nucl. Acids, 24(5-7) 651-4), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, and O-4-alkyl-pyrimidines (U.S. Pat. No. 5,378,825; PCT No. WO 93/13121; Gamper et al., 2004, Biochem. 43(31): 10224-36), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.).

A nucleobase attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units.

A canonical nucleobase unit refers to the four types of nucleobase units commonly found in natural DNA or RNA or their corresponding triphosphates. In DNA, the four canonical nucleobase units are deoxyribo-adenine, cytosine, guanine, and thymine. In RNA, the four canonical nucleobase units are ribo-adenine, cytosine, guanine or uracil. If a nucleic acid is referred to generically (i.e., including DNA and RNA), the four canonical nucleobase units are adenine, cytosine, guanine and thymine/uracil. Thymine/uracil means thymine in the context of a DNA molecule and uracil in the context of an RNA molecule.

A non-canonical nucleobase unit is a nucleobase unit other than a canonical nucleobase unit. Unless otherwise indicated, non-canonical nucleobase unit should support template-directed incorporation of a complementary nucleobase unit, which can be canonical or non-canonical. Examples of non-canonical nucleobase units include methylated nucleobase units, which refer to nucleobase units that carry a methyl group attached to a position of a nucleobase unit, typically on the nucleobase, that is accessible for methylation. Examples of methylated nucleobase units include methyl dCTP, methyl dGTP, methyl dATP and methyl dTTP.

Other non-canonical nucleobase units include reversibly modified nucleobase units. A reversibly modified nucleobase unit includes nucleobase units that are modified to inhibit polymerase based nucleic acid extension. Examples of suitable reversibly modified nucleobase units include nucleotides with hydrolysis resistant modifications at the 2' carbon atom, nucleotides with O-linked triisopropylsilyl groups at the 2' carbon atom, nucleotides with O-linked tertButyl-dimethylsilyl groups at the 2' carbon atom, nucleotides with O-linked alkyl groups at the 2' carbon atom, and an A, C, T/U, or G nucleotide with a —$OSiC_6$ group at the 2' carbon atom (Glen Research, USA). The modification groups are removed from the reversibly modified nucleobase units using well known chemistries and methods. For example, when the modification is the O-linked tertButyl-dimethylsilyl groups at the 2' carbon atom, this group can be removed from the nucleobase unit using tetrabutylammonium fluoride (TBAF) in 1M Tetrahydrofuran (THF).

A non-canonical nucleobase unit pair refers to a pair of non-canonical nucleobase units that base pairs with each other but do not base pair or base pair less strongly with canonical nucleobase units A, C, G, and T/U. Examples of non-canonical nucleobase unit pairs include isocytosine (isoC) and isoguanine (isoG) (U.S. Pat. Nos. 5,432,272, 6,001,983, 6,037,120, 6,104,0496, 6,617,106, 6,977,161; U.S. Patent Application Nos. 20040106108, 20060078936; EP1358352, EP1590482, WO0233126 and WO04065550), 5-methylisocytosine and isoguanine; Im-$N^O$ and Im-$O^N$; A* and T*; and 8-oxoG and adenine. Other non-canonical nucleobase unit pairs include, for example, 2,4-diamino-5-(β-D-2'-deoxyribofuranosyl)pyrimidine (dκ) and deoxyxanthosine triphosphate (dX) (Horlacher et al. PNAS USA 1995; 92:6329-6333; Piccirilli et al. Nature 1990; 343:33-37); 2,4-diaminopyrimidine (pyDAD) and xanthine (puADA) (Sismour et al. Nucleic Acids Res. 2004; 32:728-735). Some non-canonical bases may require the use of modified polymerase to facilitate their efficient incorporation into amplicons.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; WO 95/32305), and a locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and non-conventional components (e.g., conventional RNA bases with 2'-O-methyl linkages, or a mixture of canonical and non-canonical nucleobase units). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) can be used to influence the stability of duplexes formed by nucleic acids.

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A "primer" is an oligonucleotide, typically between about 10 to 100 nucleotides in length, capable of selectively binding to a specified nucleic acid or "template" by hybridizing with the template. The primer provides a point of initiation for polymerase-mediated template-directed synthesis of a nucleic acid complementary to the template. Primers hybridizing to opposing strands of a double-stranded sequence are referred to as forward and reverse primers.

An oligonucleotide primer used to initiate a sequencing reaction is referred to as a sequencing primer.

A "copy" of a particular nucleic acid segment, such as generated by multiple passes around a closed template, can mean an exact copy or a substantially similar copy (e.g., greater than 80% sequence identity) due to occasional sequencing errors, such as misincorporation of noncomplementary nucleobase(s) or misidentification of incorporated nucleobase(s).

A "segment" of a nucleic acid means the entire nucleic acid or a contiguous portion thereof. A segment of nucleic acid can be, for example, short in length (e.g., about 2 to about 10 nucleobase units), intermediate in length (e.g., about 10 to about 1000 nucleobase units), or long in length (e.g., about 1000 nucleobase units to about 10,000 nucleobase units, or longer). An "end segment" is a segment of a nucleic acid that includes a 5'-most or 3'-most nucleobase unit of the nucleic acid.

A pair of "immediately adjacent" segments have no intervening segment. A segment that is immediately adjacent to a segment at the end of a nucleic acid strand can be described as "internal to" the end segment. If the end segment is located at the 3' end of the nucleic acid strand, a segment internal to the 3' end segment is located 5' to the 3' end segment. Conversely, if the end segment is located at the 5' end of the nucleic acid strand, a segment internal to the 5' end segment is located 3' to the 5' end segment.

A "common sequence" between a pair of nucleic acid segments, such as two oligonucleotide segments or an oligonucleotide segment and a segment of a target nucleic acid, refers to a pair of nucleic acid segments having substantially homologous nucleic acid sequences. Typically, a pair of nucleic acid segments that share a common sequence have at least 70%, 75%, 80%, 85%, 90%, 95%, or more sequence identity. It is understood here that the recited ranges include all whole and all partial numbers there in.

A "defined end" of a nucleic acid means the identity of at least some nucleobase units at the end is known. For example, depending on the method, knowledge of the identity of at least 5, 6, 7, 8, 9, 10, 11, 12, 13, 14, 15, or more nucleobase units from each end of the nucleic acid including the terminal nucleotide is typically sufficient. If the nucleic acid having defined ends is double-stranded, the nucleic acid typically has blunt ends, although such is not necessary.

A closed nucleic acid structure is one in which at least one strand has no terminal end, no nicks and no gaps (sometimes referred to as continuous strand). A nick refers to a discontinuity in a double stranded nucleic acid molecule where there is no phosphodiester bond between adjacent nucleotides of one strand and a gap refers to a discontinuity in a double stranded nucleic acid molecule where a space of 1 or more nucleotides exists between otherwise adjacent segments of one strand. In some closed double-stranded nucleic acids, one strand has no terminal end, no nicks and no gaps, and the other strand has a nick or gap. In some topographically circular templates, the 5' and 3' ends of a single-stranded nucleic acid are held in proximity to one another by duplexing the ends of the single stranded nucleic acid to a complementary nucleic acid (sometimes referred to as a "bridging oligo") to result in a nicked or gapped strand. A closed nucleic acid can have one or two contiguous strands. Exemplary closed nucleic acid structures include single-stranded circular nucleic acids, double-stranded circular nucleic acids, dumbbell-shaped nucleic acids, such as SMRTbell templates, and other continuous structures containing stem-loops or pad-locks (See e.g., M. Nilsson et. al., "Padlock Probes: Circularizing Oligonucleotides for Localized DNA Detection," Science 265: 2085-88 (1994); Pickering et al. in Nucleic Acids Research, 2002, vol. 30, e60, U.S. Pat. No. 5,854,033; U.S. Pat. No. 5,912,124; U.S. Pat. No. 6,235,472, WO 02/068683, WO 01/06012, WO 0077260, WO 01/57256).

DETAILED DESCRIPTION

I. General

The invention provides methods of generating closed nucleic acid structures including a target segment of a target molecule suitable for various detection, amplification and sequencing methods. A closed nucleic acid is one in which one or both strands are continuous and includes, for example, a single stranded continuous nucleic acid strand, a double stranded structure in which both strands are in a continuous strand configuration, a double-stranded circular molecule in which one strand has a nick or gap, or a SMRT® bell template. The target segment within a closed structure can be defined using a pair of primers used in PCR amplification of a target molecule. The target segment can also be defined using a blocker oligonucleotide, an extension blocker, or equivalents thereof. The target segment can further be defined using fragmentation methods such as enzymatic cleavage. Alternatively, target nucleic acids (e.g., mRNA, rRNA) can already have the range of sizes suitable for downstream amplification or sequencing, and can be used directly in the present methods without defining a smaller target segment. FIGS. 1-23 show methods 1-23 for making such closed nucleic acid structures, as further described below.

II. Primers, Adapters, Blockers, Extenders, Exonucleases, Polymerases, Terminal Deoxynucleotidyl Transferases This section describes different types of primers and other oligonucleotide structures used in making closed nucleic acid structures. Different methods use different primers or other oligonucleotide structures as described further below.

Linear Primers

A linear primer does not necessarily indicate that the primer is completely lacking in secondary structure, but indicates whatever secondary structure may be adopted by the primer is not critical to the use of the primer in the present methods. Accordingly, the methods can use, for example, a pair of forward and reverse linear primers hybridizing to opposing strands of a target nucleic acid (if the target nucleic acid is double-stranded) or to a target nucleic acid and its complementary strand (if the target nucleic acid is single-stranded). Linear primers typically include, in 5' to 3' direction, a 5' segment and a 3' segment. The 3' segments are typically target-binding segments complementary to a target nucleic acid, e.g., as is the case for conventional PCR primers. Often, the 5' segments are not complementary to the target nucleic acid, instead including a sequence that provides identifying and/or other information, e.g., such as a sequence tag. However, linear primers need not have functionally distinct 5' and 3' segments. For example, both the 5' and 3' segments can be complementary to adjacent segments on a target nucleic acid. Moreover, one linear primer in a pair can have functionally distinct 5' and 3' segments, whereas the other primer in the pair does not. Exemplary lengths for linear primers, as well as for each of the 5' and 3' segments, include at least 3, 5, 8, 9, 10, 11, 12, 13, 14, 15, 16, 17, 18, 19, or 20 nucleobases units and optionally up to 30, 35, 40, 45, 50, or more nucleobase units, including all permutations of upper and lower limits. The spacing of linear primers with respect to a target nucleic acid can be used to define a segment of the target nucleic acid that is amplified and available for sequencing.

For generating some forms of closed nucleic acid structures, a linear primer pair having complementary 5' segments in the first primer and the second primer can be used. The 5' segments are complementary to one another in opposing orientations to permit annealing of nucleic acids via the 5' segments. This means that the 5' segments have sufficient complementarity to permit annealing but does not preclude, for example, one 5' segment from having one (or more) extra segment(s) not represented in the other 5' segment. To illustrate, for 5' segments of the same length showing perfect complementarity to one another, a 5' segment of a first primer having the sequence of 5'-GCGCCG-3' (SEQ ID NO: 1) is complementary to the 5' segment of a second primer having the sequence of 5'-CGGCGC-3' (SEQ ID NO: 2).

For generating some forms of closed nucleic acid structures, a primer pair having non-complementary 5' segments in the first primer and the second primer is used. In such methods, additional oligonucleotides, such as adaptors, are used in conjunction with the primer pair to form the closed nucleic acid structures. For example, the 5' segments of the first and second primers can provide tags that provide specific binding sites for adaptors (e.g., stem-loop adaptors).

The 5' segments of the primers can have the same or different lengths. If the 5' segments of two or more primers are complementary and have different lengths, the longer 5' segment optimally includes a proximal 5' sub-segment and a distal 5' sub-segment, wherein the distal 5' sub-segment is complementary to the shorter 5' segment and the proximal 5' sub-segment is substantially non-complementary to the shorter 5' segment. The foregoing use of proximal and distal refers to the relative position of the 5' sub-segments to the 3' segment on the same primer. A double-stranded closed nucleic acid structure incorporating the foregoing primers (i.e., primers having complementary 5' segments of different length) typically has a gap between the 5' end of the shorter 5' segment and an adjacent 3' hydroxyl group. The width of this gap is the number of nucleobase units by which the 5' segments of the primers differ in length (e.g., the length of the proximal 5' subsegment). Such gaps can be useful, e.g., for initiating polymerization off of the closed nucleic acid structure in the absence of a sequencing primer. Accordingly, the width of the gap can be chosen depending on several considerations, including the preferences of a sequencing polymerase. The difference in length of the complementary 5' segments can be, e.g., at least 1, 2, 3, 4, 5, 6, 7, 8, 9, 10, 11, 12, or more nucleobase units, and optionally up to 15, 20, 25, or more nucleobase units, including all permutations of the lower and upper limits. Preferably, the 5' segment of the first primer is longer than the 5' segment of the second primer by four nucleobase units and the gap is four nucleobase units. Larger gaps for example ranging up to ¾ the length of the ungapped strand can also be made with exonuclease digestion after forming a nicked or gapped template. In some circular templates, the gap is ¼ to ¾ the length of the intact circularized strand.

Nucleic acids amplified using linear primers can be treated with a polynucleotide kinase (PNK, e.g., a T4 PNK) to transfer a phosphate group onto the 5'-end of the amplified nucleic acids. Alternatively, one or both of the primers in a pair can include a 5' phosphate group. When only one primer in a pair includes a 5' phosphate group, the primer that includes the 5' phosphate group can be arbitrarily referred to as the first primer; the other primer in the pair can be referred to as the second primer. If the 5' segments of the primers are complementary but of unequal length, the primer with the shorter 5' segment is typically referred to as the second primer. The second primer in a pair of primers having complementary 5' segments of unequal length typically does not need to have a 5' phosphate because the intention of using primers having 5' segments of unequal length is to leave a gap adjacent to the end of the shorter 5' segment. However, inclusion of a 5' phosphate at the 5' end of the second primer is still permissible because ligation of the closed nucleic acid structure does not close a gap.

Linear primers can include any of the canonical nucleobase units and/or one or more non-canonical nucleobase units, linked by conventional or non-conventional linkages. Preferred non-canonical nucleobase units for use in the foregoing linear primers include deoxyribo-uracil and nucleobase units that prevent extension, such as from a strand that is using the primer as a template. Non-canonical nucleobase units and/or non-conventional linkages can be incorporated anywhere in the linear primer, depending on the needs of a method in which the primers are used, including within a 3' or 5' segment of the primer, at a position between 5' and 3' segments, or dispersed throughout the primer.

Linear primers can also include an affinity label, such as biotin or avidin, and/or be bound to a solid substrate, such as glass, a polymeric surface, a microchip, a column, or a bead.

Stem-Loop Primers

Typically, a stem loop primer includes a 5' segment and a 3' segment. All or part of the 3' segment can be complementary to a nucleic acid to be amplified, such as a target nucleic acid. Alternatively, the 3' segment can be complementary to a tag present in another primer (e.g., the 5' segment of a linear primer used to amplify and/or define a segment of a target nucleic acid). The 5' segment typically includes a sequence capable of forming a stem-loop structure. For example, the 5' segment can include a first sub-segment and a second sub-segment joined by an intervening segment, wherein the first and second sub-segments are complementary in opposing orientation, and wherein the intervening segment is capable of bending back on itself to allow the first and second sub-segments to base-pair with one another and form a double-stranded duplex. The first and second sub-segments of the 5' segment can be located at the ends of the 5' segment. The 5' segment of a stem-loop primer can be linked to the 3' segment either directly or via one or more intervening nucleobase units. Exemplary lengths for the 3' segments of stem-loop primers are at least 3, 5, 8, 9, 10, 11, 12, 13, 14, 15, 16, 17, 18, 19, or 20 nucleobases units and optionally up to 30, 35, 40, 45, 50, or more nucleobase units, including all permutations of upper and lower limits. Exemplary lengths for the 5' segments of stem-loop primers are at least 12, 15, 20, or 25 nucleobase units and optionally up to 35, 40, 45, 50, 55, 60 or more nucleobase units, including all permutations of upper and lower limits.

The spacing of a pair of stem-loop primers with respect to a target nucleic acid can be used to define a segment of the target nucleic acid that is amplified and available for sequencing. In some methods, the 5' segments of the stem-loop primers are not complementary, thereby preventing a primer-extended nucleic acid duplex from circularizing intramolecularly via two overhanging 5' segments. Alternatively, the two stem-loop 5' segments of the primers can be complementary.

Stem-loop primer can include a 5' phosphate group located at their 5' end. Alternatively or in addition, stem-loop primers can include any of the canonical nucleobase units and/or one or more non-canonical nucleobase units, linked by conventional or non-conventional linkages. Preferred non-canonical nucleobase units for use in the foregoing stem-loop primers include deoxyribo-uracil. Non-canonical nucleobase units and/or non-conventional linkages can be incorporated anywhere in the stem-loop primer, depending on the needs of a method in which the primers are used, including at a position between 5' and 3' segments or dispersed throughout the primer.

Stem-loop primers can also include an affinity label, such as biotin or avidin, and/or be bound to a solid substrate, such as glass, a polymeric surface, a microchip, a column, or a bead.

Adapters

Adapters are not normally used as primers but may serve to provide, e.g., a structure that facilitates the formation of closed nucleic acid structures and/or a binding site for a sequencing primer. Preferred adaptors include a stem-loop structure and can be used, e.g., in combination with a linear primer pair. Typically, a stem loop primer includes a 5' segment and a 3' segment. Typically, all or part of the 3' segment is complementary to a segment of another primer, e.g., the 5' segment of a linear primer used to amplify and/or define a segment of a target nucleic acid. The 5' segment typically has a sequence capable of forming a stem-loop structure. Similar to stem-loop primers discussed above, the 5' segment can include a first sub-segment and a second sub-segment joined by an intervening segment, wherein the first and second sub-segments are complementary in opposing orientation, and wherein the intervening segment is capable of bending back on itself to allow the first and second sub-segments to base-pair with one another and form a double-stranded duplex. The first and second sub-segments of the 5' segment can be located at the ends of the 5' segment. As an alternative arrangement, and depending on the method in which the adaptors are used, the adaptors can include a 5' segment that is complementary to the segment of another primer and a 3' segment that includes a stem-loop structure. The 5' segment of an adaptor can be linked to the 3' segment either directly or via one or more intervening nucleobase units. The intervening nucleobase units can be, e.g., 1, 2, 3, 4, or more thymine nucleobase units or one or more deoxyribo-uracil nucleobase units.

Exemplary lengths for adaptor segments that do not form stem-loop structures (e.g., segments that are complementary to a segment of another primer) are at least 3, 5, 8, 9, 10, 11, 12, 13, 14, 15, 16, 17, 18, 19, or 20 nucleobase units and optionally up to 30, 35, 40, 45, 50, or more nucleobase units, including all permutations of upper and lower limits. Exemplary lengths for segments of adaptors that form a stem-loop structure are at least 12, 15, 20, or 25 nucleobases units and optionally up to 35, 40, 45, 50, 55, 60 or more nucleobase units, including all permutations of upper and lower limits.

For methods in which a pair of stem-loop adaptors are used, the 5' segment from the first adaptor in the pair and the 5' segment from the second adaptor can be the same or different. Moreover, the 3' segment of the first primer in the pair and the 3' segment from the second primer can be the same or different. Accordingly, when the adaptors are used in conjunction with a pair of primers, the primer segments complementary to the adapter segments are the same or different (or share a common sequence) based on whether the adaptor segments are the same or different. For example, in cases where the 3' segments of a pair of adaptors have different sequences, the 5' segments of a corresponding pair of primers are typically different.

Typically, oligonucleotide adaptors (e.g., stem-loop adaptors) include a 5' phosphate group at their 5' ends. In addition, as with linear and stem-loop primers, oligonucleotide adaptors can include any of the canonical nucleobase units and/or one or more non-canonical nucleobase units, linked by conventional or non-conventional linkages. Non-canonical nucleobase units and/or non-conventional linkages can be incorporated anywhere in the adaptor, depending on the needs of a method in which the adaptors are used, including at a position between 5' and 3' segments or dispersed throughout the adaptor. Adaptors can also include an affinity label, such as biotin or avidin, and/or be bound to a solid substrate, such as glass, a polymeric surface, a microchip, a column, or a bead.

Target Extension Oligonucleotides

Target extension oligonucleotides bind to the 3' end of a target nucleic acid strand and provide a template for extension of the strand. In doing so, target extension oligonucleotides allow addition of new segments, particularly sequence tags, to target nucleic acids. The extended target nucleic acids are useful intermediates for generating closed nucleic acid structures.

Target extension oligonucleotides include a 3' segment and a 5' segment. The 3' segment is complementary to the 3' end of a target nucleic acid, while the 5' segment typically includes a sequence that provides identifying and/or other information, e.g., such as a sequence tag. As used in some of the methods described herein, template extension oligonucleotides further include a nucleobase unit at their 3' end that prevents or blocks polymerase-based extension of the oligonucleotide after it hybridizes to the target nucleic acid. In such instances, the template extension oligonucleotide can be termed a "3' blocked oligonucleotide." Common examples of nucleobase units that block extension include nucleobase units modified at the ribose ring 3'-OH, which prevents addition of further bases to the '3-end of the oligonucleotide sequence by a polymerase. Such 3'-OH modifications are well known (see, e.g., Josefsen, M., et al., Molecular and Cellular Probes, 23 (2009):201-223; McKinzie, P. et al., Mutagenesis. 2006, 21(6):391-7; Parsons, B. et al., Methods Mol. Biol. 2005, 291:235-45; Parsons, B. et al., Nucleic Acids Res. 1992, 25:20(10):2493-6; and Morlan, J. et al., PLoS One 2009, 4 (2): e4584)). Another example of a blocking moiety includes the use of a nucleotide or a short nucleotide sequence having a 3'-to-5' orientation, so that there is no free hydroxyl group at the 3'-terminus of the oligonucleotide (see, e.g., Arnold et al., "Non-Nucleotide Linking Reagents for Nucleotide Probes," U.S. Pat. No. 6,031,091, the contents of which are hereby incorporated by reference herein). Reverse polarity (3'→5') phosphoramadites are often used at a terminal end of an oligonucleotide to create a 3'-3' linkage on the oligonucleotide. The inverted residue results in an oligonucleotide having two 5' ends, which blocks polymerase extension of the oligonucleotide. Reverse polarity phosphoramadites are available from numerous commercial vendors (e.g., Biosearch Technologies, Inc., U.S.A., Cat# BG1-1100I-1). Other examples of nucleobase units that block extension include nucleobase units modified at the ribose ring 2'-OH of the oligonucleotide, which also prevents extension of the oligonucleotide sequence by a polymerase. Such 2'-OH modifications are well known. Exemplary 2'-terminator nucleotides include a phosphate group, 2'-monophosphate-3'-hydroxyl-5'-triphosphate nucleosides, 2'-monophosphate-3'-hydroxyl-5'-diphosphate nucleosides, and 2'-terminator nucleotides described, e.g., in U.S. Patent Application Publication Nos. 20050037991 and 20050037398. Examples of additional non-extendible blocker nucleobase units include nucleobase units at the 3' end that are not complementary to the target sequence and therefore do not base-pair and cannot be enzymatically extended. Other known methods for making oligonucleotides non-extendible can also be used.

Exemplary lengths for the 3' segments of target extension/3' blocked oligonucleotides are at least 3, 5, 8, 9, 10, 11, 12, 13, 14, 15, 16, 17, 18, 19, or 20 nucleobases units and optionally up to 30, 35, 40, 45, 50, 60, 70, 80, 90, 100, 150, 200 or more nucleobase units, including all permutations of upper and lower limits. Exemplary lengths for the 5' segments of target extension/3' blocked oligonucleotides are at least 4, 5, 6, 7, 8, 9, 10, 11, or 12 nucleobase units and optionally up to 15, 20, 25, 30 or more nucleobase units, including all permutations of upper and lower limits.

Target extension/3' blocked oligonucleotides can include any of the canonical nucleobase units and/or one or more non-canonical nucleobase units, linked by conventional or non-conventional linkages. Preferred non-canonical nucleobase units for use in the foregoing target extension/3' blocked oligonucleotides include deoxyribo-uracil and any of the 3'-OH and 2'-OH modified nucleobase units described above. Non-canonical nucleobase units and/or non-conventional linkages can be incorporated anywhere in the target extension/3' blocked oligonucleotides, depending on the needs of a method in which the primers are used, including at the 3' end of the oligonucleotide or dispersed throughout the oligonucleotide.

Target extension/3' blocked oligonucleotides can have various primer structures, such as linear primers or stem-loop primers. In addition, target extension/3' blocked oligonucleotides can also include an affinity label, such as biotin or avidin, and/or be bound to a solid substrate, such as glass, a polymeric surface, a microchip, a column, or a bead.

Blocker Oligonucleotides

A blocker oligonucleotide is an oligonucleotide that hybridizes to a region of a target nucleic acid located 5' with respect to a region of the target nucleic acid that hybridizes to a primer. The blocker oligonucleotide is used in conjunction with the primer and hybridizes to the target nucleic acid with sufficient affinity to prevent displacement of the blocker oligonucleotide during the formation of a DNA extension product from the primer. The blocker oligonucleotide may be provided to a pre-amplification/pre-extension reaction mixture (i.e., reaction mixture that does not include the enzymes necessary for an amplification/extension reaction) and/or an amplification/extension reaction mixture (i.e., reaction mixture that includes the enzymes necessary for an amplification/extension reaction). Typically, the blocker oligonucleotide is added to the reaction mixture at about the same concentration as the primer. Exemplary lengths for blocker oligonucleotides are at least 4, 5, 6, 7, 8, 9, 10, 11, or 12 nucleobase units and optionally up to 15, 20, 25, 30 or more nucleobase units, including all permutations of upper and lower limits.

Blocker oligonucleotides may include non-canonical nucleobase units and/or non-conventional linkages which result in the blocking oligonucleotide having high affinity for the targeted region (i.e., greater affinity for the targeted region than a correspondingly unmodified oligonucleotide). Non-canonical nucleobase units and/or non-conventional linkages suitable for incorporation into blocker oligonucleotides include, but are not limited to, LNAs and 2'-0-Me nucleobase units. Because of their high affinity for target nucleic acid, when contacted by the advancing portion of a polymerase (e.g., a DNA polymerase), blocking oligonucleotides halt strand extension by the polymerase.

Typically, blocker oligonucleotides are non-extendible in the presence of a DNA polymerase, and thus are designed to prevent the initiation of DNA synthesis therefrom, e.g., by inclusion of a nucleobase unit at their 3' end that prevents polymerase-based extension from the oligonucleotide. Any of the strategies described in connection with 3' blocked oligonucleotides (see above) are suitable for preventing polymerase-based extension from the blocking oligonucleotides, including incorporating at the 3' end of the blocked oligonucleotide a 3'-OH or 2'-OH modified nucleobase units or a nucleobase unit that is non-complementary to the target sequence and therefore does not base-pair and cannot be enzymatically extended. Other methods known for making oligonucleotides non-extendible can also be used.

Extension Blocking Primers

An extension blocking primer refers to a primer that, under certain conditions, blocks extension by a nucleic acid polymerase when the primer is serving as a template for extension of a complementary strand. Extension blocking primers can include an extension blockers, such as a non-canonical nucleobase units from a non-canonical nucleobase unit pair. Preferably, the non-canonical nucleobase unit base pairs with another non-canonical nucleobase unit but does not base pair, or base pairs less strongly, with a canonical nucleobase unit (i.e., A, C, G, and T/U). Examples of suitable non-canonical nucleobase units include isoC and isoG, 5-methylisocytosine and isoguanine, Im-NO and Im-ON, A* and T*, 8-oxoG, 2,4-diamino-5-(β-D-2'-deoxyribofuranosyl)pyrimidine (dκ) and deoxyxanthosine triphosphate (dX), and 2,4-diaminopyrimidine (pyDAD) and xanthine (puADA). Further examples of extension blockers include modified nucleobase units that terminate polymerase dependent nucleic acid extension. Preferably the modified nucleobase units are reversibly modified so that upon reversal of the modification the resulting nucleotide does not terminate polymerase dependent nucleic acid extension. Examples of suitable reversibly modified nucleobase units include nucleotides with hydrolysis resistant modifications at the 2' carbon atom, nucleotides with O-linked triisopropylsilyl groups at the 2' carbon atom, nucleotides with O-linked tertButyl-dimethylsilyl groups at the 2' carbon atom; nucleotides with O-linked alkyl groups at the 2' carbon atom, and an A, C, T/U, or G nucleotide with a —$OSiC_6$ group at the 2' carbon atom. (See e.g., US Pub. No. 2007/0082343). Extension blocking primers can also include ribonucleotide units that terminate nucleic acid extension by DNA dependent DNA polymerase. Termination of nucleic acid extension by such ribonucleotide units can be reversed by the addition of an RNA dependent DNA polymerase. In some methods, the extension blocking primer blocks extension by a nucleic acid polymerase when the 5' segment of the primer is serving as a template and a nucleobase unit needed to base pair with an extension blocker is not present in the reaction mixture. In some methods, extension is not blocked by the extension blocking primer when all the partnering nucleobase units that base pair with the extension blocking primer, including the extension blocker, are present in the reaction mixture. In other methods, the extension blocking primer blocks extension by a nucleic acid polymerase in a reaction mixture when the 5' segment of the primer is serving as a template and an extension blocker, such as a modified nucleobase unit, inhibits the extension activity of the polymerase. In some methods, extension in the reaction mixture is not blocked by a modified nucleobase unit when the modification is reversed to allow extension by a polymerase. In other methods, the extension blocking primer blocks nucleic acid extension in a reaction mixture when the primer comprises one or more ribonucleotides and the polymerase is a DNA dependent DNA polymerase; and extension is not blocked by the addition of an RNA dependent DNA polymerase.

Extension blocking primers typically include a 3' segment and a 5' segment. The 3' segment is typically complementary to a target nucleic acid, while the 5' segment typically includes one or more extension blocking nucleobase units, as described above. The 5' segment can further include one or more nucleobase units that are not extension blocking nucleobase units (e.g., canonical nucleobase units). Exemplary lengths for the 3' segments of extension blocking primers are at least 3, 5, 8, 9, 10, 11, 12, 13, 14, 15, 16, 17, 18, 19, or 20 nucleobases units and optionally up to 30, 35, 40, 45, 50, or more nucleobase units, including all permutations of upper and lower limits. Exemplary lengths for the 5' segments of extension blocking primers are at least 2, 3, 4, 5, 6, 7, 8, 9, or 10 nucleobase units and optionally up to 15, 20, 25, 30 or more nucleobase units, including all permutations of upper and lower limits.

Extension blocking primers can have various primer structures, such as linear primers or stem-loop primers. In addition, extension blocking primers can include an affinity label, such as biotin or avidin, and/or be bound to a solid substrate, such as glass, a polymeric surface, a microchip, a column, or a bead.

Extension blocking primers can be used in a limited-cycle amplification reaction wherein the extension blocking primers are useful for adding a single stranded 5' overhang to a duplex amplification product. An example of how a limited-cycle amplification method is used includes a two-step reaction wherein a first nucleic acid amplification reaction is performed in step 1 to generate amplification product and then a limited-cycle amplification reaction is performed in step 2 to incorporate a 5' overhang. The first amplification reaction is performed in the absence of extension blocking primers. The amplification product generated during this first nucleic acid amplification is then amplified in a limited-cycle, preferably a single cycle, using extension blocking primers as described above, thereby adding the 5' segment of the primer to the second round amplification product as a single stranded overhang. Alternatively in another example of how an extension blocking primer is used includes a one-step reaction wherein an amplification reaction is performed to generate amplification product and to incorporate a 5' overhang. In the one-step reaction, the extension blocking primers are used. Amplification products are generated wherein the amplification products have single stranded overhangs at the 5' end(s). These exemplary amplification methods are provided to illustrate the use of extension blocking primers with the instant invention, but the breadth of use for these extension blocking primers is not limited to these descriptions.

Duplex Primers

In some cases, a primer having a duplex region flanked by a first overhanging 3' segment in a first strand and a second overhanging 3' segment in an opposing strand can be used. When this type of primers is used, it is not necessary to use a pair of primers, i.e., a single primer for one strand of the target nucleic acids is sufficient for generating desired closed nucleic acid structures.

The first strand has a 5' phosphorylated 5' segment and an overhanging 3' segment which is the target-binding segment for one strand of the target nucleic acid. The second strand also has a 3' segment and a 5' segment, the 5' segment of the second strand being complementary to the 5' segment of the first strand. Two 5' segments hybridize to each other forming a duplex region under annealing conditions. The 3' segment of the second strand is designed to be complementary to the 3' end region of a primer-extended nucleic acid extended from the first strand of the primer.

Preferably, a primer comprising a first strand and a second strand in a duplex form is provided to a reaction mixture for primer extension. However, particularly in cases where a single strand template is used (i.e., without an opposing strand), the first strand and the second strand of the primer can be provided to a reaction mixture in an uncomplexed form as single strand primers. For example, the second strand can be provided before or after the first strand is extended to form a primer-extended nucleic acid, i.e., extension of the uncomplexed first strand can be initiated prior to or after the second strand is provided to a reaction mixture.

When a double-stranded template is used, a primer in a duplex form is preferably provided for primer extension. The duplex primer servers as the primer for both strands of the template, e.g., the 3' segment of the first strand binds to one strand of the target nucleic acid whereas the 3' segment of the second strand binds to the opposing strand of the target nucleic acid. Optionally, the first strand and the second strand can be provided to a reaction mixture as a mixture of single strand primers (e.g., one forward primer and one reverse primer). After the primer extension, additional second strand primers are then annealed to a primer-extended nucleic acid by the first strand, and additional first strand primers are annealed to a primer-extended nucleic acid by the second strand, thereby circularizing the primer-extended nucleic acids.

Optionally, duplex primers include an extension blocker. In some methods, the primer has a duplex region flanked by a first overhanging 3' segment in a first strand and a second overhanging 3' segment in an opposing strand, the first overhanging 3' segment being target-binding segment. The first strand having a 5' phosphate group, and the first 3'→5' nucleobase unit in the 5' segment is an extension blocker.

Non-Extendible Blockers

A non-extendible blocker is an oligonucleotide that hybridizes to a region of a nucleic acid in close proximity to the 3'-end of the target segment in a target nucleic acid. The blocker oligonucleotide may be from 3 to 10, 5 to 15, 12 to 24, 14 to 24, or 16 to 20, 20-50, 50-100, 100-200 or longer bases in length. The blocker oligonucleotide may be provided to a pre-amplification/pre-extension reaction mixture (i.e., reaction mixture that does not include the enzymes necessary for an amplification/extension reaction) and/or an amplification/extension reaction mixture (i.e., reaction mixture that includes the enzymes necessary for an amplification/extension reaction), preferably at about the same concentration as a primer. A blocker oligonucleotide hybridizes to a target nucleic acid with sufficient affinity to prevent displacement of the blocker oligonucleotide during the formation of a DNA extension product from a primer.

Non-extendible blocker oligonucleotides should not be extendible in the presence of a DNA polymerase, and may be modified to prevent the initiation of DNA synthesis therefrom (e.g., blocking moiety situated at the 3'-terminus). Common examples of blocker moieties include modifications of the ribose ring 3'-OH of the oligonucleotide, which prevents addition of further bases to the '3-end of the oligonucleotide sequence a polymerase. Such 3'-OH modifications are well known (see, e.g., Josefsen, M., et al., Molecular and Cellular Probes, 23 (2009):201-223; McKinzie, P. et al., Mutagenesis. 2006, 21(6):391-7; Parsons, B. et al., Methods Mol Biol. 2005, 291:235-45; Parsons, B. et al., Nucleic Acids Res. 1992, 25:20(10):2493-6; and Morlan, J. et al., PLoS One 2009, 4 (2): e4584, the disclosures of which are incorporated herein by reference in their entireties). Examples of blocker moieties also include modifications of the ribose ring 2'-OH of the oligonucleotide, which prevents extension of the oligonucleotide sequence a polymerase. Such 2'-OH modifications are well known. Exemplary 2'-terminator nucleotides include a phosphate group, 2'-monophosphate-3'-hydroxyl-5'-triphosphate nucleosides, 2'-monophosphate-3'-hydroxyl-5'-diphosphate nucleosides, and 2'-terminator nucleotides described, e.g., in U.S. Patent Application Publication Nos. 20050037991 and 20050037398. Blocker oligonucleotides may include nucleotide analogs which exhibit high affinity for the targeted region (i.e., greater affinity for the targeted region than the unmodified forms of the nucleotides) and which prevent extension of the blocker oligonucleotides in the presence of a DNA polymerase (e.g., LNAs or 2'-0-Me). Examples of non-extendible blocker further include oligonucleotides that are made non-extendible by adding bases to the 3' end that are not complementary to the target sequence and therefore do not base-pair and cannot be enzymatically extended.

Preferred non-extendible blocker oligonucleotides include those comprising reverse polarity nucleotide analogs at the 3' end of the non-extendible blocker oligonucleotides, i.e., nucleotides wherein the deoxyribose sugar-nitrogenous base backbone comprises certain nucleotides attached such that they are in opposite polarity as compared to the adjacent nucleotides (see, e.g., U.S. Pat. Nos. 5,399,676; 5,527,899 and 5,721,218 and Koga et al., J. Org. Chem. 56(12):3757-3759, 1991; Koga et al., Nucl. Acids Symp. Series 29:3-4, 1993; Koga et al., J. Org. Chem. 60:1520-1530, 1995). The non-extendible blocker oligonucleotides can comprise about 1 to about 50 reverse polarity nucleotide analogs at the 3' end. Preferably, the non-extendible blocker oligonucleotides comprise about 2 to about 25 reverse polarity nucleotide analogs at the 3' end. More preferably the non-extendible blocker oligonucleotides comprise about 5 to about 10 reverse polarity nucleotide analogs. Such probes are synthesized using conventional methods (see, e.g., Koga et al., J. Org. Chem. 56(12):3757-3759, 1991; Koga et al., Nucl. Acids Symp. Series 29:3-4, 1993; Koga et al., J. Org. Chem. 60:1520-1530, 1995). Other methods of making the oligonucleotide non-extendible can also be used.

Displacers

A displacer is a priming oligonucleotide which hybridizes to a template nucleic acid downstream (i.e., in the 3' direction on the template strand) from a primer hybridized to the target nucleic acid. When hybridized to the template nucleic acid, the 3'-terminal base of the displacers are adjacent to the 5-terminal base of the forward priming oligonucleotide. Preferably, the 3'-terminal base of the displacers are not immediately adjacent to the 5-terminal base of the forward priming oligonucleotide. Preferably, the adjacent 3'-terminal base of the displacers are spaced from the 5-terminal base of the forward priming oligonucleotide. More preferably, the adjacent 3'-terminal base of the displacers are spaced from 5 to 35 bases from the 5'-terminal base of the target binding segment of the forward priming oligonucleotide. The displacers may be provided to a reaction mixture contemporaneously with the primers or after the primers has had sufficient time to hybridize to the template nucleic acid. Extension of the primers can be initiated prior to or after the displacers are provided to a reaction mixture. Under amplification conditions, the displacers are extended in a template-dependent manner. The extended displacer displaces the primer-extended nucleic acid complexed with the template nucleic acid, releasing the primer-extended nucleic acid from the template nucleic acid. Examples of displacers and their uses are disclosed by Becker et al., US 2007-0202523.

Barcode Segment

Optionally, primers can further include a barcode segment. Barcodes are differentiable sequences useful for identifying the origin of a particular target nucleic acid segment. Barcodes are useful for sequencing pooled samples. For example, samples from two different sources can be independently amplified using primers having a unique barcode segment for each sample from a source. The amplified samples are then pooled and sequenced in a combined reaction. The unique sequences of the barcode segments identify the source of each sequenced sample.

Exonuclease

Exonuclease is an enzyme that cleaves nucleotides one at a time from an end of a polynucleotide chain, i.e., an enzyme that hydrolyzes phosphodiester bonds from either the 3' or 5' terminus of a polynucleotide molecule. Exemplary exonucleases include T4 DNA polymerase, T7 DNA polymerase, E. coli Pol 1, and Pfu DNA polymerase. Exonuclease activity is the activity associated with an exonuclease. An exonuclease that hydrolyzes in a 3' to 5' direction has 3' to 5' exonuclease activity. An exonuclease with 5' to 3' activity has 5' to 3' exonuclease activity. Some exonucleases are known to have both 3' to 5', 5' to 3' activity, such as, E. coli Pol I.

Nucleic Acid Polymerase

Nucleic acid polymerase is an enzyme that is capable of, in a template dependent manner, elongating at least one strand of nucleotides, e.g., a polynucleotide, by sequentially incorporating single nucleotides, typically, in a 5' to 3' direction. Nucleic acid polymerases include both DNA (DNA dependent DNA polymerases; RNA dependent DNA polymerases or reverse transcriptases) and RNA polymerases (DNA dependent RNA polymerases; RNA dependent RNA polymerases). 3' to 5' exonuclease or 3' to 5' exonuclease activity refers to a protein or domain of a protein that catalyzes the stepwise removal of mononucleotides from 3'-termini of DNA molecules, i.e., cleaving bonds, preferably phosphodiester bonds, between nucleotides one at a time from the end of a DNA molecule.

Nucleic Acid Polymerase with Exonuclease Activity

At least five families of DNA-dependent DNA polymerases are known, although most fall into families A, B and C. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. Accordingly, A-type, B-type, and C-type polymerases having 3' to 5' exonuclease activity can be used in the present method. In E. coli, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Thermostable or non-thermostable polymerases can be used. Examples of thermostable polymerase having 3' to 5' exonuclease activity include *Pyrococcus* polymerases e.g., Pfu, Pwo, Pho, Pab, Pko, Pgl polymerases; *Thermococcus* polymerases, e.g., *Thermococcus litoralis, Thermococus barossii*, and *Thermococcus gorgonarius* polymerases; and polymerases from *Pyrodictium* sp. Thermostable polymerases having 3' to 5' exonuclease activity can also be isolated from eubacterial strains such as *Thermotoga*. Non-thermostable polymerases can also be used. Examples of non-thermostable polymerases include the large fragment of *E. coli* DNA Polymerase I (Klenow) has 3' to 5' exonuclease activity. Preferably, a T4 DNA polymerase is used.

A nucleic acid polymerase with 3' to 5' exonuclease activity can be a hybrid protein comprising amino acid residues from multiple parent sequences. Examples of hybrid polymerase proteins and methods of generating hybrid proteins are disclosed in WO2004011605. Such polymerases are therefore non-naturally occurring variants of polymerases.

Aappropriate conditions for digesting with a polymerase with 3' to 5' exonuclease activity are described by e.g., Maniatis et al. Molecular Cloning—a Laboratory Manual; Cold Spring Harbor Laboratory Press First Edition (1989), p. 135).

Digestion of a nucleobase unit from a nucleic acid by a polymerase with 3'-5 nuclease activity means that the nucleobase unit is cleaved and not replaced by a nucleobase unit of the same type present in solution. A nucleobase unit that is transiently removed only to be replaced by a nucleobase unit of the same type resulting in the same template molecule as before the transient removal is not considered to have been digested.

Terminal Deoxynucleotidyl Transferase

Terminal deoxynucleotidyl transferase (TdT) is an enzyme that catalyzes the addition of at least one deoxyribonucleotide to the terminal 3'-hydroxyl of a DNA strand. TdT catalyzes the repetitive addition of mononucleotides from a deoxynucleoside triphosphate to the terminal 3'-hydroxy of a DNA initiator, with the release of inorganic phosphate. The enzyme requires an oligodeoxynucleotide containing at least three phosphate groups and a free 3'-OH to serve as initiator. Terminal transferase enzymes are widely available commercially. Terminal transferase enzymes suitable for the present methods can be recombinant. The reaction conditions for TdT extension has been described (see, e.g., Grosse & Manns, Enzymes of Molecular Biology, 16:95-105, 1993; Michelson & Orkin, Journal of Biological Chemistry, 257:14773-14782, 1982).

III. Methods 1 and 2

Generating a Closed Nucleic Acid Structure Using Linear, Single Strand Primers

Figure 2:
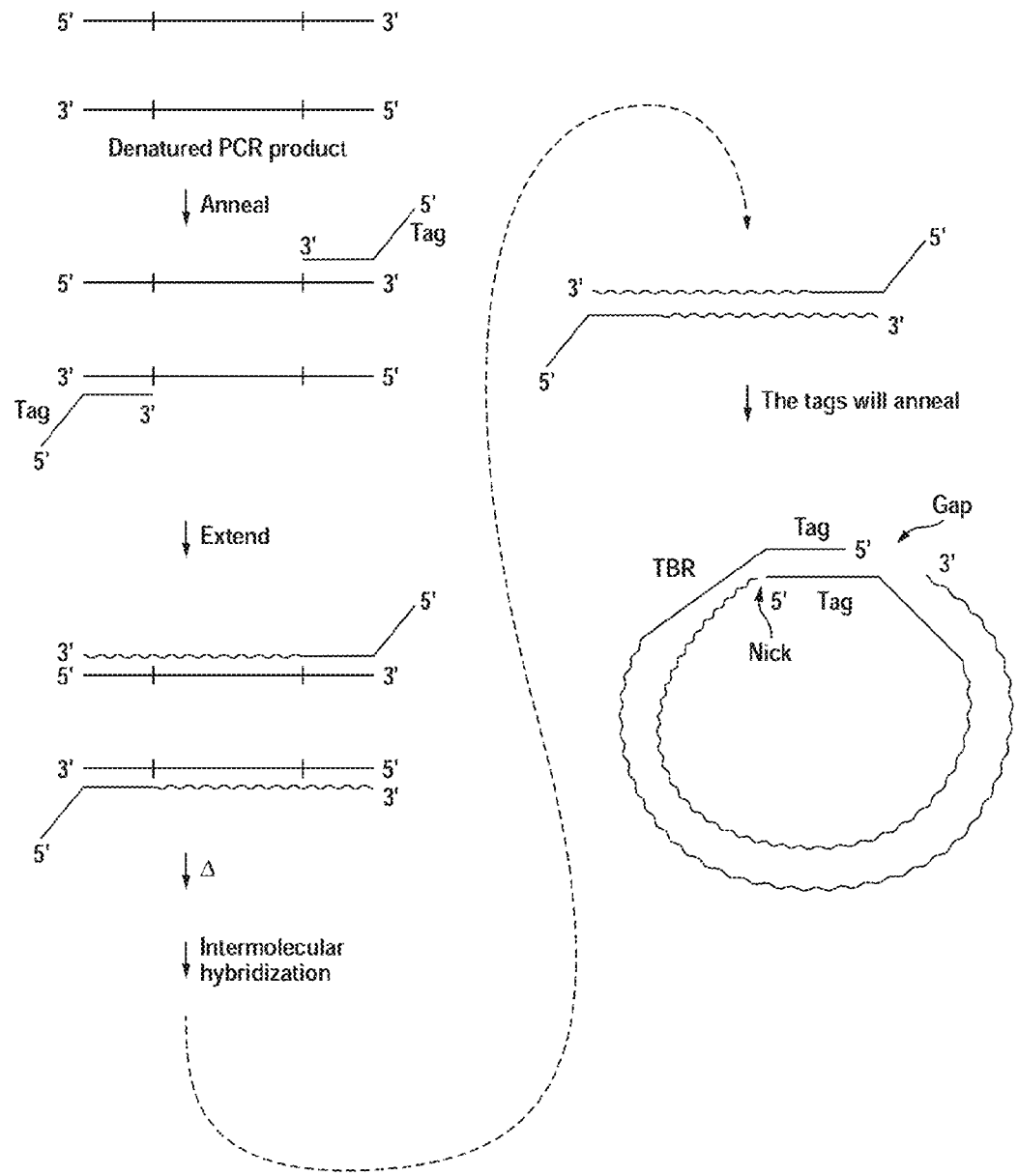
FIG. 2 illustrates an exemplary form of method 2 for generating a closed nucleic acid structure using a pair of primers having complementary 5' segments.

Exemplary forms of methods 1 and 2 are shown in FIGS. 1-2 for generating closed nucleic acid templates. The target nucleic acid can be a large nucleic acid containing a smaller target segment of interest (e.g., a genomic nucleic acid, a messenger RNA, a plasmid, a mitochondrial nucleic acid exosome) or the target nucleic acid can be a product of cycled primer extension reactions, such as in polymerase chain reaction (PCR), or to isothermal primer extension reactions, such as in transcription mediated amplification reactions (e.g., TMA).

FIG. 1 shows an exemplary form of method 1. A target nucleic acid comprising a target segment is used as the starting target nucleic acid. The starting target nucleic acid is then denatured, and a pair of linear, single strand primers is annealed to the target segment of opposing strands of the denatured target nucleic acid. Each of the primers has a 3' segment and a 5' segment. Each of the 5' segments is 5'-phosphorylated. The 3' segments of primers hybridize to opposing strands of the target nucleic acid. The primers are extended with a nucleic acid polymerase. To prevent extension of the 3' end of a template from proceeding across a 5' segment of a primer ("back-fill"), a number of techniques are employed. In one technique for preventing back-fill, the primers are annealed to the target at a position that is upstream on the target from its 3' nucleobase. The 3' end of the template, therefore, is not available for polymerase-based extension across the primer's 5' segment. To have extension products for use in the subsequent steps of methods 1 and 2, this back-fill prevention technique also employs extension blockers to generate extension products that align the 3' end of the new template with the 5' nucleobase of the incorporated primer's 3' segment when annealing together. In another technique for preventing back-fill, the primers are annealed to the target at a position wherein the 5' nucleobase of the primer's 3' segment is aligned with the 3' nucleobase of the target nucleic acid. The 3' end of the target is otherwise available for polymerase-based extension across the primer's 5' segment except when a back-fill prevention technique that employs extension blockers in the 3' nucleobase(s) of the 5' primer segments is used. In both instances the primers are extended with a polymerase in combination with a back-fill prevention technique. As exemplified in FIG. 1, some duplexes have a strand with an overhanging 5' segment from the first primer, and other duplexes have a strand with an overhanging 5' segment from the second primer.

Preferably, the primers are extended with a nucleic acid polymerase. In some methods amplification products are combined with tagged primers and only one cycle of extension reaction is performed to generate templates that form double stranded nucleic acids with 5' overhangs corresponding to the 5' primer segments. The single-cycle extension reaction employs a back fill prevention technique (such as an extension blocker) that can be used to generate a plurality of double stranded products with 5' overhangs. In the absence of extension blockers to prevent back fill, the extension reaction produces amplification products having, at the 5' end, a 5' segment from a primer, and at the 3' end, complement of a 5' segment from the other primer. Such amplification products are not desired because they cannot anneal to each other to form a duplex with overhanging 5' segments, which are needed for generating closed nucleic acid structures. Side products having both 5' segments in a single strand can be readily separated and discarded.

The primer-extended nucleic acid can be released from the template by denaturation, i.e., by heating the template to a denaturing temperature, e.g., temperatures above about 85° C. Once the primer-extended nucleic acid is released from the template, the template strand can be optionally digested or otherwise removed.

In some forms of method 1, the primer-extended nucleic acids are denatured and mixed with one or more adaptors having a 5' region and a 3' region. As shown in FIG. 1, the 3' region of the adaptor has a stem-loop structure, the 5' region of the adaptor is complementary to one or both of the 5' segment(s) of the primers. Under annealing conditions, one strand having the 5' segment from the first primer and an opposing strand having the 5' segment from the second primer anneal to each other to form a duplex having overhanging 5' segments at both ends but on different strands. Adaptors are annealed to the overhanging 5' segments of the duplex, with the 5' regions of the adaptors hybridize to the 5' segments of the duplex. The 5' segment from the first primer and the 5' segment from the second primer can be the same or different. Accordingly, one or two adaptors can be used in combination with the 5' segments. For example, when the two 5' segments have different sequences and/or lengths, two adaptors can be used, each of the adaptors hybridizes to different overhanging 5' segments.

Preferably, the nicks in the closed nucleic acid structure are sealed using a nucleic acid ligase. The 5' ends of primers and the adaptors are phosphorylated, the 5' phosphate groups are ligated to an adjacent 3' hydroxyl group in either the 3' region of the adaptor or the 3' ends of the target nucleic acids. The ligated nucleic acid is topologically a closed nucleic acid structure having a duplex target nucleic acid "capped" by stem-loop adaptors at both ends.

Method 2, shown in FIG. 2, is a variation of method 1. A target nucleic acid comprising a segment of interest is denatured, and a pair of linear, single strand primers is annealed to the opposing strands of the denatured target nucleic acid. The primers are similar to those used in FIG. 1, e.g., each of the primers has a 3' segment and a 5' segment, and the 3' segments of primers hybridize to opposing strands of the target nucleic acid. However, in FIG. 2 the 5' segments of the first primer and the second primer are complementary to each other. In addition, only one of the 5' segments, e.g., the first primer, needs to be phosphorylated. The second primer is preferably unphosphorylated at its 5' end, especially when the two primers are of the equal length.

The primers are extended with a nucleic acid polymerase, preferably in a single-cycle of extension (i.e., the primer-extended nucleic acid is not used as a template for primer extension reaction) resulting in duplexes having an overhanging 5' segments on one strand of the duplex but not on the opposing strand.

The primer-extended nucleic acid can be released from the template by denaturation, i.e., by heating the template to a denaturing temperature, e.g., temperatures above about 85° C.

The released nucleic acids are then subject to annealing conditions. Under annealing conditions, one strand having the 5' segment from the first primer and an opposing strand having the 5' segment from the second primer anneal to each other to form a duplex having overhanging 5' segments at both ends but on different strands. The duplex circularizes by annealing complementary overhanging 5' segments at both ends to each other (FIG. 2). When the 5' segment from the second primer is shorter than the 5' segment from the first primer, a gap forms between the 5' segment from the second primer and an adjacent 3' hydroxyl group from the 3' end of the target nucleic acid (FIG. 2).

The 5' phosphate on the 5' segment from the first primer is ligated to an adjacent 3' hydroxyl group, leaving a gap in the closed nucleic acid between the other 5' terminus on the 5' segment from the second primer and an adjacent 3' hydroxyl (FIG. 2). This 3'-hydroxyl serves as a priming end to initiate template-directed synthesis of a nascent chain in circles around the template generating alternating reads of primer segments and the target nucleic acid. Because the closed nucleic acid structure contains only one priming site, only one strand of the target nucleic acid is read from a given template.

The closed nucleic acid structures of methods 1 and 2 can be purified from linear products using standard methods such as gel purification or affinity chromatography.

IV. Methods 3 and 4

Figure 3:
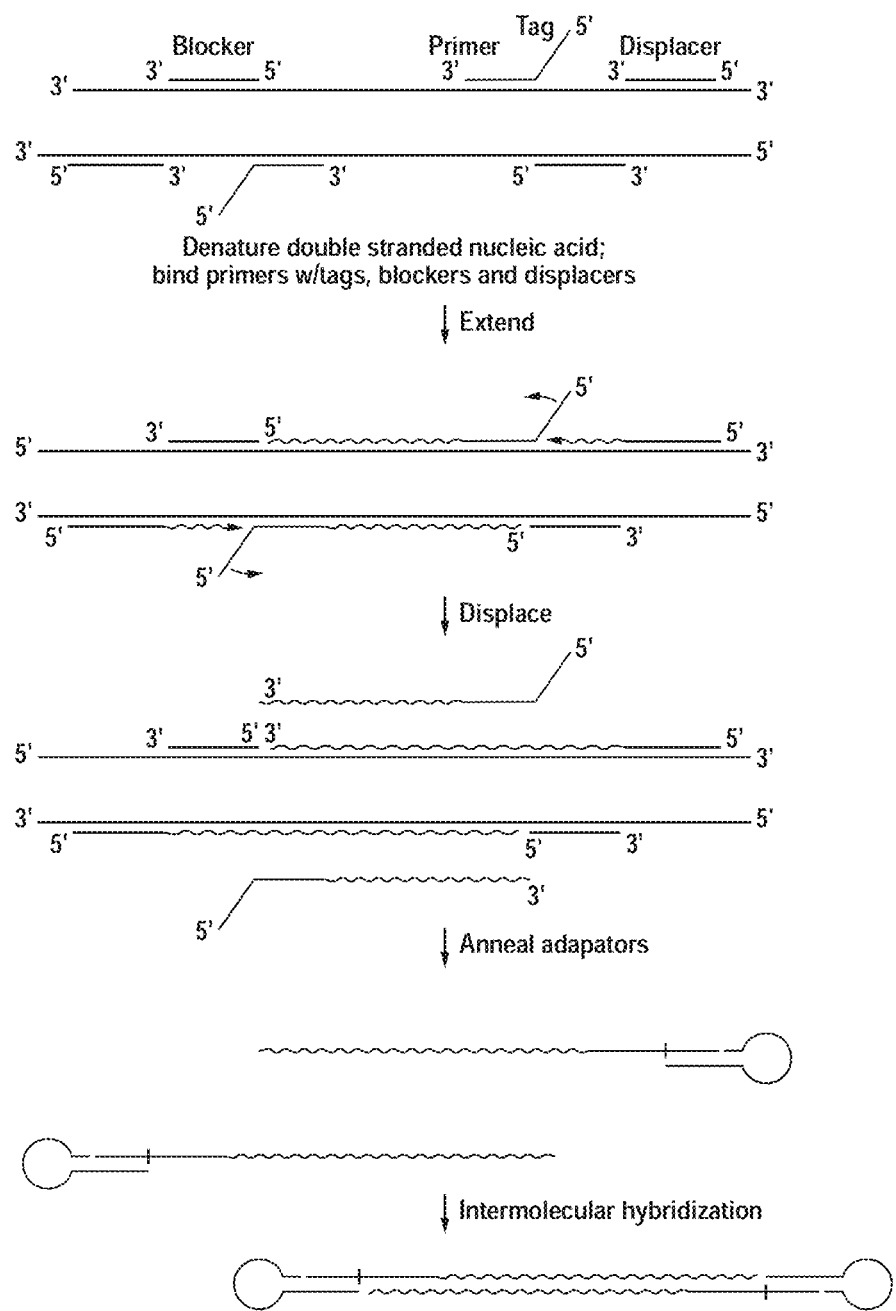
FIG. 3 illustrates an exemplary form of method 3 for generating a closed nucleic acid structure using a pair of primers, a pair of corresponding adaptors, a pair of blockers and a pair of displacers.
Figure 4:
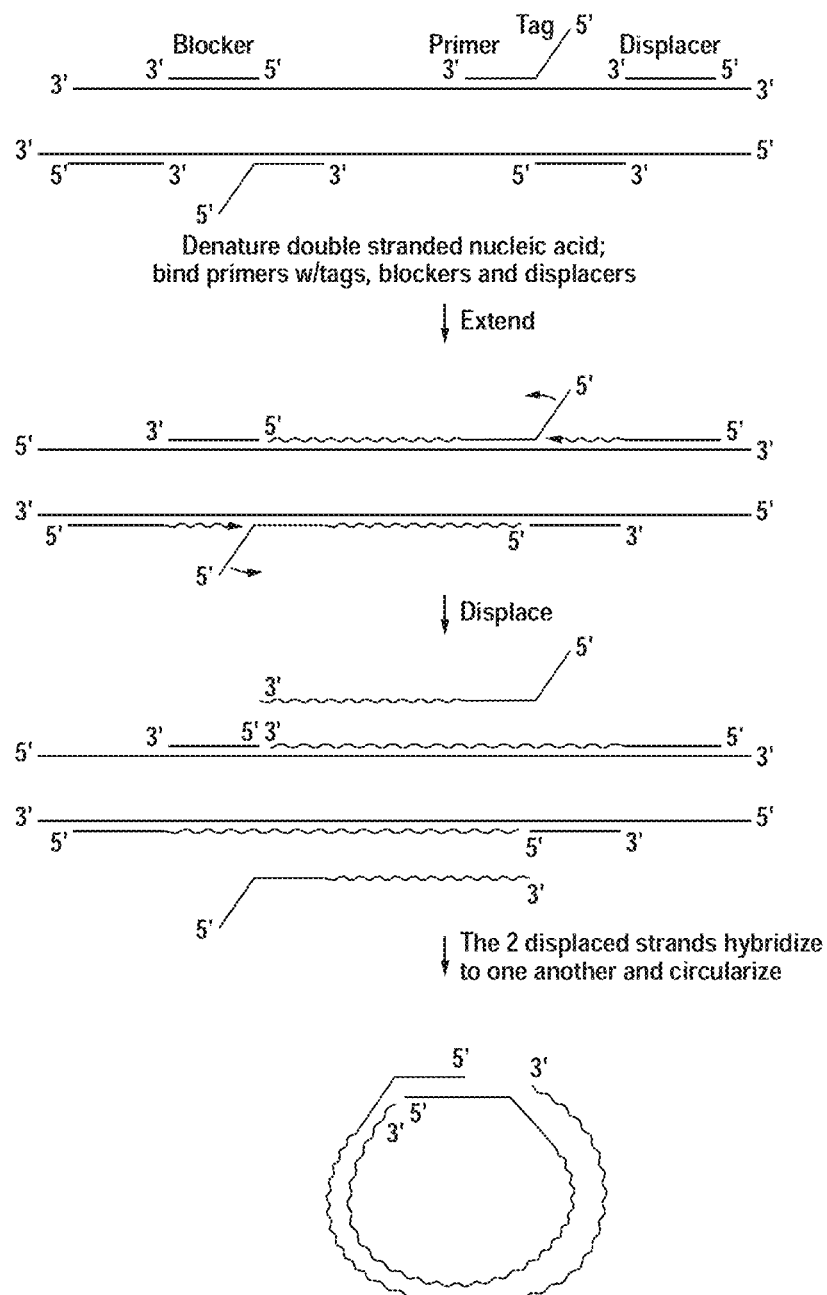
FIG. 4 illustrates an exemplary form of method 4 for generating a closed nucleic acid structure using a pair of primers having complementary 5' segments, a pair of blockers and a pair of displacers.

Generating a Closed Nucleic Acid Structure Using Non-Extendible Blocker Oligonucleotide In methods 3 and 4, a target segment in a target nucleic acid is defined using a non-extendible blocker oligonucleotide pair and a primer pair. Exemplary forms of methods 3 and 4 are shown in FIGS. 3-4 for generating closed nucleic acid structures. The target nucleic acid can be a product of cycled primer extension reactions, such as in polymerase chain reaction (PCR), or to isothermal primer extension reactions, such as in transcription mediated amplification reactions (e.g., TMA), or a non-amplified target. As shown in FIGS. 3-4, a pair of linear, single strand primers are annealed to the opposing strands of a denatured target nucleic acid, and extended with a nucleic acid polymerase. Each of the primers has a 5' segment and a 3' segment. The 3' segments of primers are target-binding segments and hybridize to opposing strands of the target nucleic acid.

The extension of the primers is blocked by the non-extendible blocker oligonucleotide pair located at a defined position downstream of the primers, as shown in FIGS. 3-4. The extension of the primers results in primer-extended target nucleic acids having overhanging 5' segments. As exemplified in FIGS. 3-4, some primer-extended target nucleic acids have an overhanging 5' segment from the first primer, and other primer-extended target nucleic acids have an overhanging 5' segment from the second primer.

These primer-extended target nucleic acids can be released from the starting target nucleic acids heating the template to a denaturing temperature, e.g., temperatures above about 85° C. Alternatively, the primer-extended nucleic acid can be released from the template using a displacer as shown in FIGS. 3-4. A displacer hybridizes to the template upstream of the primer-extended nucleic acid. Under extension conditions, the displacer is extended in a template-dependent manner. The extended displacer displaces the primer-extended nucleic acid complexed with the template nucleic acid, releasing the primer-extended nucleic acid from the template nucleic acid.

Method 3:

The released primer-extended target nucleic acids can be mixed with one or more adaptors having a design similar to those described in method 1, e.g., having a 5' region complementary to the 5' segment(s) of the primers and a stem-loop 3' region. Under annealing conditions, the primer-extended target nucleic acids, one strand having the 5' segment from the first primer and an opposing strand having the 5' segment from the second primer, anneal to each other to form a duplex having overhanging 5' segments at both ends but on different strands. Adaptors are annealed to the overhanging 5' segments of the duplex, with the 5' regions of the adaptors hybridizing to the 5' segments at both ends of the duplex. The 5' segment from the first primer and the 5' segment from the second primer can be the same or different.

The closed duplex can be ligated to generate a closed nucleic acid structure using procedures similar to those used for ligating closed nucleic acid structures depicted in method 1. The nicks in the closed nucleic acid structure are sealed using a nucleic acid ligase.

Method 4:

Primers having a design similar to those described in method 2 are used, e.g., the 5' segments from the first primer and the second primer are complementary. Under annealing conditions, the primer-extended target nucleic acids, one strand having the 5' segment from the first primer and an opposing strand having the 5' segment from the second primer, anneal to each other to form a duplex having overhanging 5' segments at both ends but on different strands. The duplex circularizes by annealing complementary overhanging 5' segments at both ends to each other (FIG. 4).

As with Method 2, if a nick exists in both strands, both can be sealed using a ligase. Likewise, if one strand contains a nick and one strand contains a gap, the nick is sealed with a ligase and the gap is not sealed. The free 3'-hydroxyl on the strand containing the gap serves as a priming end to initiate template-directed synthesis of a nascent chain during sequencing of the target nucleic acid.

The closed nucleic acid structures of methods 3 and 4 can be purified from linear products using standard methods such as gel purification or affinity chromatography.

V. Methods 5 and 6

Figure 5:
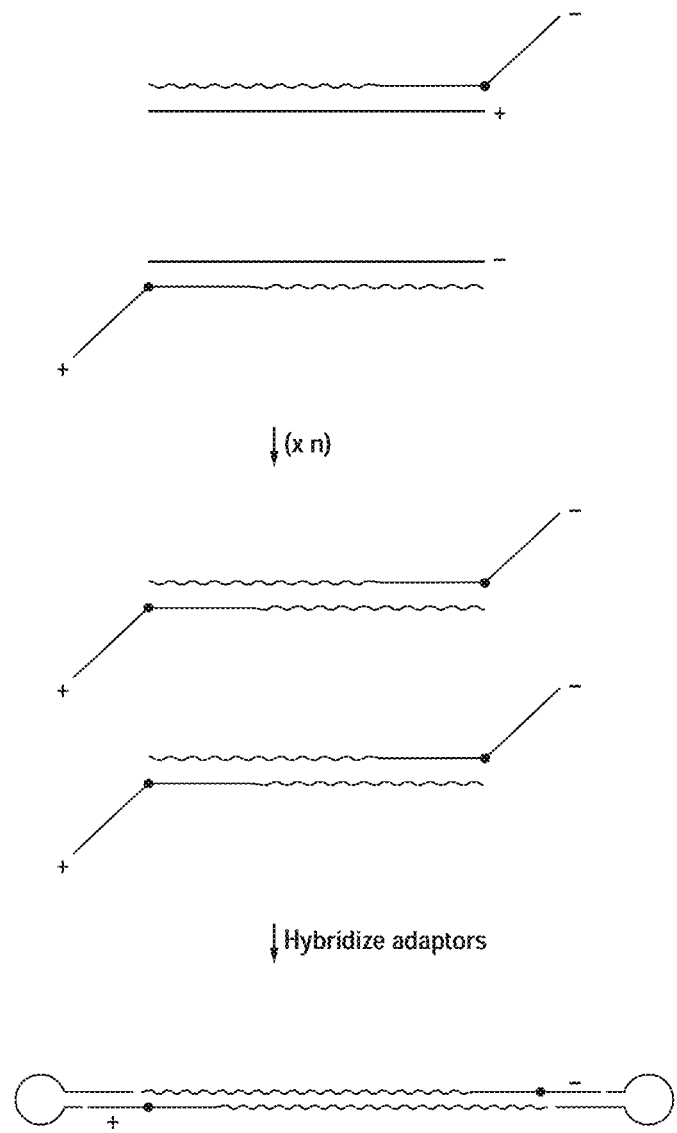
FIG. 5 illustrates an exemplary form of method 5 for generating a closed nucleic acid structure using a pair of primers containing extension blockers, and a pair of corresponding adaptors.
Figure 6:
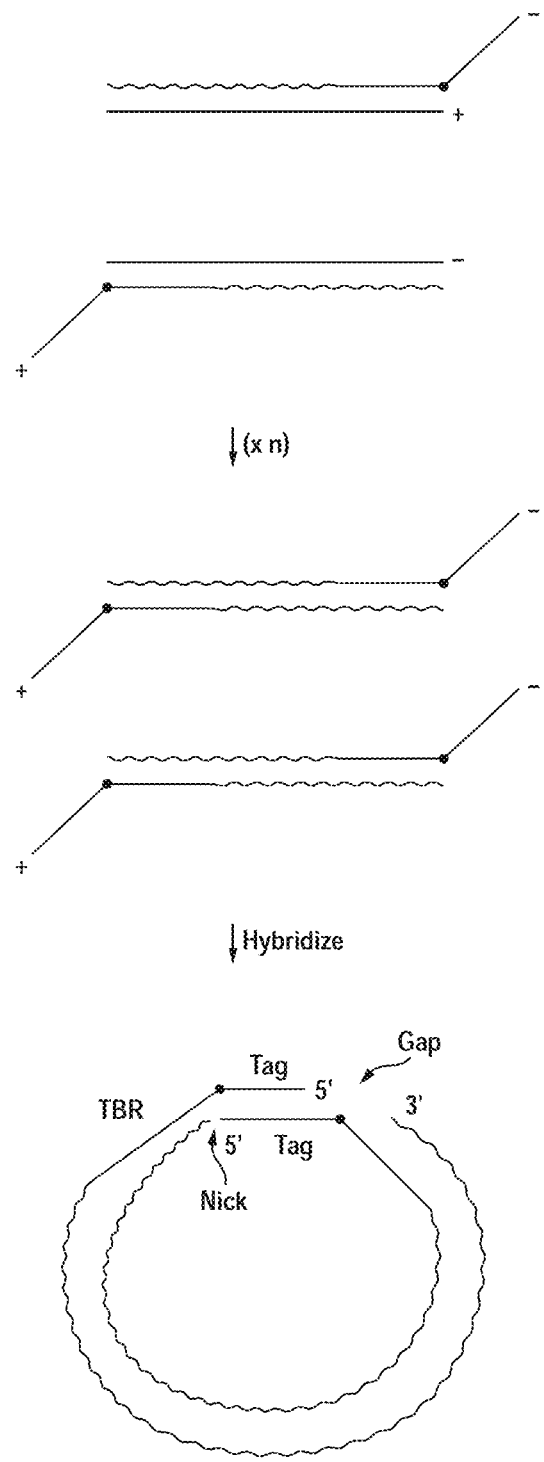
FIG. 6 illustrates an exemplary form of method 6 for generating a closed nucleic acid structure using a pair of primers having extension blockers and complementary 5' segments.

Generating a Closed Nucleic Acid Structure Using Primers with an Extension Blocker Methods 5 and 6 define a target segment in a target nucleic acid using primers with an extension blocker. As shown in FIGS. 5-6, a target nucleic acid is subjected to cycled primer extension reactions using a pair of primers having a 5' segment, a 3' segment, and an extension blocker at the first 3'→5' nucleobase unit of the 5' segment. The primers hybridize to opposing strands of the target nucleic acid. To prevent extension of the template across a 5' segment of a primer ("back-fill"), a number of techniques are employed. One technique for preventing back-fill includes providing a non-canonical nucleobase at the 3' position of the primer's 5' segment. In this way, the non-canonical nucleobase is one that does not serve as a template for the polymerase, and so extension of the 3' end of the template across the tag 5' tag sequence does not occur. Because template extension is blocked by the extension blocker on the primer, amplification with the primer pair results in an amplification product having a strand comprising an overhanging 5' segment from the first primer and an opposing strand comprising an overhanging 5' segment from the second primer (FIGS. 5-6). The amplification products can be used directly in the downstream process, e.g., annealing to an adaptor to form a closed nucleic acid structure or circularizing to form a closed nucleic acid structure as previously described in Methods 1 and 3.

In some primers used in methods 5-6, the extension blocker is a reversibly modified nucleotide, e.g., nucleotides with O-linked triisopropylsilyl groups, O-linked tertButyl-dimethylsilyl groups or O-linked alkyl groups at the 2' carbon atom; a ribonucleotide; or a nucleobase unit of a pair of non-canonical nucleobase units, e.g., isoC or isoG, which only base pair with their partner non-canonical nucleobases. Because of the extension blocker, nucleobase unit extension stops when the primer extension reaches a position on the template that is occupied by an extension blocker. The extension blocker is reversed for downstream reactions, such as a sequencing reaction, using conditions suited to the particular extension blocker used.

In method 5, one or more adaptors having a 5' region complementary to the 5' segment(s) of the primers and a stem-loop 3' region are used. Under annealing conditions, such adaptors are annealed to two overhanging 5' segments of the amplification product, with the 5' regions of the adaptors hybridized to the 5' segments at both ends of the duplex (FIG. 5). The 5' segment from the first primer and the 5' segment from the second primer can be the same or different.

The nicks in the closed nucleic acid structure are sealed using a nucleic acid ligase. Because the 5' ends of both primers and adaptors are phosphorylated, these 5' phosphate groups are ligated to an adjacent 3' hydroxyl group in either the 3' region of the adaptor or the 3' ends of the target nucleic acids.

Method 6 uses a primer pair of first and second primers having complementary 5' segments from the first primer and the second primer is used. Under annealing conditions, the amplification product, one strand having an overhanging 5' segment from the first primer and an opposing strand having an overhanging 5' segment from the second primer, circularizes by annealing complementary overhanging 5' segments at both ends to each other (FIG. 6). The 5' segment of the first primer is phosphorylated. The second primer either has a shorter 5' segment than the first primer and/or lacks a 5' phosphate at its 5' end. The closed duplex can be ligated to generate a closed nucleic acid having a single nick or gap. The intermediate product circularizes via intramolecular annealing of two overhanging 5' segments. As discussed above, the nick in one strand of the closed nucleic acid structures is typically sealed using a nucleic acid ligase whereas the opposing strand contains an unsealed nick or gap. The free 3'-hydroxyl on the opposing strand serves as a priming end to initiate template-directed synthesis of a nascent chain during a sequencing of the target nucleic acid.

During the amplification/sequencing of the closed nucleic acid structure, the partnering nucleobase unit of the extension blocker is included in the amplification/sequencing reaction. Because the partnering nucleobase unit can base pair with the extension blocker, the nucleobase unit extension is no longer blocked by the extension blocker on the template.

The closed nucleic acid structures of methods 5 and 6 can be purified from linear products using standard methods such as gel purification or affinity chromatography.

VI. Methods 7-10

Generating a Closed Nucleic Acid Structure Using Stem-Loop Primers

Methods 7-10 use stem-loop primers. A starting target nucleic acid is denatured, and a pair of stem-loop primers is annealed to the opposing strands of a denatured target nucleic acid, and extended with a nucleic acid polymerase. Each of the primers has a stem-loop 5' segment and a target-binding 3' segment. The 3' segments are target-binding segments and hybridize to opposing strands of the target nucleic acid. Exemplary forms of the methods 7-10 using a pair of primers, a pair of non-extendible blockers and a pair of displacers are shown in FIGS. 7-8.

Method 7:

The primers are extended with a nucleic acid polymerase in one cycle of extension reaction. The extension of the primers is blocked by the non-extendible blocker oligonucleotide pair located downstream of the primers, as shown in FIGS. 7-8. The extension of the primers results in primer-extended target nucleic acids having overhanging stem-loop 5' segments.

Figure 7:
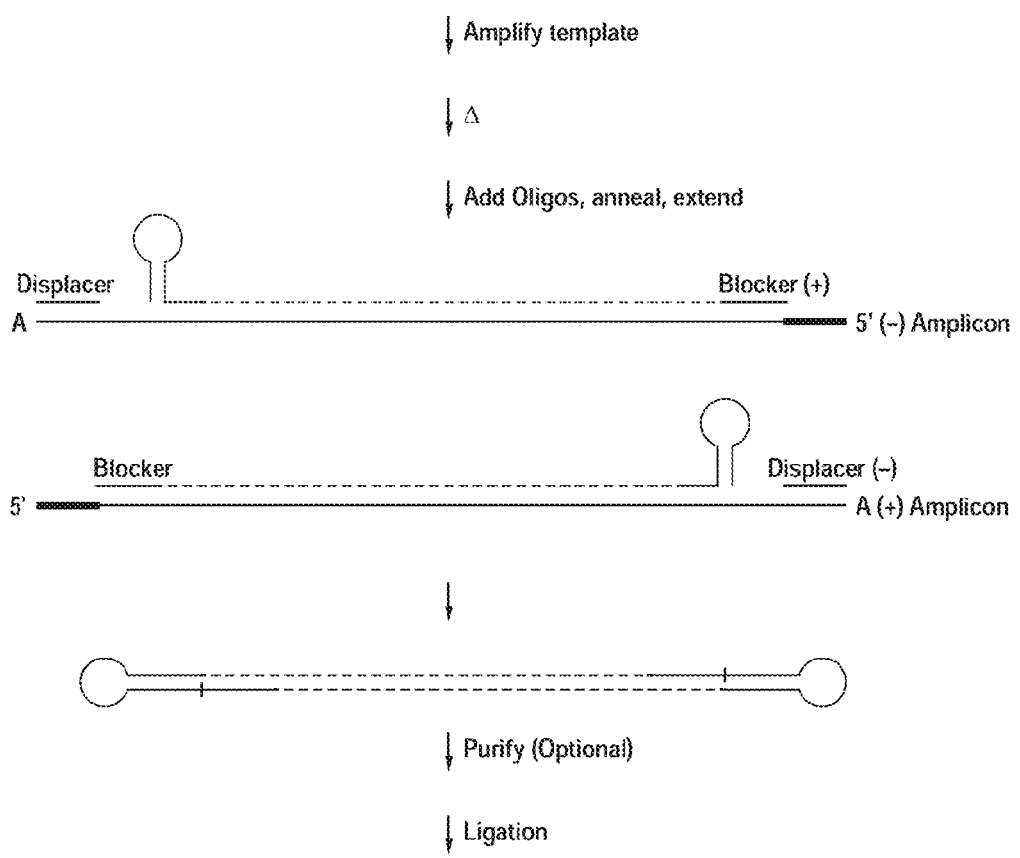
FIG. 7 illustrates an exemplary form of method 7 for generating a closed nucleic acid structure having two stem-loops using a pair of primers containing stem-loop structures.
Figure 8:
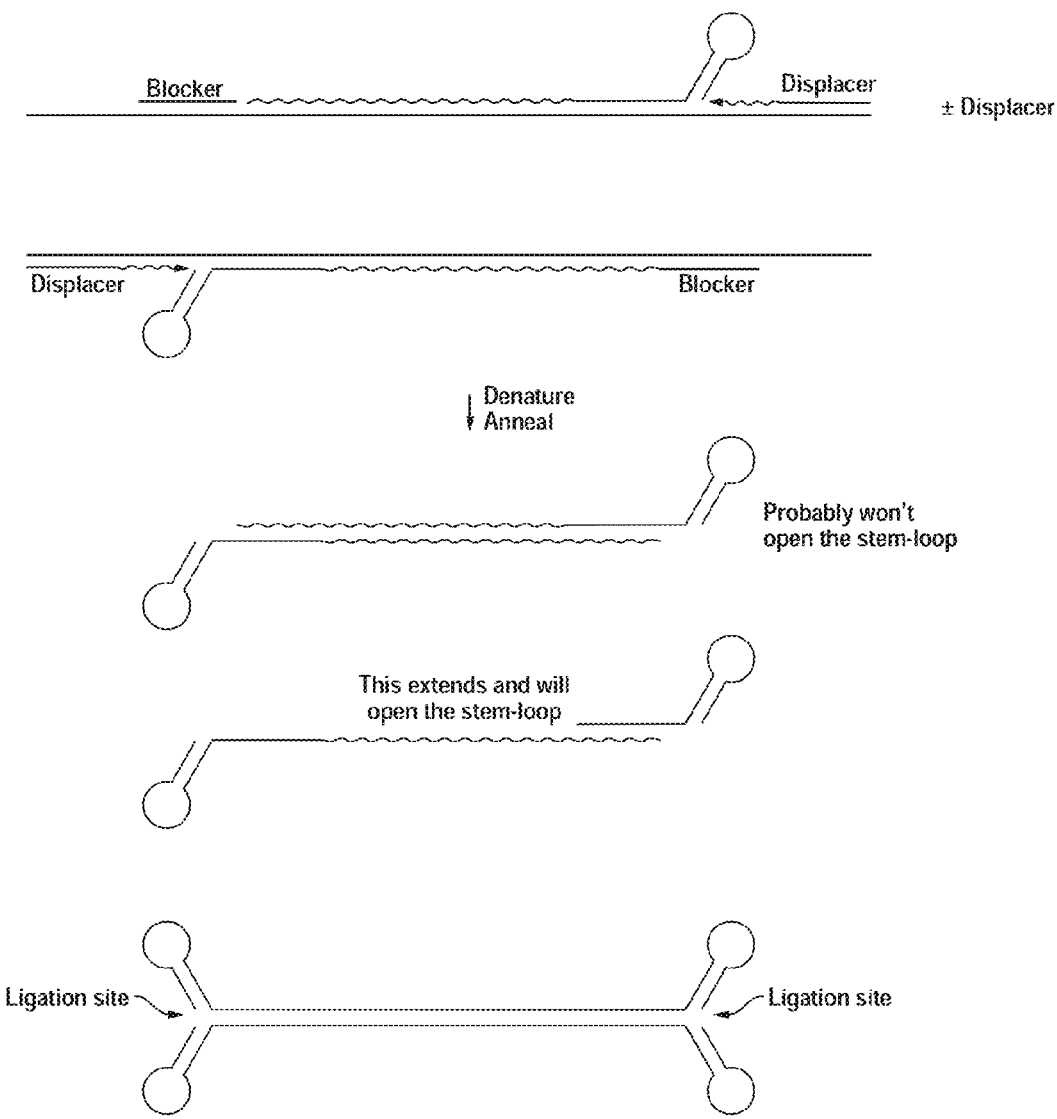
FIG. 8 illustrates an exemplary form of method 8 for generating a closed nucleic acid structure having four stem-loops using a pair of primers containing stem-loop structures.

The primer-extended target nucleic acids can be released from the starting target nucleic acids as shown in FIGS. 7-8 to generate closed nucleic acid structures. The primer-extended nucleic acid can be released from the template by denaturation, i.e., by heating the template to a denaturing temperature, e.g., temperatures above about 85° C. Alternatively, the primer-extended nucleic acid can be released from the template using a displacer. A displacer hybridizes to the template downstream of the primer-extended nucleic acid. Under extension conditions, the displacer is extended in a template-dependent manner. The extended displacer displaces the primer-extended nucleic acid complexed with the template nucleic acid, releasing the primer-extended nucleic acid from the template nucleic acid.

Under annealing conditions, the primer-extended target nucleic acids, one strand having the stem-loop 5' segment from the first primer and an opposing strand having the stem-loop 5' segment from the second primer anneal to each other to form a duplex having stem-loops at both ends but at different strands.

Because the 5' ends of both primers are phosphorylated, these 5' phosphate groups are ligated to an adjacent 3' hydroxyl group in the 3' ends of the target nucleic acids to form certain forms of closed nucleic acid structure having a duplex target nucleic acid "capped" by stem-loop primers (FIG. 7).

Method 8 is performed with more than one cycle of extension (e.g., the target nucleic acid is amplified using the primers under PCR conditions). The primer-extended target nucleic acids are further amplified using the stem-loop primers, resulting in an amplification product having stem-loops at both ends of a single strand, i.e., a duplex having four stem-loops (FIG. 8). The duplex is then ligated to seal the nicks between the 5' phosphate groups of the 5' stem-loops and adjacent 3' hydroxyl group in the 3' stem-loops.

In methods 9 and 10, stem-loop primers with an extension blocker can be used as shown in FIG. 9. The target nucleic acid is amplified using a pair of stem-loop primers with an extension blocker, hybridizing to opposing strands of a target nucleic acid (if double-stranded) or to a target nucleic acid and its complementary strand, if the target nucleic acid is single-stranded, is used. The primer has a 3' segment and a 5' segment, the 3' segments of the primers being target-binding segments and the 5' segments comprising a stem-loop structure. Preferably, the first 3'→5' nucleobase unit in the 5' segment is an extension blocker, base-pairing with a partnering nucleobase unit in the stem segment.

Figure 9A:
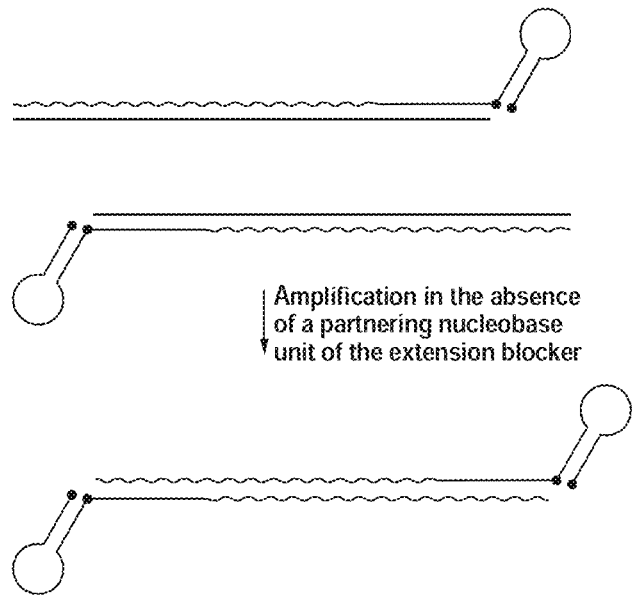
FIGS. 9A, B illustrate exemplary forms of methods 9 and 10 for generating a closed nucleic acid structure having two or four stem-loops using a pair of primers containing stem-loop structures and an extension blocker.

Method 9:

If the amplification is carried out in the absence of a partnering nucleobase unit, the nucleobase unit extension is blocked by the extension blocker on the template, resulting in an amplification product having overhanging stem-loop 5' segments (FIG. 9A). The amplification product can be ligated to form a closed nucleic acid structure because the 5' ends of both primers are phosphorylated.

Figure 9B:
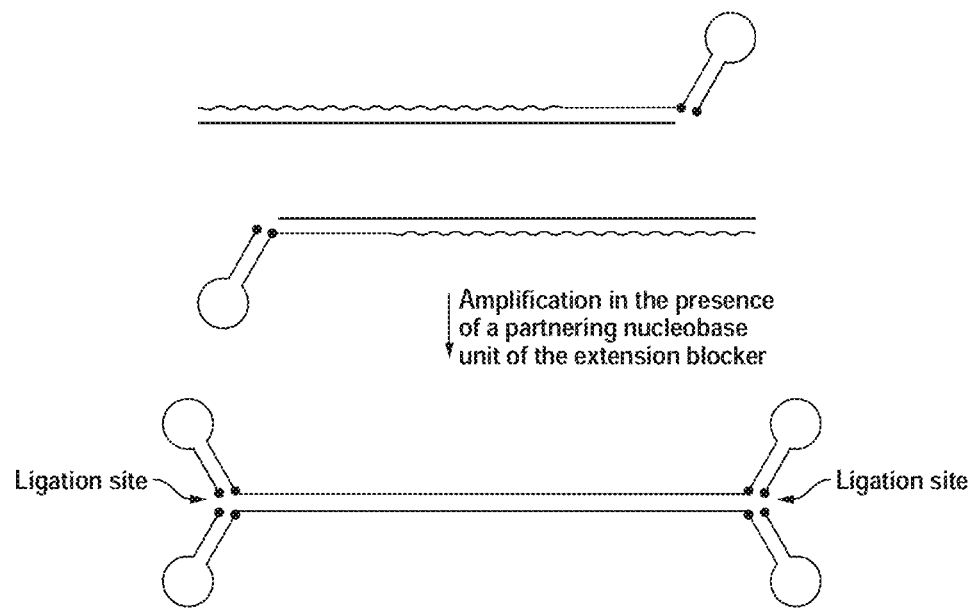

Method 10:

Alternatively, if the amplification is carried out in the presence of a partnering nucleobase unit (as well as other canonical nucleobase units), the nucleobase unit extension is not blocked by the extension blocker on the template, resulting in an amplification product having stem-loops at both ends of a single strand, i.e., a duplex having four stem-loops (see bottom of FIG. 9B). The duplex is then ligated to seal the nicks between the 5' phosphate groups of the 5' stem-loops and adjacent 3' hydroxyl group in the 3' stem-loops.

The closed nucleic acid structures of methods 7-10 can be purified from linear products using standard methods such as gel purification or affinity chromatography.

VII. Methods 11 and 12

Generating a Closed Nucleic Acid Structure Using Duplex Primers

Figure 10:
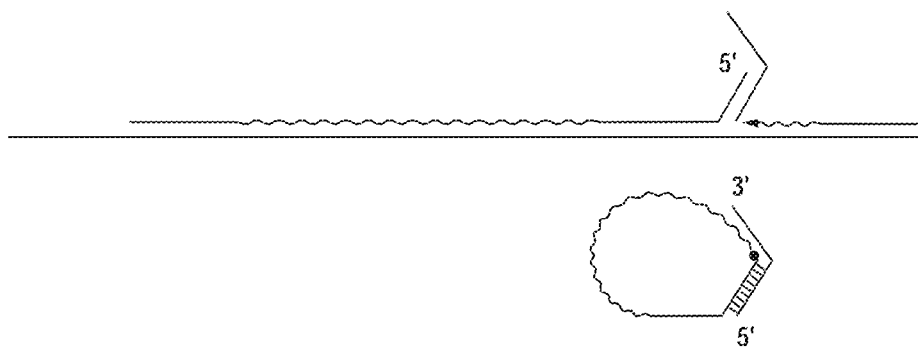
FIG. 10 illustrates an exemplary form of method 11 for generating a closed nucleic acid structure using a duplex primer.

Methods 11 and 12 use duplex primers as shown in FIG. 10. The first overhanging 3' segment of the duplex primer is the target-binding segment. The 5' end of the first strand is phosphorylated.

As detailed below, the formation of a closed nucleic acid structure requires only one strand of the primer-extended nucleic acid. Preferably, only one primer, hybridizing to one strand of a target nucleic acid, is used for making a closed nucleic acid structure. Optionally, a primer pair hybridizing to opposing strands of a target nucleic acid (if double-stranded) or to a target nucleic acid and its complementary strand, if the target nucleic acid is single-stranded, is used.

When a primer pair is used, the primer is extended with a nucleic acid polymerase preferably in one cycle of extension reaction. When only one primer instead of a primer pair is used, additional cycles of extension reaction do not produce amplification products from the opposing strand. Because the primer on the opposing strand is not present, additional cycles of extension reaction simply produce additional copies of primer-extended nucleic acids. In such cases, additional cycles of extension reaction are allowed.

Method 11:

In some forms of method 11, the extension of the primer is blocked by the non-extendible blocker oligonucleotide pair located upstream of the primers, as shown in FIG. 10. The extension of the primers results in primer-extended target nucleic acids having overhanging duplex region with a second overhanging 3' segment.

Release of the primer-extended nucleic acid from the template generates a closed nucleic acid structure. The primer-extended target nucleic acids can be released from the template using a displacer oligonucleotide as shown in FIG. 10.

The primer is designed so that the 3' end region of the primer-extended target nucleic acid is complementary to the second overhanging 3' segment of the primer. Under annealing conditions, the primer-extended target nucleic acids circularizes by annealing its 3' end region to the second overhanging 3' segment of the primer (FIG. 10). The nick between the 5' phosphate group from the first strand of the primer and the 3' end of the primer-extended target nucleic acid can be sealed by a ligase.

Figure 11:
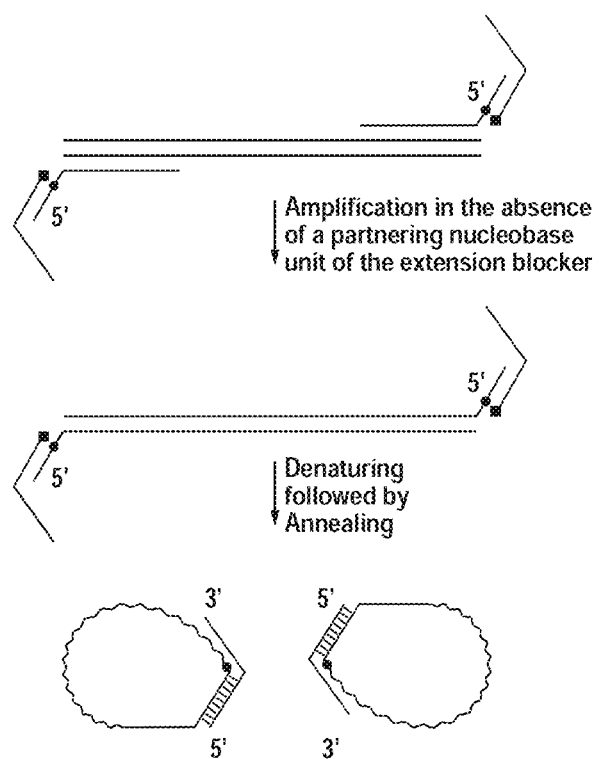
FIG. 11 illustrates an exemplary form of method 12 for generating a closed nucleic acid structure using a duplex primer with an extension blocker.

Method 12 uses a pair of duplex primers with an extension blocker as shown in FIG. 11. The target nucleic acid is amplified using a pair of duplex primers with an extension blocker, hybridizing to opposing strands of a target nucleic acid (if double-stranded) or to a target nucleic acid and its complementary strand, if the target nucleic acid is single-stranded, is used. The primer has a duplex region flanked by a first overhanging 3' segment in a first strand and a second overhanging 3' segment in an opposing strand, the first overhanging 3' segment being a target-binding segment. The first strand having a 5' phosphate group, and the first 3'→5' nucleobase unit in the 5' segment is an extension blocker, base-pairing with a partnering nucleobase unit in the opposing strand of the duplex region. The first overhanging 3' segment of the first primer can be the same as, or different than, the second overhanging 3' segment of the second primer. Similarly, the first overhanging 3' segment of the second primer can be the same as, or different than, the second overhanging 3' segment of the first primer.

In the absence of a partnering nucleobase unit of the extension blocker, the nucleobase unit extension is blocked by the extension blocker on the template, resulting in an amplification product having a strand comprising a duplex region and a second overhanging 3' segment from the first primer and an opposing strand comprising a duplex region and a second overhanging 3' segment from the second primer. If an amplification method such as PCR is used, the duplex primer denatures during the denaturation step. During the annealing step of the PCR, two strands of the duplex primer anneal together.

The amplification product is then denatured, separating the second strand of the first primer and the second strand of the second primer from the amplified target nucleic acid, resulting in a first denatured strand having a 5' segment from the first strand of the first primer and a second denatured strand having a 5' segment from the first strand of the second primer.

Under annealing conditions, the second strand of the first primer hybridizes to the first denatured strand, i.e., the 5' segment of the second strand of the first primer hybridizes to the 5' segment of the first strand of the first primer from the first denatured strand, and the 3' segment of the second strand of the first primer hybridizes to its complementary region at the 3' end of the first denatured strand. In addition, the second strand of the second primer hybridizes to the second denatured strand, i.e., the 5' segment of the second strand of the second primer hybridizes to the 5' segment of the first strand of the second primer from the second denatured strand, and the 3' segment of the second strand of the second primer hybridizes to its complementary region at the 3' end of the second denatured strand (FIG. 11). The first or second denatured strand circularizes to form two different closed nucleic acid structures, each comprising one of the opposing strands of the target nucleic acid.

The nick between the 5' phosphate group of the first denatured strand and the adjacent 3' hydroxyl group from the 3' end of the first denatured strand and/or the nick between the 5' phosphate group of the second denatured strand and the adjacent 3' hydroxyl group from the 3' end of the second denatured strand; thereby forming a template, can be sealed by a ligase.

The closed nucleic acid structures of methods 11 and 12 can be purified from linear products using standard methods such as gel purification or affinity chromatography.

VIII. Method 13

Figure 12:
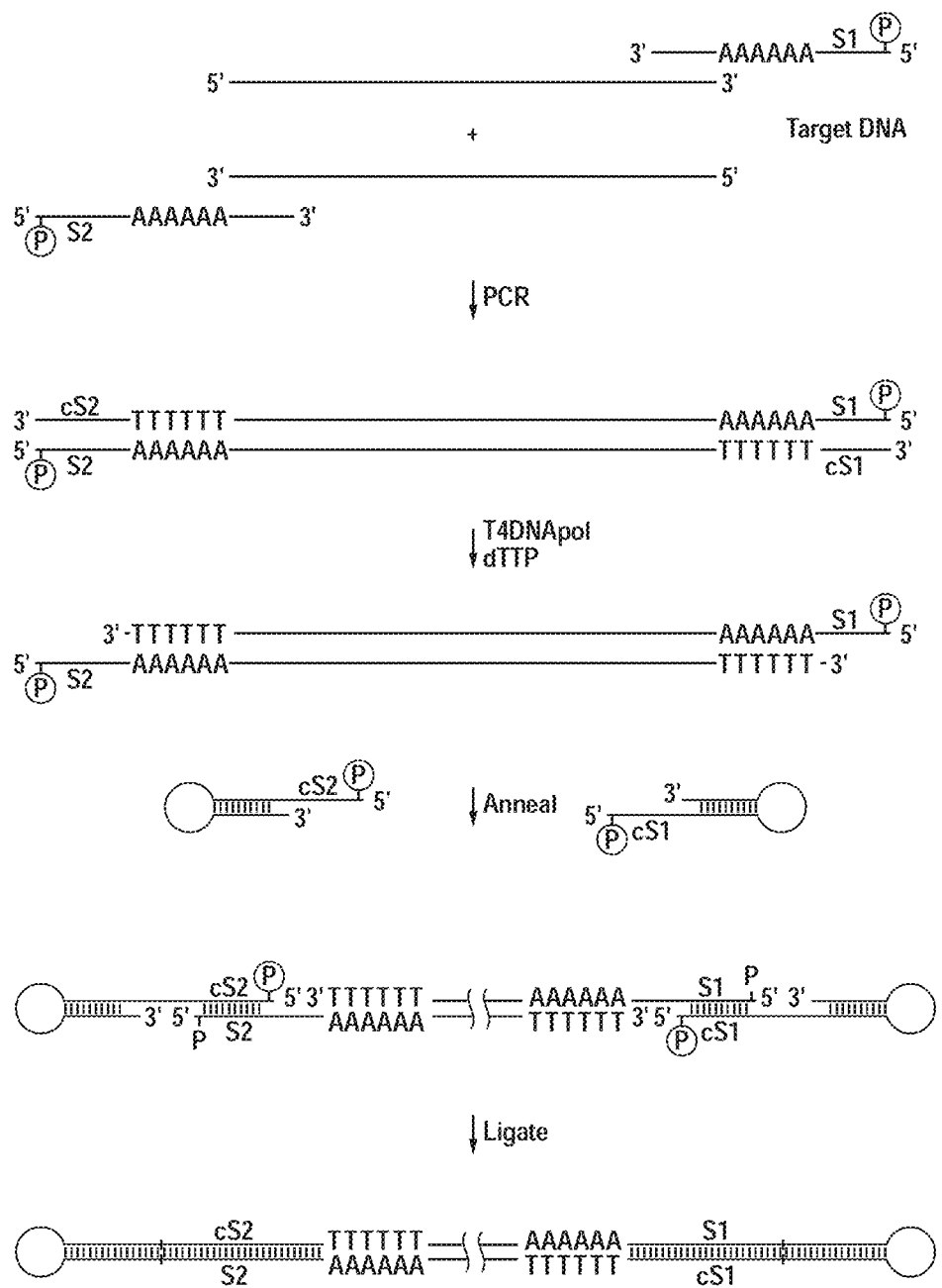
FIG. 12 illustrates an exemplary form of method 13 for generating a closed nucleic acid structure using a nucleic acid polymerase with 3' to 5' exonuclease activity and a pair of adaptors.

Generating a Closed Nucleic Acid Structure Using Nucleic Acid Polymerases with 3' to 5' Exonuclease Activity Method 13 generates a closed nucleic acid template utilizing a 3'-5' exonuclease activity. An exemplary form of method 13 is shown in FIG. 12. A target nucleic acid is subjected to cycled primer extension reactions, such as in polymerase chain reaction (PCR), or to isothermal primer extension reactions, such as in transcription mediated amplification reactions (e.g., TMA), using a pair of primers having a 5' segment, a 3' segment, and optionally a cushion segment between the 5' and 3' segments, as exemplified by FIG. 12 (the cushion segment is represented by AAAAAA). Both primers have a 5' phosphate group. The primers hybridize to opposing strands of the target nucleic acid and amplification with the primers results in a linear amplification product in which a segment of the target nucleic acid is flanked by the primers duplexed with their complementary segments (FIG. 12). The number of cycles in a PCR-like cycled extension reaction can be the minimum number of cycles needed to incorporate both primers into the product, or can be many cycles to cause amplification of the product containing the incorporated primers. Regardless of the number of cycles, any product of such a reaction incorporating a target nucleic acid and the primers is referred to as an amplicon or an amplification product. The amplification product is digested with a nucleic acid polymerase with 3' to 5' exonuclease activity in the presence of the nucleobase unit(s) of types that are complements of the cushion segments. The exonuclease activity of the polymerase digests at least some of the complements of the 5' segments of the primers. Progression of the exonuclease digestion along the nucleic acid strand stops upon reaching a position having one of the nucleobase units present in the digestion reaction, which can be located in the complement of a cushion segment or in the target nucleic acid segment (see FIG. 12, showing termination when exonuclease digestion reaches the first T of the complement of a cushion segment). After exonuclease digestion, the amplified product has two overhanging 5' segments (i.e., sticky ends) at both ends. Two overhanging 5' segments can have the same or different sequences. Preferably, the two overhanging 5' segments are not complementary. One or more adaptors having an overhanging 5' region complementary to the overhanging 5' segments in the amplified product are annealed to the amplified product. For example, two adaptors as shown in FIG. 12, each having a 5' overhanging region complementary to one of the overhanging 5' segments in the amplified product, are annealed to the amplified product. The 3' region of the adaptor is a stem-loop structure. Each of the 5' regions of the adaptors has a 5'-phosphate group. Because both the 5' ends of the digested amplified products and the adaptors are phosphorylated, the 5' phosphate groups are ligated to an adjacent 3' hydroxyl group in either the 3' region of the adaptor or the 3' ends of the digested amplified products (FIG. 12).

1. Primers

Method 13 employs a pair of forward and reverse primers hybridizing to opposing strands of a target nucleic acid (if double-stranded) or to a target nucleic acid and its complementary strand, if the target nucleic acid is single-stranded. Both primers include, in 5' to 3' direction, a 5' segment and a 3' segment. The 3' segments are target-binding segments that are complementary to the target nucleic acid (as is the case for conventional PCR primers). Exemplary lengths for the 3' segments are at least 3, 5, 10, 15 or 20 nucleobases units and optionally up to 30, 40 or 50 including all permutations of upper and lower limits. The spacing of the primers with respect to the target nucleic acid defines a segment of the target nucleic acid that is amplified and available for sequencing, amplification, and so forth.

The 5' segments can have the same or different sequences. Preferably, the two overhanging 5' segments are not complementary to one another in opposing orientations. The 5' segments and their complements can be designed so that nucleobase units to be digested from the complements of the 5' segments in a subsequent step are different from nucleobase units supplied to a polymerase with 3'-5' exonuclease activity. The 5' segments can also include one or more non-canonical nucleobase units as well instead of canonical nucleobase units.

Preferably, both primers have a 5' phosphate group. Alternatively, nucleic acids amplified using primers not having a 5' phosphate group, designed for use in multiple platforms, can be treated with a polynucleotide kinase (PNK, e.g., a T4 PNK) to transfer a phosphate group onto the 5'-end of the amplified nucleic acids.

Preferably, one or, more preferably both primers include a cushion segment between the 5' segment and the 3' segment. The nucleobase unit(s) in the cushion segment are of type(s) different than the nucleobase units in the 5' segments. Usually, the nucleobase units in the cushion segments are a single type of canonical nucleobase unit or two complementary types of canonical nucleobase units. For example, if the nucleobase units in the 5' segments are T, G and C, then the nucleobase units in the cushion segments can be A only. If the nucleobase units in the 5' segments are G and C, then the nucleobase units in the cushion segments can be A only, or T/U only, or both A and T/U. The cushion segment can be a homo-oligomeric segment (containing a single type of nucleobase) or a hetero-oligomeric segment. Examples of homo-oligomeric cushion segments include 5'-G-G-3', 5'-T-T-T-3', and 5'-C-C-C-3'. Optionally, one or more non-canonical nucleobase units can be included in the cushion segments, as well as or instead of the canonical nucleobase types included. The cushion segments are intended to terminate exonuclease digestion as further described below. Cushion segments can sometimes contain at least 1, 2, 3, 4, 5, or 6 nuclease base units, and optionally up to 10 nucleobase units including all permutations of lower and upper limits. Preferably cushion segments have 4-6 nucleobase units. In some cases, cushion segments have 10-20, 20-30 or more nucleobase units.

The cushion segments can be of the same or different lengths including a design in which one primer has a cushion segment and the other does not.

Optionally, primers can further include a barcode segment, for example, embedded in a pattern of a 5' segment or a cushion segment. Barcodes are differentiable sequences useful for identifying the origin of particular target segment. Barcodes are useful for sequencing pooled samples. For example, samples from two different sources can be independently amplified using primers having a unique barcode segment for each sample from a source. The amplified samples are then pooled and sequenced in a combined reaction. The unique sequences of the barcode segments identify the source of each sequenced sample.

2. Adaptors

The present methods employ one or more adaptors having a stem-loop structure. The adaptors have a stem-loop 3' region and a 5' region. The 5' region of the adaptor is complementary to one or both of the 5' segment(s) of the primers. The 3' segment forms a stem-loop structure, i.e., a double stranded stem structure coupled to the single stranded loop. The 5' end of the 5' region is phosphorylated. The 3' end of the 5' region connects with the 5' end of the stem-loop.

The two 5' regions of the adaptor pair can be the same or different. The 5' segment from the first primer and the 5' segment from the second primer can be the same or different. Accordingly, one or two adaptors can be used in combination with a pair of primers having the same or different 5' segments. For example, in cases where the two 5' segments have different sequences and/or lengths, two adaptors having different 5' regions can be used, each of the 5' regions being complementary to one of the 5' segments.

To seal the nicks remaining after annealing the adaptor to the digested nucleic acids, the 5' ends of the 5' region of the adaptor and the 5' ends of the primers are phosphorylated. Adaptors having phosphorylated 5' ends can be routinely synthesized, e.g., by incorporating a phosphorylated nucleotide. For adaptors not having phosphorylated 5' ends, a phosphate group can be added to the 5' end using a PNK, as discussed above.

3. Exonuclease Reaction

When a DNA template is used, a variety of DNA polymerases with 3' to 5' exonuclease activity can be used. Preferably, a T4 DNA polymerase is used. The exonuclease activity of the nucleic acid polymerase digests at least parts (one part on each strand) of the amplified nucleic acid complementarity to the 5' segments of the primers. Preferably the nuclease activity digests the entire parts complementary to the 5' segments of the primers. When the primers contain a cushion segment, the exonuclease activity digests the complements of the 5' segments, and terminates at (i.e., immediately before the first nucleobase unit of the cushion) or in the complements of the cushion segments in the amplified nucleic acid. When the primers do not contain a cushion segment, the exonuclease digestion terminates in the target region at a position having a nucleobase unit of the same type as is supplied with the polymerase.

4. Ligation

The closed nucleic acids contains nicks between the 5' primer ends or the 5' regions of the adaptors and adjacent hydroxyl groups. The nick in the closed nucleic acids can be ligated using a nucleic acid ligase. The ligase joins a 5' phosphate group from the 5' prime ends or the 5' regions of the adaptors to an adjacent hydroxyl.

In some cases, the polymerase 3'-5' exonuclease and ligase reactions can be performed sequentially (exonuclease first) or both enzymes can be supplied together so that once the exonuclease digestion is complete the digested nucleic acids can be annealed to adaptors and ligated. In some cases, a thermophilic nucleic acid ligase and a non-thermophilic polymerase can be used. Once the digestion is complete, the temperature can be (but need not be) increased, e.g., over 40, 50, 60, or 70° C. to inactivate the polymerase, whereas the thermophilic ligase remains active at the elevated temperature. An additional or alternate heat inactivation can carried out after both exonuclease digestion and ligation are complete and before sequencing, amplification or other procedure.

The closed nucleic acid structures of method 13 can be purified from linear products using standard methods such as gel purification or affinity chromatography.

IX. Method 14

Generating a Closed Nucleic Acid Structure Using Terminal Deoxynucleotidyl Transferase Method 14 generates a closed nucleic acid structure utilizing terminal deoxynucleotidyl transferase (TdT). Method 14 employs a pair of forward and reverse primers hybridizing to opposing strands of a target nucleic acid (if double-stranded) or to a target nucleic acid and its complementary strand, if the target nucleic acid is single-stranded. Any suitable primers having 5' phosphate group can be used. An adaptor can then be annealed onto the extended nucleic acid to form a closed nucleic acid structure.

Figure 13:
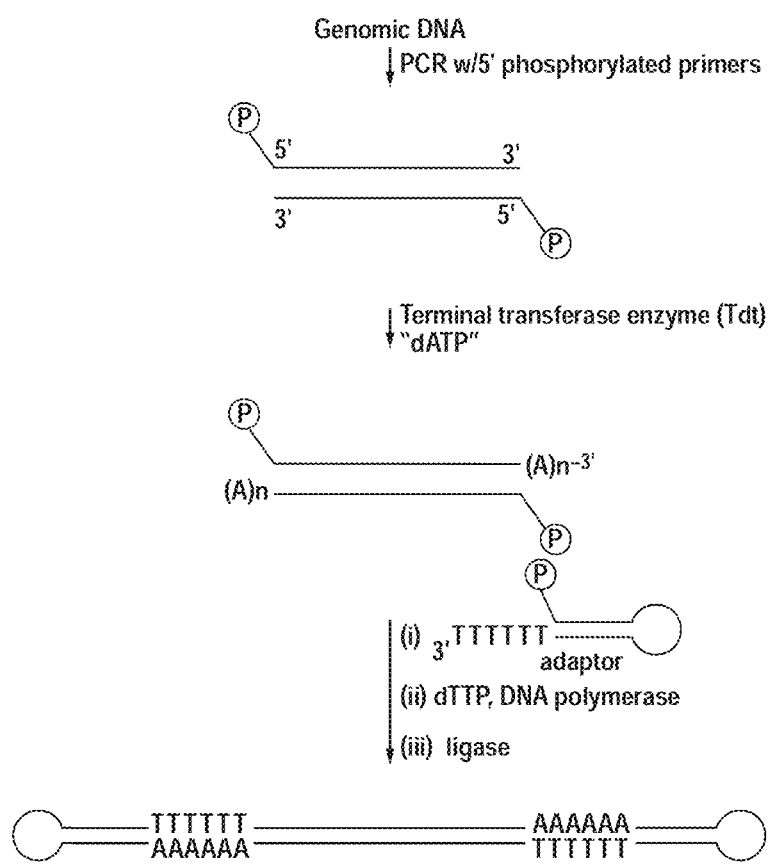
FIG. 13 illustrates an exemplary form of method 14 for generating a closed nucleic acid structure using a terminal deoxynucleotidyl transferase and a pair of adaptors.

An exemplary form of the methods is shown in FIG. 13. A target nucleic acid is subjected to cycled primer extension reactions, such as in polymerase chain reaction (PCR), or to isothermal primer extension reactions, such as in transcription mediated amplification reactions (e.g., TMA), using a pair of 5'-phosphorylated primers as exemplified by FIG. 13. Amplification with the primers results in an amplification product having phosphate group at 5'-ends. The amplification product is then treated with TdT in the presence of a first deoxynucleotide (e.g., dATP as shown in FIG. 13). The TdT enzyme catalyzes addition of at least one first deoxynucleotide to the 3'-end of the amplification product, creating a homo-oligomeric tail at the 3'-end of the amplification product, e.g., a $-(A)_n$- tail. The numbers of first deoxynucleotides added to the 3'-end can be modulated by, e.g., the duration of treatment with TdT. After TdT treatment, the amplified product has two overhanging 3' segments (i.e., sticky ends). One or more adaptors having overhanging 3' segments complementary to the overhanging 3' segments in the amplified product are annealed to the amplified product. For example, in FIG. 13, an adaptor having a 3' overhanging $-(T)_m$- segment is annealed to the $-(A)_n$- tail in the amplified product. The 5' segment of the adaptor is a stem-loop structure having a 5'-phosphate group. The $-(A)_n$- tail and the $-(T)_m$- segment may or may not be of equal lengths. In some case, the $-(A)_n$- tail is longer than the $-(T)_m$- segment, and in other cases, the -(T)$_m$- segment is longer. Regardless of the relative lengths of the -(A)$_n$- tail and the -(T)$_m$- segment, a gap in the adaptor-capped amplified product, e.g., due to the unequal lengths of -(A)$_n$- or -(T)$_m$- can be filled by a nucleic acid polymerase (e.g., a DNA polymerase) in the presence of the first deoxynucleotide (e.g., dATP) and/or a second deoxynucleotide that is complementary to the first deoxynucleotide (e.g., dTTP). Because both the 5' ends of the amplified products and the adaptors are phosphorylated, the 5' phosphate groups are ligated to an adjacent 3' hydroxyl group in either the -(A)$_n$- tail or the -(T)$_m$- segment.

In method 14, the terminal 3'-hydroxyl of a DNA strand (e.g., from an amplified product) is extended by a TdT to form a homo-oligomeric tail comprising a first deoxyribonucleotide. Preferably, the TdT extension is carried out in the presence of a single deoxyribonucleotide, canonical or non-canonical, and the extended tail on the 3' end is homo-oligomeric. The numbers of first deoxyribonucleotides added to the homo-oligomeric tail can be modulated by changing reaction conditions, e.g., by varying the duration of TdT treatment. Typically, the homo-oligomeric tail comprises 3-50, 3-20, or 3-10 nucleobase units. Most preferably, the homo-oligomeric tail comprises five nucleobase units.

Alternatively, the TdT extension is carried out in the presence of more than one deoxyribonucleotides, all of which have same or similar hybridizing properties. For example, an amplified product can be extended at 3'-end in the presence of both dUTP and dTTP, both of which are complementary to dATP. The first deoxyribonucleotide can be labeled or detectably tagged.

Method 14 employs an adaptor structure having a 3'-portion comprising a second deoxyribonucleotide which is complementary to the homo-oligomeric tail comprising a first deoxyribonucleotide. The 3'-portion of the adaptor can be designed to have about the same length as that of a desired homo-oligomeric tail (e.g., 3-50, 3-20, 3-10, 4-6, or more preferably about 5 nucleobase units). The adaptor further comprises a 5' portion that forms a stem-loop structure (i.e., a hairpin loop) by itself. Preferably, the 5' portion of the adaptor does not hybridize to the homo-oligomeric tail, e.g., it does not contain a sequence complementary to the homo-oligomeric tail. Thus, in the presence of TdT-extended target nucleic acids, the 5' portion maintains its stem-loop structure. Preferably, adaptors having phosphorylated 5' ends.

The TdT extension produces a heterogeneous population of nucleic acids having homo-oligomeric tails of different lengths, some of which are longer than the 3'-portion of the adaptor, others of which are shorter. The gaps between the adaptors and the Tdt-extended nucleic acids can be filled by a nucleic acid polymerase (e.g., a DNA polymerase such as Klenow or Taq DNA polymerase), preferably in the presence of two deoxyribonucleotides: a first deoxyribonucleotide that is used in making the homo-oligomeric tails and a second deoxyribonucleotide that is complementary to the first deoxyribonucleotide.

Any remaining nicks in the template can be sealed using a nucleic acid ligase. To seal the nicks remaining after annealing the adaptor to the Tdt-extended nucleic acids, all 5' ends of both components are required to be phosphorylated. For adaptors or the Tdt-extended nucleic acids not having phosphorylated 5' ends, a phosphate group can be added to the 5' end using a polynucleotide kinase (PNK). The closed nucleic acid structures of method 14 can be purified from linear products using standard methods such as gel purification or affinity chromatography.

X. Method 15

Generating a Closed Nucleic Acid Structure Following Polymerase Extension of at Least One Stem-Loop Primer At a general level, method 15 involves two main steps, or sets of steps. In the initial step, or set of steps, a nucleic acid having defined ends is provided. In the subsequent step, or set of steps, a stem-loop primer is annealed to the nucleic acid having defined ends and subsequently extended, thereby providing an extended nucleic acid strand that includes the stem-loop primer and can be readily converted into a closed nucleic acid structure.

Figure 14A:
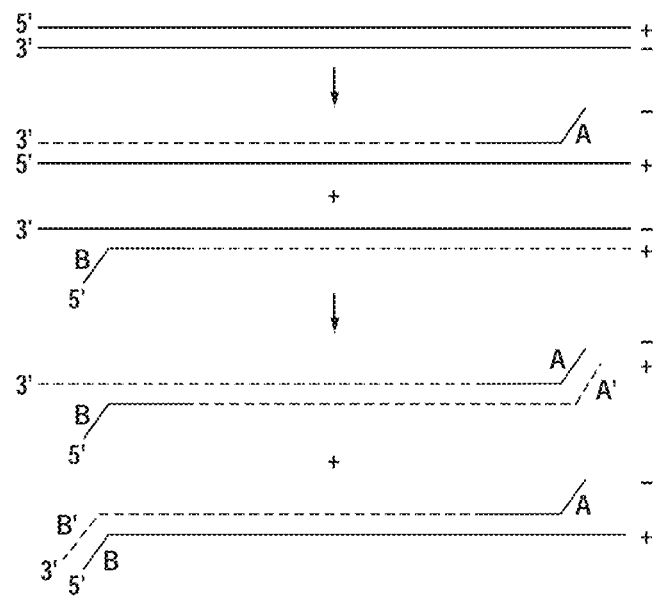
FIGS. 14A, B illustrate an exemplary form of method 15 for generating a closed nucleic acid structure comprising an initial step of primer amplification (FIG. 14A) and a subsequent step of primer extension from a pair of stem-loop primers (FIG. 14B).

FIGS. 14A and B show an exemplary embodiment of method 15 in which a nucleic acid having defined ends is obtained (e.g., produced) by amplification. In the initial step, an amplified nucleic acid comprising a region of interest in a target nucleic acid is generated by mixing the target nucleic acid with a pair of linear primers under amplification conditions. The linear primers each have a 5' segment and a 3' segment, with the 3' segments being target-binding segments and the 5' segments providing sequence tags. The resulting amplified nucleic acid (i.e., nucleic acid having defined ends) is double-stranded and includes a segment of the target nucleic acid (i.e., region of interest) flanked by the linear primers and their complementary segments. FIG. 14A.

Figure 14B:
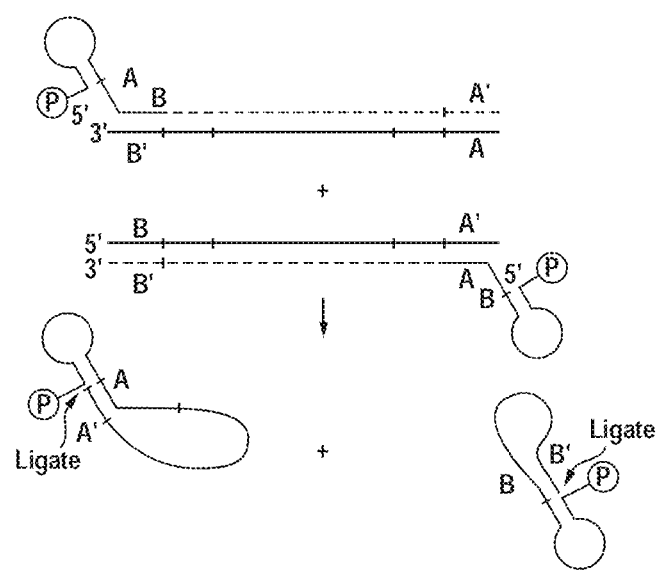

In the subsequent set of steps, the amplified nucleic acid is denatured to yield single strands of amplified nucleic acid. A pair of stem-loop primers are then annealed to the strands of the denatured amplified nucleic acid (FIG. 14B). Each of the stem-loop primers has a 5' phosphate, a 5' segment having a stem-loop structure, and a 3' segment having two sub-segments, one proximal to the 5' segment and one distal to the 5' segment. The proximal 3' sub-segment of a first stem-loop primer of the pair has a common sequence with the 5' segment of a first primer of the linear primer pair (from the initial step), and the distal 3' sub-segment of the first stem-loop primer has a common sequence with the 5' segment of the second primer of the linear primer pair. Likewise, the proximal 3' sub-segment of the second stem-loop primer of the pair has a common sequence with the 5' segment of the second primer of the linear primer pair (from the initial step), and the distal 3' sub-segment of the second stem-loop primer has a common sequence with the 5' segment of the second primer of the linear primer pair.

After the distal 3' sub-segment of each stem-loop primer anneals to a corresponding 3' end segment (e.g., the complement of a 5' segment of a linear primer) on one of the strands of the denatured amplified nucleic acid, polymerase-mediated extension from the stem-loop primers produces extended strands, each duplexed to a strand of the denatured amplified nucleic acid. Each extended strand includes, from 5'-3', a stem-loop primer, a strand of the target nucleic acid, and a segment complementary to a primer of the linear primer pair. At the 5' end of each extended strand there is a 5' phosphate group (i.e., originating from the end of a stem-loop primer) and at the 3' end there is a 3' hydroxyl (i.e., originating from the end of a segment complementary to a linear primer). The extended strands are denatured to separate them from the strands of the amplified nucleic acid. The denatured extended strands are then allowed to intramolecularly hybridize. During the process of intramolecular hybridization, the segment at the 3' end of each extended strand (i.e., the segment complementary to the 5' segment of one of the linear primers) hybridizes to the 3' proximal segment of the stem-loop primer, bringing the 5' phosphate group adjacent to the 3' hydroxyl group, and thereby forming a nucleic acid structure having a circular topology with a nick separating the 5' phosphate group from the 3' hydroxyl. FIG. 14B. Ligation of the nick produces a closed nucleic acid structure.

The embodiment of method 15 shown in FIGS. 14A, B is highly versatile. Because of the sequence tags appended onto the ends of the target nucleic acid during the initial amplification step, the method is readily adaptable for amplification and generation of multiple closed nucleic acid structures in the same set of reactions (e.g., multiplexed preparation and analysis). Suitable sequence tags can be selected based on desirable characteristics for downstream manipulation, such as similar annealing temperatures and minimal cross-hybridization between the sequence tags. Exemplary tag sequences exhibiting desirable characteristics include the set of xTAG® sequences available from Luminex™. However, any suitable sequence tags can be used.

The target nucleic acid can be double-stranded (as shown in FIG. 14A) or single-stranded. The target nucleic acid can be any target nucleic acid described herein, including genomic DNA, cloned fragments, including large nucleic acid clones (e.g., cosmids, BACs, YACs and so forth), amplified fragments (e.g., amplified by PCR), cDNA, RNA, and so forth. When the nucleic acid having defined ends (e.g., the "amplified nucleic acid" described above in connection with FIG. 14A) is obtained by amplification, two, three, or more rounds of amplification can be performed, depending on abundance of the target nucleic acid and the final objective of the method. For example, if the target nucleic acid is double-stranded, two rounds of amplification can be sufficient to allow for formation of closed nucleic acid structures for each strand of the target nucleic acid. Alternatively, if the target nucleic acid is single-stranded, at least three rounds of amplification are required to allow for formation of closed nucleic acid structures for both the target nucleic acid and its complementary sequence. Additional rounds of amplification can be performed, as desired, for low abundance target nucleic acids.

The primers used to amplify the target nucleic acid can be, e.g., linear primers, as described herein. Typically, the primers include a 3' segment and a 5' segment, wherein the 3' segment is a target-binding segment and the 5' segment includes a sequence tag. The sequence tag can be relatively short, e.g., consisting of less than 10 nucleobase units (e.g., consisting of 1, 2, 3, 4, or 5 nucleobase units). Short sequence tags preferably have a high GC content. Alternatively, the sequence tag can be relatively long, e.g., consisting of at least 10 nucleobase units (e.g., at least 15, 20, 25 or more nucleobase units). The longer sequence tags can be highly selective, hybridizing only poorly or not at all to other nucleic acids (e.g., the target nucleic acid) present in the amplification reaction. Examples of selective sequence tags include, e.g., xTAG®'s, as described above. Alternatively, the primers used to amplify the target nucleic acid can include a 3' segment and a 5' segment, wherein one or both of the 5' segments include a sequence complementary to a portion of the target nucleic acid. For example, the 5' and 3' segments of an amplification primer can be complementary to adjacent portions of the target nucleic acid (e.g., as is typical for conventional PCR primers). A 5' segment that includes a sequence complementary to a portion of the target nucleic acid can also include additional nucleobase units, e.g., located at the 5' end of the segment.

Another possibility is for the 5' and 3' segments of an amplification primer to be complementary to non-adjacent portions of the target nucleic acid. For example, the 5' segment can be complementary to a portion of the target nucleic acid that is distal to and on the opposite (or complementary) strand relative to the portion of the target nucleic acid complementary to the 3' segment of the primer. Optionally, one or both of the primers used to amplify the target nucleic acid include a 5' phosphate group. Optionally, one or both of the primers used to amplify the target nucleic acid is attached to a solid support, such as glass, a polymeric surface, a microchip, a column, or a bead. Attaching primers to a solid support can facilitate the purification of desirable intermediates, such as extended strands that include a stem-loop primer.

In the initial step, or set of steps, of method 15, a nucleic acid having defined ends can be obtained by means other than amplification. For example, a primer and a blocker oligonucleotide can be used to generate a single-stranded nucleic acid having defined ends, e.g., as described below in connection with variation 4 of Method 16 and depicted in FIG. 15G. Alternatively, nucleic acid having defined ends can be generated by digesting double-stranded target nucleic acids with restriction endonucleases. Optionally, single-stranded overhangs generated by the endonucleases are filled-in or removed, e.g., using standard techniques, thereby generating blunt-ended nucleic acid. Preferred restriction endonucleases include endonucleases that produce blunt ends (e.g., SmaI, StuI, ScaI, EcoRV) or 3' overhangs (e.g., NotI, BamHI, EcoRI, SpeI, XbaI, HaeIII, TaqI, AluI), but restriction endonucleases that produce 5' overhangs can also be used.

Although the exemplary method 15 described above and depicted in FIG. 14 includes the use of a pair of stem-loop primers, the method can be readily practiced using just a single stem-loop primer. When a single stem-loop primer is used, typically only one strand of the target nucleic acid (i.e., the strand complementary to the strand to which the stem-loop primer hybridizes) are incorporated into a closed nucleic acid structure. Accordingly, by performing two different sets of reactions, e.g., in parallel, each using a single stem-loop primer that hybridizes to only one strand of the nucleic acid having defined ends, both strands of the target nucleic acids (or the target nucleic and its complementary strand) can be incorporated into closed nucleic acid structures. However, if the single stem-loop primer binds to both strands of the nucleic acid having defined ends, which can happen, e.g., when primers used to amplify the target nucleic acid have 5' segments that have a common sequence, then both strands of the target nucleic acid can be incorporated into closed nucleic acid structures in a single reaction. To the extent that amplification primers used in the initial step of the method interfere with hybridization of stem-loop primers to the amplified nucleic acid strands, excess stem-loop primers can be used.

The stem-loop primer or primers used in the method can be, e.g., any stem-loop primer described herein. Typically, each stem-loop primer includes a 5' phosphate group, a 5' segment having a stem-loop structure, and a 3' segment. The 3' segment can include, e.g., two sub-segments, one proximal to the 5' segment and one distal to the 5' segment. The distal 3' sub-segment can be complementary to a 3' end segment of one strand of the nucleic acid having defined ends (provided by the initial step, or set of steps, of the method). For example, the distal 3' sub-segment can have a common sequence with the 5' segment of a primer used to amplify the target nucleic acid in the initial step. Alternatively, the distal 3' sub-segment can be complementary to a segment internal to a 3' end segment of the nucleic acid having defined ends. For example, the distal 3' sub-segment can have a common sequence with the 3' segment of a primer used to amplify the target nucleic acid in the initial step. Likewise, the proximal 3' sub-segment can be complementary to a 3' end segment of the nucleic acid having defined ends. For example, the proximal 3' sub-segment can be complementary to a 3' end segment of a strand of the nucleic acid having defined ends which is complementary to the strand that the distal 3' sub-segment hybridizes to (e.g., the proximal 3' sub-segment can share a common sequence with the 5' segment of a primer used to amplify the target nucleic acid in the initial step). As an alternative to having distinct sub-segments, the entire 3' segment of a stem-loop primer can be complementary to a 3' end segment of one strand of the nucleic acid having defined ends. For example, the entire 3' segment can have a common sequence with the 5' segment of a primer used to amplify the target nucleic acid in the initial step, or the entire 3' segment can be complementary to a segment internal to a 3' end segment of the nucleic acid having defined ends (e.g., the entire 3' segment can have a common sequence with the 3' segment of a primer used to amplify the target nucleic acid in the initial step). The 5' and 3' segments of a stem-loop primer can be directly linked to each other (e.g., with no intervening segment) or they can be linked by an intervening segment. A suitable intervening segment can be, e.g., a poly-T sequence (e.g., a sequence of 1, 2, 3, or 4 T nucleobase units).

Denaturation of duplex nucleic acids (e.g., template, nucleic acids having defined ends, and extended nucleic acids including stem-loop primers) and annealing of primers can be achieved using standard techniques, such as varying temperature and/or ionic strength of the buffer.

Variation 1

In a variation of method 15, the initial and subsequent steps (or sets of steps) can be combined. For example, the target nucleic acid can be amplified using one linear primer and one stem-loop primer. After generating an amplified nucleic acid with defined ends that includes a segment of the target nucleic acid, the amplified nucleic acid is denatured and the strands are allowed to hybridize intramolecularly, thereby forming a nucleic acid structure having a circular topology with a nick separating the 5' phosphate group from the 3' hydroxyl, as shown in FIG. 14B. Ligation of the nick produces a closed nucleic acid structure. If the stem-loop primer includes a 5' phosphate but the linear primer does not, then only the target nucleic acid strand complementary to the strand that the stem-loop primer hybridizes are recovered in a closed nucleic acid structure. If the linear primer includes a 5' phosphate but the stem-loop primer does not, then only the target nucleic acid strand complementary to the strand that the linear primer hybridizes to are recovered. If both primers include a 5' phosphate, then both strands of the target nucleic acid are recovered from a single reaction.

The linear and stem-loop primers used in this variation of method 15 can, e.g., be as described above. Typically, the linear primer includes a 5' segment, a 3' segment, and optionally a 5' phosphate group, wherein the 3' segment is a target-binding segment and the 5' segment includes a sequence tag. Other arrangements for the linear primer are also possible (e.g., both the 3' and 5' segments can be target binding segments). Typically, the stem-loop primer includes a 5' segment having a stem-loop structure, a 3' segment, and optionally a 5' phosphate group. The 3' segment can include proximal and distal sub-segments or not, as discussed above.

XI. Method 16

Generating a Closed Nucleic Acid Structure Following Amplification/Primer Extension Followed by Ligation to a Stem-Loop Primer At a general level, method 16 involves two main steps, or sets of steps. In the initial step, or set of steps, a nucleic acid having defined ends is provided. In the subsequent step, or set of steps, a stem-loop adaptor is annealed to one strand of the nucleic acid having defined ends, thereby providing a partially duplexed, two-stranded intermediate structure that can be readily converted into a closed nucleic acid structure by ligation.

Figure 15A:
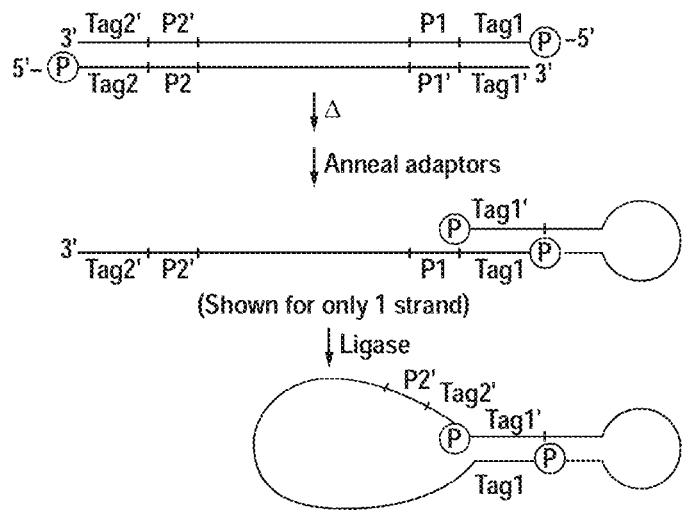
FIGS. 15A-H illustrates exemplary forms of method 16 for generating a closed nucleic acid structure comprising an initial step, or set of steps, of amplification and/or primer extension, and a subsequent set of steps wherein a stem-loop adaptor is ligated to the amplified and/or extended nucleic acid.

FIG. 15A shows an exemplary embodiment of method 16 in which a nucleic acid having defined ends is obtained (e.g., produced) by amplification. Basically, in the initial step, an amplified nucleic acid comprising a region of interest in a target nucleic acid is generated by mixing the target nucleic acid with a pair of linear primers under amplification conditions. The linear primers each have a 5' phosphate group, a 5' segment, and a 3' segment. The 3' segments are target-binding segments and the 5' segments include sequence tags. The resulting amplified nucleic acid is double-stranded and includes a segment (e.g., region of interest) of the target nucleic acid flanked by the linear primers and their complementary segments. Each strand of the amplified nucleic acid further includes a 5' phosphate group and a 3' end hydroxyl.

In the subsequent set of steps, the amplified nucleic acid is denatured to yield single strands of amplified nucleic acid. A stem-loop adaptor is then annealed to a 5' end segment of one of the denatured amplified nucleic acid strands. The stem-loop adaptor has, from 5' to 3', a 5' phosphate, a 5' segment, a 3' segment having a stem-loop structure, and a 3' end hydroxyl. The 5' segment of the stem-loop adaptor is complementary to the 5' segment of the first primer of the linear primer pair (from the initial step). Annealing of the 5' segment of the stem-loop adaptor to the 5' end segment of one strand of the amplified nucleic acid (i.e., the 5' segment of the first linear primer) generates a partially duplexed, two-stranded intermediate structure, wherein the 5' phosphate group from the amplified nucleic acid strand is adjacent to the 3' end hydroxyl of the stem-loop adaptor (a nick separates the 5' phosphate group from the 3' end hydroxyl). The partially duplexed, two-stranded intermediate structure is then treated with ligase. The ligase seals the nick between the 5' phosphate group of the amplified nucleic acid strand and the 3' end hydroxyl of the stem-loop adaptor and, in addition, links the 5' phosphate group of the stem-loop adaptor to the 3' end hydroxyl of the amplified nucleic acid strand, thereby forming a closed nucleic acid structure.

The embodiment of method 16 shown in FIG. 15A is highly versatile. Because of the sequence tags appended onto the ends of the target nucleic acid during the initial amplification step, the method is readily adaptable for amplification and generation of multiple closed nucleic acid structures in the same set of reactions (e.g., multiplexed preparation and analysis). Suitable sequence tags can be selected based on desirable characteristics for downstream manipulation, such as similar annealing temperatures and minimal cross-hybridization between the sequence tags. Exemplary tag sequences exhibiting desirable characteristics include the set of xTAG® sequences available from Luminex™. However, other suitable sequence tags can be used.

The target nucleic acid can be double-stranded (as shown in FIG. 15A) or single-stranded. The target nucleic acid can be any target nucleic acid described herein, including genomic DNA, cloned fragments, including large nucleic acid clones (e.g., cosmids, BACs, YACs, and so forth), amplified fragments (e.g., amplified by PCR) such as cDNA, RNA and so forth. When the nucleic acid having defined ends (e.g., the "amplified nucleic acid" described above in connection with FIG. 15A) is obtained by amplification, two, three, or more rounds of amplification can be performed, depending on abundance of the target nucleic acid and the final objective of the method. For example, if the target nucleic acid is doublestranded, two rounds of amplification can be sufficient to allow for formation of closed nucleic acid structures for each strand of the target nucleic acid. Alternatively, if the target nucleic acid is single-stranded, at least three rounds of amplification are required to allow for formation of closed nucleic acid structures for both the target nucleic acid and its complementary sequence. Additional rounds of amplification can be performed, as desired, for low abundance target nucleic acids.

The primers used to amplify the target nucleic acid can be, e.g., linear primers, as described above. The primers can include a 3' segment and a 5' segment, wherein the 3' segment is a target-binding segment and the 5' segment includes a sequence tag. The sequence tag can be relatively short, e.g., consisting of less than 10 nucleobase units (e.g., consisting of 1, 2, 3, 4, or 5 nucleobase units). Short sequence tags preferably have a high GC content. Alternatively, the sequence tag can be relatively long, e.g., consisting of at least 10 nucleobase units (e.g., at least 15, 20, 25 or more nucleobase units). The longer sequence tags can be highly selective, hybridizing only poorly or not at all to other nucleic acids (e.g., target nucleic acid) present in the amplification reaction. Examples of selective sequence tags include, e.g., xTAG®'s, as described above. A 5' segment that includes a selective sequence tag, such as an xTAG®, can also include additional nucleobase units, e.g., located at the 5' end of the 5' segment. One or both of the primers can further include an intervening segment (e.g., a sequence of 1, 2, 3, 4, or more nucleobase units) that links the 3' and 5' segments. Such an intervening segment can, e.g., share a common sequence with the sequence at the 5' end of the other primer in the pair (e.g., the 5' segment of the other primer, or a 5'-most sub-segment thereof) and thereby facilitate the formation of a closed nucleic acid structure (e.g., by hybridizing to the sequence at the 3' end of the amplified nucleic acid strand in the partially duplexed, two-stranded intermediate structure).

Alternatively, the primers used to amplify the target nucleic acid can include a 3' segment and a 5' segment, wherein the 5' segment of one or both primers has a sequence complementary to a portion of the target nucleic acid. For example, the 5' and 3' segments of an amplification primer can be complementary to adjacent portions of the target nucleic acid (e.g., as is typical for conventional PCR primers). A 5' segment that has a sequence complementary to a portion of the target nucleic acid can also include additional nucleobase units, e.g., located at the 5' end of the segment.

Another possibility is for the 5' and 3' segments of an amplification primer to be complementary to non-adjacent portions of the target nucleic acid. For example, the 5' segment can be complementary to a portion of the target nucleic acid that is distal to and on the opposite (or complementary) strand relative to the portion of the target nucleic acid complementary to the 3' segment of the primer. This latter arrangement, in particular, can be conducive to the formation of closed nucleic acid structures.

Optionally, one or both of the primers used to amplify the target nucleic acid include a 5' phosphate group. If only one of the primers includes a 5' phosphate group, then only the strand of the amplified nucleic acid that includes the primer with the 5' phosphate group can be readily incorporated into a closed nucleic acid structure. If neither of the amplification primers includes a 5' phosphate group, then the amplified nucleic acid can be treated (e.g., enzymatically) to add 5' phosphate groups at the ends of the strands.

Figure 15B:
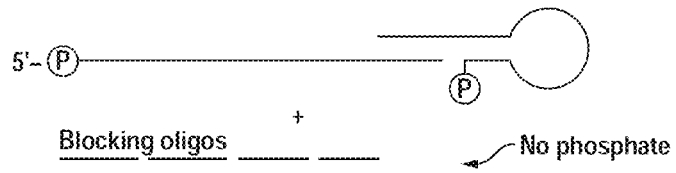

Optionally, one or both of the primers used to amplify the target nucleic acid can be attached to a solid support, such as glass, a polymeric surface, a microchip, a column, or a bead. Having one of the primers attached to a solid support can facilitate separation of the strands of the amplified nucleic acid, which may, in turn, facilitate the formation of partially double-stranded, two-stranded nucleic acid structures and the corresponding closed nucleic acid structures. Alternative means of facilitating the formation of partially double-stranded, two-stranded nucleic acid structures and the corresponding closed nucleic acid structures include, e.g., the addition of blocking oligonucleotides that can bind to a strand of the amplified nucleic acid other than the strand to which the stem-loop oligonucleotide is binding (e.g., as shown in FIG. 15B).

In the initial step, or set of steps, of method 16, a nucleic acid having defined ends can be obtained by means other than amplification. For example, a primer and a blocker oligonucleotide can be used to generate a single-stranded nucleic acid having defined ends, e.g., as described below (see variation 4 of method 16) and depicted in FIG. 15G. Alternatively, nucleic acid having defined ends can be generated by digesting double-stranded target nucleic acids with restriction endonucleases. Optionally, single-stranded overhangs generated by the endonucleases are filled-in, e.g., using standard techniques. Preferred restriction endonucleases include endonucleases that cut within palindromic sites and produce blunt ends (e.g., SmaI, StuI, ScaI, EcoRV) or 3' overhangs (e.g., NotI, BamHI, EcoRI, SpeI, XbaI, HaeIII, TaqI, AluI). Partial restriction endonuclease sites created at the ends of target nucleic acid fragments create short complementary sequences at the ends of each strand, which can facilitate the formation of closed nucleic acid structures, particularly as described below (e.g., for variation 2 of method 16).

Although the exemplary method 16 described above and depicted in FIG. 15A includes the use of a single stem-loop adaptor, the method can also be practiced using a pair of stem-loop adaptors. When a pair of stem-loop adaptors is used, both strands of the amplified nucleic acid (i.e., nucleic acid having defined ends) can be incorporated into a closed nucleic acid structure. Accordingly, by performing a single set of reactions that contain a pair of stem-loop adaptors or by performing two different sets of reactions, e.g., in parallel, each using a single stem-loop adaptor that hybridizes to only one strand of the amplified nucleic acid, both strands of the target nucleic acids (or the target nucleic and its complementary strand) can be incorporated into closed nucleic acid structures.

Figure 15C:
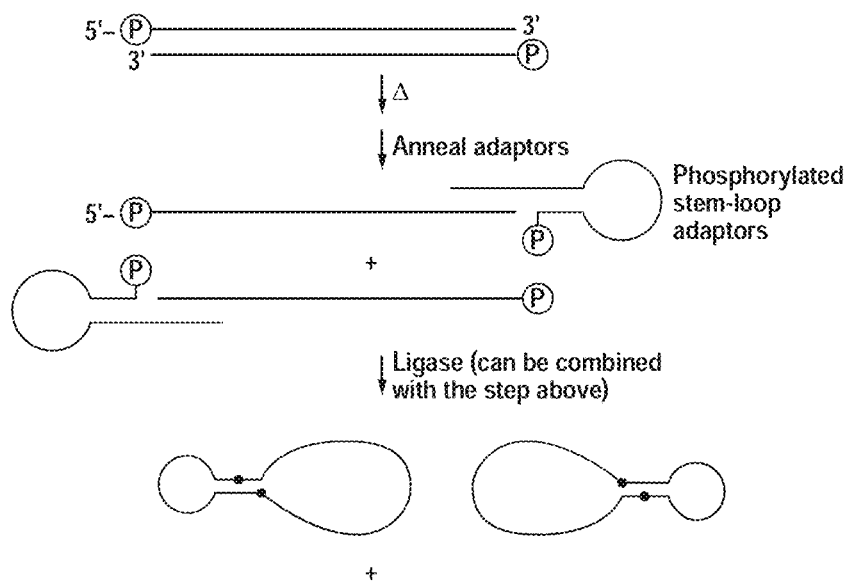

The stem-loop adaptor(s) used in the method can be, e.g., any stem-loop adaptor described herein. Typically, each stem-loop adaptor includes a 5' phosphate group, a 5' segment, a 3' segment, and a 3' end hydroxyl, wherein either the 5' or the 3' segment includes a sequence having a stem-loop structure. If the 3' segment includes a sequence having a stem-loop structure (e.g., as shown in FIGS. 15A and D), then the 5' segment can be complementary to a 5' end segment of one strand of the amplified nucleic acid (i.e., the nucleic acid having defined ends). Alternatively, if the 5' segment includes a sequence having a stem-loop structure (e.g., as shown in FIGS. 15C and E), then the 3' segment can be complementary to a 3' end segment of one strand of the amplified nucleic acid. The 5' and 3' segments of the stem-loop adaptor(s) can be directly linked to each other (e.g., with no intervening segment) or they can be linked by an intervening segment. An intervening segment can be particularly useful is the amplified nucleic acid is produced by amplification using a polymerase, such as Taq polymerase, that tends to add additional, non-template directed nucleobase units at the 3' end of a polymerized strand. Accordingly, a suitable intervening segment can be, e.g., a T nucleobase unit or a poly-T sequence (e.g., a sequence of 2, 3, or 4 T nucleobase units).

Denaturation of duplex nucleic acids (e.g., template, nucleic acids having defined ends, extended nucleic acids including stem-loop primers) and annealing of primers can be achieved using standard techniques, such as varying temperature and/or ionic strength of the buffer.

Variation 1

In a first variation of method 16, exemplified in FIG. 15C, the initial step of the method involves amplification of a portion of a target nucleic acid using a pair of linear primers that do not include sequence tags (e.g., the primers have 3' and 5' segments complementary to adjacent segments of the target nucleic acid). Of course, given a sufficient amount of target nucleic acid, such an amplification step can be replaced with a restriction endonuclease treatment step, optionally in combination with a fill-in step.

The variation of method 16 depicted in FIG. 15C further exemplifies the use of a pair of stem-loop adaptors in the subsequent set of steps. As depicted, each of the stem-loop adaptors includes a 3' segment that is complementary to a 3' end segment of one of the strands of amplified nucleic acid (i.e., nucleic acid having defined ends). However, stem-loop adaptors having a 5' segment that is complementary to a 5' end segment of one of the strands of amplified nucleic acid can be used instead. According to this variation of the method, within the same reaction mixture both strands of the amplified nucleic acid are incorporated into closed nucleic acid structures. Preferably, for each strand of amplified nucleic acid, the sequence immediately adjacent and internal to the 3' end segment (i.e., the segment that a stem-loop adaptor hybridizes to) is complementary to a sequence from the 5' end of the strand. Such complementarity improves the yield of closed nucleic acid structures produced by the method. The extent of complementarity can be limited, consisting of, e.g., 1, 2, 3, 4, or more nucleobase unit pairs. Complementarity between the sequences need not be 100% provided that at least the nucleobase unit immediately adjacent to the 3' end segment is capable of base pairing with the nucleobase unit at the 5' end of the strand. The junction between the 3' end segment and the sequence immediately adjacent on each strand of amplified nucleic acid can be readily selected so as to ensure that such limited complementarity exists.

Variation 2

Figure 15D:
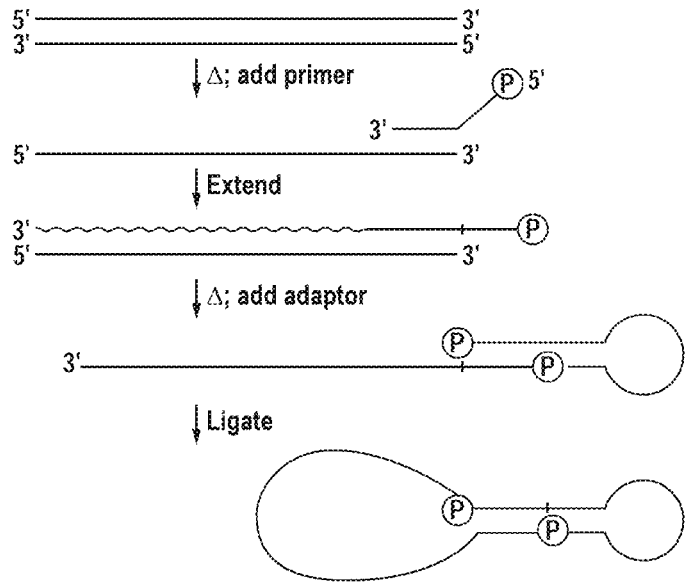

In a second variation of method 16, exemplified in FIG. 15D, the method includes an initial step of amplification of a portion of a target nucleic acid using a pair of linear primers that do not include sequence tags (e.g., the primers have 3' and 5' segments complementary to adjacent segments of the target nucleic acid). Following the amplification step, but prior to the steps involving the stem-loop adaptor, there is an intervening primer extension step involving a third primer. The third primer includes, from 5' to 3', a 5' phosphate group, a 5' segment, a 3' segment, and a 3' end hydroxyl, wherein the 3' segment is complementary to a 3' segment (e.g., a 3' end segment or a segment internal to the 3' end, as shown in FIG. 15F) of the amplified nucleic acid (i.e., the nucleic acid having defined ends). Thus, for example, the 3' segment of the third primer can have a common sequence with one of the amplification primers or a portion thereof (e.g., a 5' segment or an internal portion). The 5' segment of the third primer can include, e.g., a sequence tag, as described above. After annealing the third primer to one strand of the nucleic acid having defined ends, polymerase extension of the third primer produces a duplex nucleic acid having (1) a strand of the amplified nucleic acid and (2) an extended nucleic acid strand that includes, from 5' to 3', a 5' phosphate group, the third primer, a portion of the target nucleic acid, and a 3' end segment (e.g., the complement of one of the amplification primers). The extended strand is denatured to separate it from the strand of amplified nucleic acid. A stem-loop adaptor is then annealed to the extended strand to produce a partially duplex, two-stranded intermediate, and the partially duplex, two-stranded intermediate is ligated to produce a closed nucleic acid structure, as described above in connection with the general method. The stem-loop adaptor includes a 5' phosphate group, a 5' segment, a 3' segment having a stem-loop structure, and a 3' end hydroxyl, wherein the 5' segment is complementary to the 5' segment of the third primer.

In this variation, the amplification primers do not require 5' phosphate groups, because the 5' phosphate group is included on the third primer. Moreover, given a sufficient amount of target nucleic acid, such an amplification step can be replaced with a restriction endonuclease treatment step, optionally in combination with a fill-in step. The 5' and 3' segments of the third primer can be directly linked to each other (e.g., with no intervening segment) or they can be linked by an intervening segment. An intervening segment can be particularly useful if the nucleic acid having defined ends is produced by amplification using a polymerase, such as Taq polymerase, that tends to add additional, non-template directed nucleobase units at the 3' end of a polymerized strand. Accordingly, a suitable intervening segment can be, e.g., a poly-T sequence (e.g., a sequence of 1, 2, 3, or 4 T nucleobase units). The method can further include the use of a fourth primer, analogous to the third primer but complementary to the opposite strand of the amplified nucleic acid. When third and fourth primers are used to form extended nucleic acids, a pair of stem-loop adaptors can be used, each having a 5' segment complementary to a 5' segment of the third or fourth primer, thus allowing both strands of the target nucleic acid to be incorporated into closed nucleic acid structures in a single set of reactions.

Preferably, for each extended nucleic acid strand, the sequence immediately adjacent to the 5' segment of the third primer (e.g., the 3' segment of the third primer or a portion thereof, or an intervening segment) is complementary to sequence at the 3' end of the strand. Such complementarity improves the yield of closed nucleic acid structures produced by the method. The extent of complementarity can be limited, consisting of, e.g., 1, 2, 3, 4, or more complementary nucleobase unit pairs. Complementarity between the sequences need not be 100% provided that at least the nucleobase unit immediately adjacent to the 5' segment of the third primer can form a nucleobase unit pair with the nucleobase unit at the 3' end of the strand. The sequence of the 3' segment of the third primer, particularly the sequence immediately adjacent to the 5' segment of the third primer, can be selected so as to ensure that such limited complementarity exists. Alternatively, an intervening segment linking the 5' and 3' segments of the third primer can be provided to create such limited complementarity.

Variation 3

Figure 15E:
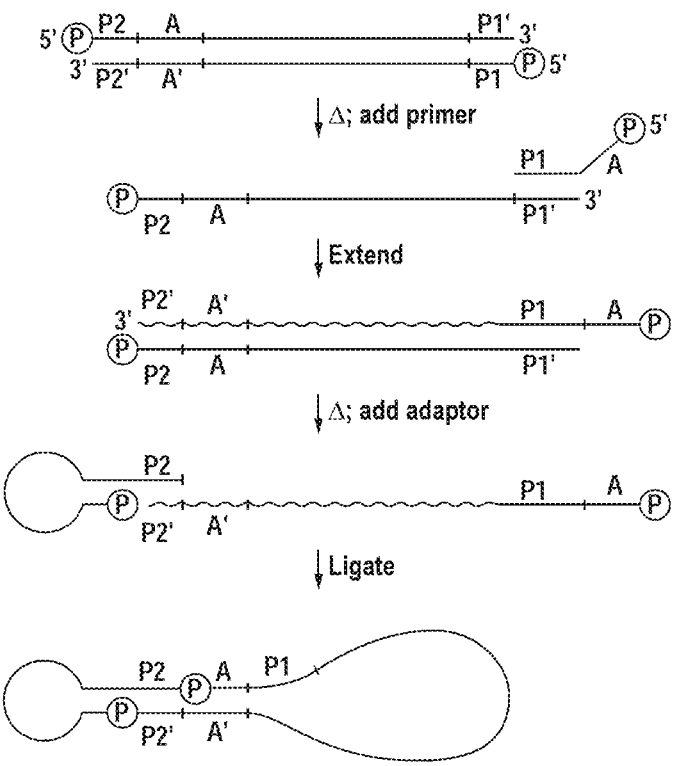
Figure 15F:
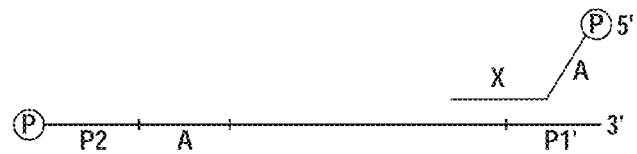

A third variation of method 16 exemplified in FIG. 15E includes an initial step of amplification of a portion of a target nucleic acid using a pair of linear primers that do not include sequence tags (e.g., the primers have 3' and 5' segments complementary to adjacent segments of the target nucleic acid). After the amplification step, but prior to the steps involving the stem-loop adaptor, there is an intervening primer extension step involving a third primer. The third primer includes, from 5' to 3', a 5' phosphate group, a 5' segment, a 3' segment, and a 3' end hydroxyl, wherein the 3' segment is complementary to a 3' segment (e.g., a 3' end segment or a segment internal to the 3' end, as shown in FIG. 15F) of the amplified nucleic acid (i.e., the nucleic acid having defined ends). Thus, for example, the 3' segment of the third primer can have a common sequence with a first primer of the pair of amplification primers, or a portion thereof (e.g., a 5' segment or an internal portion). The 5' segment of the third primer can have a common sequence with a portion of the second primer of the pair of amplification primers (e.g., a 3' segment), a segment of the amplified nucleic acid immediately adjacent and internal to the second primer (e.g., segment "A" in FIG. 15E), or a combination thereof. After annealing the third primer to one strand of the amplified nucleic acid, polymerase extension of the third primer produces a duplex nucleic acid having (1) a strand of the amplified nucleic acid and (2) an extended nucleic acid strand that includes, from 5' to 3', a 5' phosphate group, the third primer, a portion of the target nucleic acid, and a 3' end segment (e.g., the complement of one of the amplification primers). The extended strand is separated from the strand of amplified nucleic acid by denaturation. A stem-loop adaptor is then annealed to the extended strand to produce a partially duplex, two-stranded intermediate, and the partially duplex, two-stranded intermediate is ligated to produce a closed nucleic acid structure, as described above in connection with the general method. The stem-loop adaptor used in this variation of the method includes a 5' phosphate group, a 5' segment having a stem-loop structure, a 3' segment, and a 3' end hydroxyl, wherein the 3' segment has a common sequence with a 5' end segment of the amplified nucleic acid (e.g., a segment corresponding to the second primer of the amplification primer pair, or a 5' segment thereof).

In this variation, the amplification primers do not require 5' phosphate groups, because the 5' phosphate group is included on the third primer. Moreover, given a sufficient amount of target nucleic acid, such an amplification step can be replaced with a restriction endonuclease treatment step, optionally in combination with a fill-in step. The 5' and 3' segments of a stem-loop adaptor can be directly linked to each other (e.g., with no intervening segment) or they can be linked by an intervening segment. An intervening segment can be particularly useful if the nucleic acid having defined ends is produced by amplification using a polymerase, such as Taq polymerase, that tends to add additional, non-template directed nucleobase units at the 3' end of a polymerized strand. Accordingly, a suitable intervening segment can be, e.g., a T nucleobase unit or a poly-T sequence (e.g., a sequence of 2, 3, or 4 T nucleobase units).

This variation of the method can further include the use of a fourth primer, analogous to the third primer but complementary to a 3' end segment of the opposite strand of the amplified nucleic acid. When third and fourth primers are used to form extended nucleic acids, a pair of stem-loop adaptors can be used, each having a 3' segment having a common sequence with a 5' end segment of the amplified nucleic acid (e.g., a segment corresponding to the first or second primer of the amplification primer pair, or a 5' segment thereof), thus allowing both strands of the amplified nucleic acid to be incorporated into closed nucleic acid structures in a single set of reactions.

Variation 4

Figure 15G:
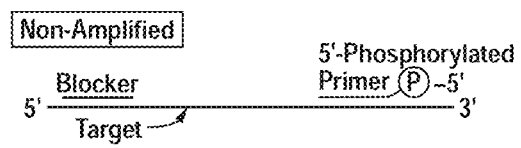
Figure 15G:
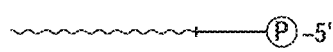
Figure 15G:
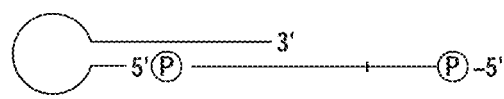
Figure 15G:
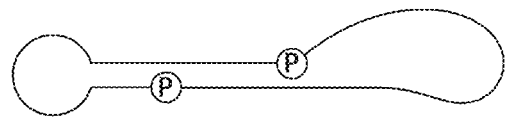

In a fourth variation of Method 16, as depicted in FIG. 15G, the amplification step is replaced by a primer extension step. In this variation, the target nucleic acid is either single-stranded or, if double-stranded, is denatured to release single strands. In the first set of steps, the primer is annealed to a strand of target nucleic acid and polymerase-mediated extension is performed, thereby generating an extended nucleic acid strand duplexed with a target nucleic acid strand. The extended nucleic acid strand includes, from 5' to 3', a 5' phosphate group, the primer, a segment of the target nucleic acid (which include a 3' end segment), and a 3' hydroxyl. The duplex containing the extended nucleic acid strand is then denatured to release the extended nucleic acid strand. In the subsequent set of steps, a 3' segment of a stem-loop adaptor is annealed to the 3' end segment of the extended nucleic acid strand, thereby forming a partially duplex, two-stranded nucleic acid structure. Ligation of the partially duplex, two-stranded nucleic acid structure produces a closed nucleic acid structure.

According to this variation on Method 16, a blocker oligonucleotide can be used, if necessary to define the 3' end of the extended nucleic acid strand. Alternatively, the target nucleic acid can be enzymatically treated, e.g., using a restriction endonuclease, so as to define the 3' end of the extended nucleic acid strand. The primer for the extension step is a linear primer that includes a 5' phosphate group and 3' target-binding segment. Optionally, the primer further includes a 5' segment. The 5' and 3' segments of the primer can be complementary to adjacent segments of the target nucleic acid (e.g., in the manner of standard PCR primers). Preferably, the 5' segment of the primer is complementary to a segment of the target nucleic acid located 5' and distal to the segment of the target nucleic acid to which the 3' segment of the primer is complementary. For example, in the variation of the method depicted in FIG. 15G, the primer can include a 5' segment complementary to a portion of the target nucleic acid immediately adjacent and internal to the 3' end segment that is complementary to the 3' segment of the stem-loop adaptor. Such complementarity can improve the yield of closed nucleic acid structures produced by the method. The extent of complementarity can be limited, consisting of, e.g., 1, 2, 3, 4, or more nucleobase unit pairs. Complementarity between the sequences need not be 100% provided that at least the 5'-most nucleobase unit of the 5' segment of the primer can form a nucleobase unit pair with the nucleobase unit immediately adjacent and internal to the 3' end segment of the extended nucleic acid strand.

Figure 15H:
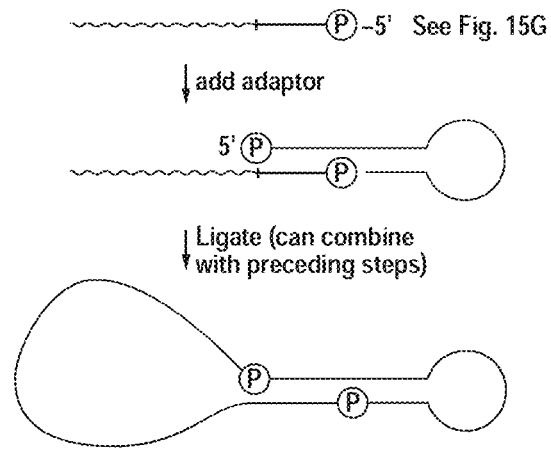

Instead of being complementary to a 3' end segment of the extended nucleic acid strand, the stem-loop adaptor can be designed to be complementary to a 5' end segment of the extended nucleic acid strand, as depicted in FIG. 15H. In such an embodiment, the stem-loop adaptor can have a 5' phosphate group, a 5' segment, a 3' segment that has a stem-loop structure, and a 3' end hydroxyl, wherein the 5' segment is complementary to the primer used in the extension step, or a segment thereof (e.g., a 5' segment thereof). Accordingly, the primer can include a 5' segment that includes a sequence tag and the stem-loop adaptor can include a 5' segment that includes the complement of the sequence tag, or vice versa. When the stem-loop adaptor hybridizes to a 5' end segment of the extended nucleic acid strand, it is advantageous for there to be at least limited complementarity between the 3' end segment of the extended nucleic acid strand and the segment of the extended nucleic acid strand immediately adjacent and internal to the 5' end segment. Such complementarity can improve the yield of closed nucleic acid structures produced by the method. Again, the extent of complementarity can be limited, consisting of, e.g., 1, 2, 3, 4, or more nucleobase unit pairs, and complementarity between the sequences need not be 100% provided that at least the 3'-most nucleobase unit of the 3' segment of the extended nucleic acid strand can form a nucleobase unit pair with the nucleobase unit immediately adjacent and internal to the 5' end segment of the extended nucleic acid strand.

XII. Method 17

Generating a Closed Nucleic Acid Structure Following Primer Extension/Amplification and Intramolecular Ligation Facilitated by a Bridging Oligonucleotide At a general level, method 17 involves two main sets of steps. In the initial set of steps, a nucleic acid having defined ends is provided. In a subsequent set of steps, a bridging oligonucleotide is annealed to the nucleic acid having defined ends, thereby providing a partially duplexed, two-stranded intermediate structure that can be readily converted into a closed nucleic acid structure by ligation.

Figure 16:
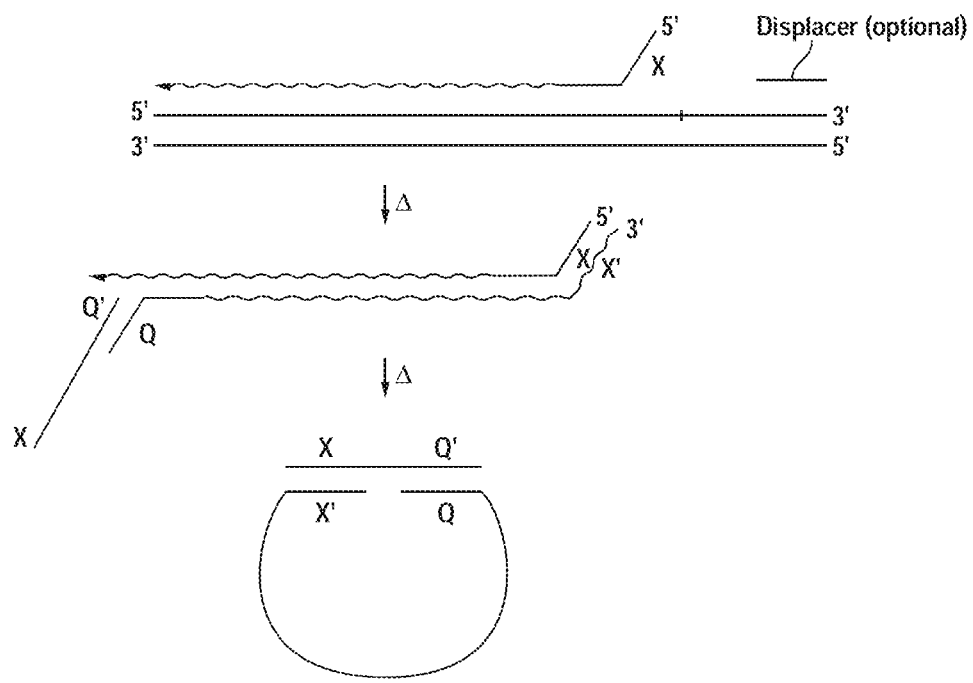
FIG. 16 illustrates an exemplary form of method 17 for generating a closed nucleic acid structure comprising an initial set of steps of primer extension/amplification and a subsequent set of steps in which a bridging oligonucleotide is used to facilitate intramolecular ligation of an extended/amplified nucleic acid strand.

FIG. 16 shows an exemplary embodiment of method 17 in which a nucleic acid having defined ends is obtained (e.g., produced) by two rounds of primer extension. Basically, in the initial steps, a first primer having a 3' target-binding segment is hybridized to a target nucleic acid comprising a region of interest, thereby providing a template for primer extension. Extension from the first primer produces a first extended strand that includes a segment corresponding to the first primer and a segment complementary to the target nucleic acid. The first extended strand is denatured from the template nucleic acid and a second primer having a 5' phosphate group and a 3' segment complementary to a segment of the first extended strand is annealed to the first extended strand, thereby forming a second template for primer extension. Extension from the second primer produces a second extended strand that includes a 5' phosphate group, a segment corresponding to the second primer, a segment having a common sequence with the target nucleic acid, a segment complementary to the first primer, and a 3' hydroxyl group.

In the subsequent steps, the second extended strand is denatured from the first extended strand and a bridging oligonucleotide is annealed to the second extended strand. The bridging oligonucleotide includes a 5' segment complementary to a segment from the 5' end of the second extended strand and a 3' segment complementary to a segment from the 3' end of the second extended strand. Annealing of the 5' segment of the bridging oligonucleotide to the 5' end segment of the second extended strand and the 3' segment of the bridging oligonucleotide to the 3' end segment of the second extended strand produces a partially duplex, two-stranded intermediate. Within the partially duplex, two-stranded intermediate, the 5' phosphate group of the second extended strand is adjacent to, but separated by a nick from, the 3' hydroxyl group of the second extended strand. Ligation of the partially duplex, two-stranded intermediate produces a closed nucleic acid structure.

The target nucleic acid can be double-stranded (as shown in FIG. 16) or single-stranded. The target nucleic acid can be any target nucleic acid described herein, including genomic DNA, cloned fragments, including large nucleic acid clones (e.g., cosmids, BACs, YACs, and so forth), amplified fragments (e.g., amplified by PCR) such as cDNA, RNA and so forth. When the target nucleic acid is double-stranded, a particular strand can be targeted (as shown in FIG. 16) or both strands can be targeted (as discussed below). Double-stranded target nucleic acid can be denatured (e.g., heat denatured) prior to use in the method, thereby providing single-stranded target nucleic acid. Likewise, the duplex comprising the first extended nucleic acid strand and the target nucleic acid strand can be denatured (e.g., heat denatured) prior to use as the template for primer extension from the second primer. Alternatively, a displacer oligonucleotide can be used here to separate the extension product from the template (e.g., as shown in FIG. 16 and discussed below).

The first and second primers can be, e.g., linear primers, as described above. The first primer can include a 3' target-binding segment and, optionally, a 5' phosphate group. The second primer can include a 5' phosphate group and a 3' segment that has a common sequence with a segment of the target nucleic acid strand (e.g., a segment of the target nucleic acid strand located 5' relative to the segment of the target nucleic acid strand to which the first primer hybridizes). One or both of the first and second primers can further include a 5' segment. The 5' segment of the first primer, e.g., can have a common sequence with the 3' segment of the bridging oligonucleotide. The 5' segment of the second primer, e.g., can be complementary to the 5' segment of the bridging oligonucleotide. The 5' segments need not be complementary to the target nucleic acid strand or its complementary strand. For example, either or both 5' segments can include a sequence tag. The sequence tag can be relatively short, e.g., consisting of less than 10 nucleobase units (e.g., consisting of 1, 2, 3, 4, or 5 nucleobase units). Alternatively, the sequence tag can be relatively long, e.g., consisting of at least 10 nucleobase units (e.g., at least 15, 20, 25 or more nucleobase units). The longer sequence tags can be highly selective, hybridizing only poorly or not at all to other nucleic acids (e.g., target nucleic acid) present in the reaction mixtures. Examples of selective sequence tags include, e.g., xTAG®'s, as described above. Optionally, either the first primer or the second primer, or both can be attached to a solid support, such as glass, a polymeric surface, a microchip, a column, or a bead. Having a primer attached to a solid support can facilitate separation of the extended strand from the template nucleic acid strand or each other, which may, in turn, facilitate the formation of the partially double-stranded, two-stranded intermediate and the corresponding closed nucleic acid structure.

The extended strands (e.g., the first or second extended strand) can be separated from template nucleic acid strands to which they are hybridized (e.g., a target nucleic acid strand or a first extended nucleic acid strand) by denaturation (e.g., heat denaturation). Alternatively, the extended strands can be separated, for example, by strand displacement using a primer (i.e., displacer primer) that anneals to a position on the template strand located 3' to the position that the primer that gives rise to the extended strand (e.g., the first or second primer) anneals to. Extension of the displacer primer displaces the extended strand from the template strand. In this manner, primer annealing, subsequent primer extension, and separation of the extended strand as a result of displacement can all happen, for example, at 1 (or 2) temperatures without an intervening denaturation step.

The bridging oligonucleotide can include a 5' segment and a 3' segment. The 5' segment is selected to be complementary to a segment at the 5' end of the second extended strand, while the 3' segment is selected to be complementary to a segment at the 3' end of the second extended strand. The 5' segment can be, e.g., complementary to a 5' segment of the second primer. The 3' segment can, e.g., have a common sequence with a 5' segment of the first primer. The bridging oligonucleotide can further include an additional segment located between the 5' and 3' segments. The intervening segment can be useful, e.g., if the second round of primer extension (e.g., extension from the second primer) involves the use of a polymerase, such as Taq polymerase, that has a tendency to catalyze non-template addition of nucleobase units the 3' end of a nucleic acid strand. Accordingly, the intervening segment can be selected to allow for such non-template addition, as appropriate for the polymerase being used. For example, a suitable intervening segment can include, e.g., a T nucleobase unit or a poly-T sequence (e.g., a sequence of 2, 3, or 4 T nucleobase units).

Although the exemplary method depicted in FIG. 16 features a first round of extension with a first primer and a second round of extension with a second primer, the method can be readily adapted to include extension from two primers in each round of extension. For example, the target nucleic acid can be contacted with both the first primer and the second primer, thereby giving rise to a first template for extension from the first primer and a second template for extension from the second primer. After primer extension, there are two extended nucleic acid strands: one extended nucleic acid strand that includes a segment corresponding to the first primer and a segment complementary to a first strand of the target nucleic acid; and another extended nucleic acid strand that includes a segment corresponding to the second primer and a segment complementary to a second strand of the target nucleic acid (i.e., a segment that has a common sequence with the first strand of the target nucleic acid). In the second round of extension, the extended strands are contacted with third and fourth primers. The third primer hybridizes to the extended strand that includes a segment corresponding to the first primer and the fourth primer hybridizes to the extended strand that includes a segment corresponding to the second primer. Both hybridization events create a template for the second round of primer extension. Following the second round of extension, there are again two extended strands: one extended strand includes a segment corresponding to the third primer, a segment that has a common sequence with the first strand of the target nucleic acid, and a segment complementary to the first primer; and the other extended strand includes a segment corresponding to the fourth primer, a segment complementary to the first strand of the target nucleic acid, and a segment complementary to the second primer.

The third and fourth primers can be, e.g., linear primers, and can have any of the properties of the first and second primers described above. The first and fourth primers can be the same or different (e.g., having different 5' segments). Likewise, the second and third primers can be the same or different (e.g., having different 5' segments). Separate first round extension reactions can be set up for each primer, or the primers can be used in the same reaction. Likewise, separate second round extension reactions can be set up for each primer, or the primers can be used in the same reaction. When separate reactions are set up, the reactions can be performed in parallel (i.e., at the same time) or in series. During the first round of extension, the primers need not have 5' phosphate groups. During the second round of extension, each primer preferably has a 5' phosphate group. Additional rounds of extension can optionally be performed to amplify the target nucleic acid, e.g., if the target nucleic acid is of low abundance. When additional rounds of extension are performed, it is only necessary to include 5' phosphate groups on the primers used in the last round of extension.

When first and second primers are both used in the first extension reaction and third and fourth primers are both used in the second extension reaction, as discussed above, typically two bridging oligonucleotides are needed to make use of both strands of extended nucleic acid produced in the second round of extension. Each of the bridging oligonucleotides has a 5' segment complementary to a segment at the 5' end of one of the extended strands and the 3' segment complementary to a segment at the 3' end of the same extended strand. As an example, one bridging oligonucleotide can include a 5' segment complementary to a 5' segment of the first primer and a 3' segment that has a common sequence with a 5' segment of the third primer. The other bridging oligonucleotide can include, for example, a 5' segment complementary to a 5' segment of the second primer and a 3' segment that has a common sequence with a 5' segment of the fourth primer. If the primers all include 5' segments that have a common sequence, then a single bridging oligonucleotide can be used to produce closed nucleic acid structures for each of the extended strands produced in the second extension step.

Denaturation of duplex nucleic acids (e.g., template, nucleic acids having defined ends, extended nucleic acids including stem-loop primers) and annealing of primers can be achieved using standard techniques, such as varying temperature and/or ionic strength of the buffer. Optionally, one or more denaturation steps can be eliminated, as discussed above.

XIII. Method 18

Generating a Closed Nucleic Acid Structure Following Amplification with a Pair of Stem-Loop Primers that Include Deoxyribo-Uracil At a general level, method 18 involves two main sets of steps. In the initial steps, a double-stranded nucleic acid having defined ends and at least one deoxyribo-uracil nucleobase unit located proximal to the 5' end of each strand is provided. In a subsequent set of steps, the nucleic acid having defined ends is enzymatically modified to remove the deoxyribo-uracil nucleobase units. Intra-molecular hybridization of the modified nucleic acid produces a nicked intermediate that is readily ligated into a closed nucleic acid structure.

Figure 17A:
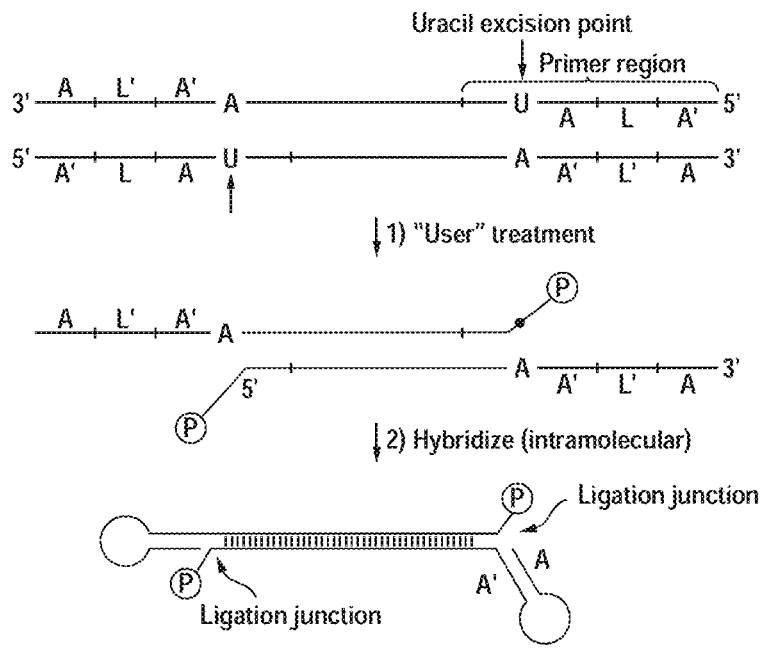
FIGS. 17A, B illustrate an exemplary form of method 18 for generating a closed nucleic acid structure comprising an initial step of amplification with a pair of stem-loop primers that include at least one deoxyribo-uracil nucleobase unit, and a subsequent set of steps wherein the deoxyribo-uracil nucleobase units are excised from the amplified nucleic acid and the resulting excised nucleic acid is allowed to intramolecularly hybridize to form a nicked intermediate that is readily ligated.
Figure 17B:
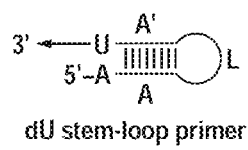

FIGS. 17A, B show an exemplary embodiment of method 18 wherein a nucleic acid having defined ends is obtained (e.g., produced) by amplification using stem-loop primers that include at least one deoxyribo-uracil nucleobase unit. Basically, in the initial step, an amplified nucleic acid comprising a region of interest in a target nucleic acid is generated by mixing the target nucleic acid with a pair of stem-loop primers under amplification/PCR conditions. The stem-loop primers each have a 5' segment, a 3' segment, and an additional segment between the 5' and 3' segments. The 5' segments have a stem-loop structure, the 3' segments are target-binding segments, and the additional intermediary segment includes at least one deoxyribo-uracil nucleobase unit. The resulting amplified nucleic acid (i.e., nucleic acid having defined ends) is double-stranded and includes a segment of the target nucleic acid (i.e., region of interest) flanked by the stem-loop primers and their complementary segments.

In the subsequent steps, the deoxyribo-uracil nucleobase units are enzymatically excised from the amplified nucleic acid. The excision removes the deoxyribo-uracil nucleobase unit(s) and all nucleobase units located 5' to the deoxyribo-uracil nucleobase units (i.e., the 5' segments and all or part of the additional intermediary segments of the stem-loop primers) in each strand of the amplified nucleic acid, leaving a 5' phosphate group at the 5' end of each strand. As a result, the excised nucleic acid is a duplex nucleic acid having, at each end, a 5' phosphate group and a 3' overhang ending with a 3' hydroxyl group. The 3' overhangs are complementary to the 5' segments and all or part of the intermediary segments of the stem-loop primers. Due to this complementarity, the 3' overhangs are capable of forming stem-loop structures. Accordingly, the 3' overhangs of the excised nucleic acid are allowed to intramolecularly hybridize and form stem-loop structures. After formation of the stem-loop structures, the excised nucleic acid has a nicked, circularized structure wherein the 5' phosphate groups at the end of each strand are adjacent to, but separated by a nick from, the 3' hydroxyl groups at the ends of the 3' overhangs. Ligation of the nicks produces a closed nucleic acid structure.

The target nucleic acid can be double-stranded or single-stranded. The target nucleic acid can be any target nucleic acid described herein, including genomic DNA, cloned fragments, including large nucleic acid clones (e.g., cosmids, BACs, YACs and so forth), amplified fragments (e.g., amplified by PCR), such as, cDNA, RNA, and so forth. Amplification of the target nucleic acid in the initial step of the method can include two or more rounds of amplification. Two rounds of amplification are sufficient to attach the 5' and intermediate segments from the amplification primers to the ends of the amplified nucleic acid if the target nucleic acid is double-stranded. Three rounds of amplification are sufficient if the target nucleic acid is single-stranded. Additional rounds of amplification can be used, e.g., as needed, depending on the abundance of the target nucleic acid.

The stem-loop primers used in the initial amplification step of the method can be, e.g., any stem-loop primer described herein. Typically, the stem-loop primers includes a 5' segment having a stem-loop structure, an intermediary segment, and a 3' target binding segment. The intermediary segment can, e.g., include 1, 2, 3, 4, or more nucleobase units, at least one of which is a deoxyribo-uracil nucleobase unit. Preferably, the intermediary segment comprises or consists of one or two deoxyribo-uracil nucleobase units. The 5' segment can include 5'-most and 3'-most sub-segments, wherein the 3'-most sub-segment forms a stem-loop structure and the 5'-most sub-segment is complementary to all or part of the intermediary segment. The inclusion of such a 5'-most sub-segment in the stem-loop primers can facilitate proper spacing of the 5' phosphate and 3' hydroxyl groups when the 3' overhangs intramolecularly hybridize to form stem-loop structures. One or both of the stem-loop primers can include a 5' phosphate group.

Exemplary methods for excising deoxyribo-uracil nucleobase units from a double-stranded DNA template include, e.g., treating the template with a combination of uracil DNA glycosidase (UNG) enzyme and either T4 endonuclease or DNA glycosylase-lyase endo VIII. A mixture of UNG enzyme and DNA glycosylase-lyase endo VIII is commercially available as the "USER™ enzyme" from New England Biolabs. Excision of deoxyribo-uracil by such methods not only removes the deoxyribo-uracil but also removes any nucleobase units located 5' to the deoxyribo-uracil nucleobase unit(s) on the same strand of nucleic acid. As a result, single-stranded 3' overhangs are created. In addition, the methods leave a 5' phosphate group at the 5' end of the strand from which the deoxyribo-uracil is excised.

Denaturation of duplex nucleic acids (e.g., template, nucleic acids having defined ends, extended nucleic acids including stem-loop primers, and so forth) and annealing of primers can be achieved using standard techniques, such as varying temperature and/or ionic strength of the buffer.

XIV. Method 19

At a general level, method 19 involves two main sets of steps. In the initial steps, a double-stranded nucleic acid having defined ends and at least one deoxyribo-uracil nucleobase unit located proximal to the 5' end of each strand is provided. In a subsequent set of steps, the nucleic acid having defined ends is enzymatically modified to remove the deoxyribo-uracil nucleobase units and stem-loop adaptors are annealed to the modified nucleic acid, thereby forming a nicked intermediate that is readily ligated into a closed nucleic acid structure.

Figure 18:
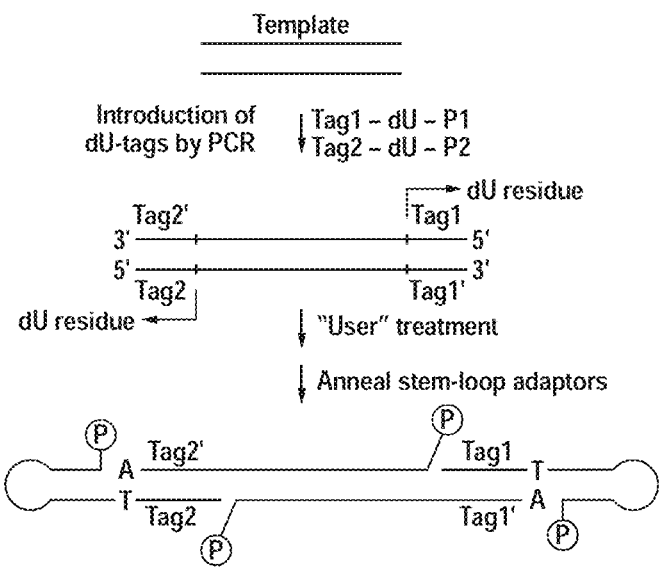
FIG. 18 illustrates an exemplary form of method 19 for generating a closed nucleic acid structure comprising an initial step of amplification with a pair of linear primers that include at least one deoxyribo-uracil nucleobase unit, and a subsequent set of steps wherein the deoxyribo-uracil nucleobase units are excised from the amplified nucleic acid and a pair of adaptors having a stem-loop structure are annealed to the excised nucleic acid, thereby forming a nicked intermediate that is readily ligated.

FIG. 18 shows an exemplary embodiment of method 19 wherein a nucleic acid having defined ends is obtained (e.g., produced) by amplification using linear primers that include at least one deoxyribo-uracil nucleobase unit. Basically, in the initial step, an amplified nucleic acid comprising a region of interest in a target nucleic acid is generated by mixing the target nucleic acid with a pair of linear amplification primers under amplification/PCR conditions. The amplification primers each have a 5' segment, a 3' segment, and an additional segment between the 5' and 3' segments. The 3' segments are target-binding segments, the 5' segments include a sequence tag, and the additional intermediary segment includes at least one deoxyribo-uracil nucleobase unit. The resulting amplified nucleic acid (i.e., nucleic acid having defined ends) is double-stranded and includes a segment of the target nucleic acid (i.e., region of interest) flanked by the amplification primers and their complementary segments.

In the subsequent set of steps, the deoxyribo-uracil nucleobase units are enzymatically excised from the amplified nucleic acid. The excision removes the deoxyribo-uracil nucleobase unit(s), as well as all nucleobase units located 5' to the deoxyribo-uracil nucleobase units (i.e., the 5' segments and all or a portion of the additional intermediary segment of the amplification primers) on each strand of the amplified nucleic acid, leaving a 5' phosphate group at the 5' end of each strand. As a result, the excised nucleic acid is a duplex nucleic acid having, at each end, a 5' phosphate group and a 3' overhang ending with a 3' hydroxyl group. The 3' overhangs are complementary to the 5' segments and all or part of the additional intermediary segments of the amplification primers. Stem-loop adaptors are then annealed to the excised (i.e., modified) nucleic acid. Each stem-loop adaptor includes a 5' phosphate group, a 5' segment having a stem-loop structure, a 3' segment complementary to a 3' overhang of the excised nucleic acid, and a 3' hydroxyl group. After hybridization of the stem-loop adaptors to the excised nucleic acid, the resulting intermediate has a nicked, circularized structure wherein the 5' phosphate groups at the end of each strand of the excised nucleic acid are adjacent to, but separated by a nick from, the 3' hydroxyl groups of the stem-loop adaptors. In addition, the 5' phosphate groups of the stem-loop adaptors are adjacent to, but separated by a nick from, the 3' hydroxyl groups at the ends of the 3' overhangs of the excised nucleic acid. Ligation of the nicks produces a closed nucleic acid structure.

The target nucleic acid can be double-stranded (e.g., as shown in FIG. 18) or single-stranded. The target nucleic acid can be any target nucleic acid described herein, including genomic DNA, cloned fragments, including large nucleic acid clones (e.g., cosmids, BACs, YACs and so forth), amplified fragments (e.g., amplified by PCR), such as cDNA or RNA among others. Amplification of the target nucleic acid in the initial step of the method can include two or more rounds of amplification. Two rounds of amplification are sufficient to attach the 5' and intermediate segments from the amplification primers to the ends of the amplified nucleic acid if the target nucleic acid is double-stranded. Three rounds of amplification are sufficient if the target nucleic acid is single-stranded. Additional rounds of amplification can be used, e.g., as needed, depending on the abundance of the target nucleic acid.

The linear primers used in the initial amplification step of the method can be, e.g., any linear primer described herein. Typically, the linear primers include a 5' segment, an intermediary segment, and a 3' target binding segment. The intermediary segment is located between the 5' and 3' segments and can, e.g., include 1, 2, 3, 4, or more nucleobase units, at least one of which is a deoxyribo-uracil nucleobase unit. Preferably, the intermediary segment comprises or consists of one or two deoxyribo-uracil nucleobase units. The 5' segment can include a sequence tag. The sequence tag can be relatively short, e.g., consisting of less than 10 nucleobase units (e.g., consisting of 1, 2, 3, 4, or 5 nucleobase units). Short sequence tags preferably have a high GC content. Alternatively, the sequence tag can be relatively long, e.g., consisting of at least 10 nucleobase units (e.g., at least 15, 20, 25 or more nucleobase units). The longer sequence tags can be highly selective, hybridizing only poorly or not at all to other nucleic acids (e.g., the target nucleic acid) present in the amplification reaction. Examples of selective sequence tags include, e.g., xTAG®'s, as described above. Alternatively, the primers used to amplify the target nucleic acid can include a 3' segment and a 5' segment, wherein one or both of the 5' segments includes a sequence complementary to a portion of the target nucleic acid. For example, the 5' and 3' segments of an amplification primer can be complementary to adjacent portions of the target nucleic acid (e.g., as is typical for conventional PCR primers). One or both of the stem-loop primers can include a 5' phosphate group.

The stem-loop adaptor(s) used in the method can be, e.g., any stem-loop adaptor described herein. Typically, each stem-loop adaptor includes a 5' phosphate group, a 5' segment having a stem-loop structure, a 3' segment, and a 3' end hydroxyl. The 3' segment can be complementary to a 3' overhang of one strand of the excised (i.e., modified) nucleic acid. For example, the 3' segment can be complementary to the 5' segment and all or part of an intermediary segment of an amplification primer. The 5' and 3' segments of the stem-loop adaptor(s) can be directly linked to each other (e.g., with no intervening segment) or they can be linked by an intervening segment. An intervening segment can be particularly useful is the amplified nucleic acid is produced by amplification using a polymerase, such as Taq polymerase, that tends to add additional, non-template directed nucleobase units at the 3' end of a polymerized strand. Accordingly, a suitable intervening segment can be, e.g., a T nucleobase unit or a poly-T sequence (e.g., a sequence of 2, 3, or 4 T nucleobase units).

Excision of deoxyribo-uracil nucleobase units from the amplified nucleic acid can, e.g., be performed as discussed in connection with Method 18. Denaturation of duplex nucleic acids (e.g., template, nucleic acids having defined ends, extended nucleic acids including stem-loop primers) and annealing of primers can be achieved using standard techniques, such as varying temperature and/or ionic strength of the buffer.

XV. Method 20

At a general level, method 20 involves two main steps, or sets of steps. In the initial set of steps, the strands of a double-stranded nucleic acid having defined ends are extended. In a subsequent set of steps, the extended nucleic acid strands are allowed to intramolecularly and intermolecularly hybridize to form a nicked intermediate that is readily ligated into a closed nucleic acid structure.

Figure 19:
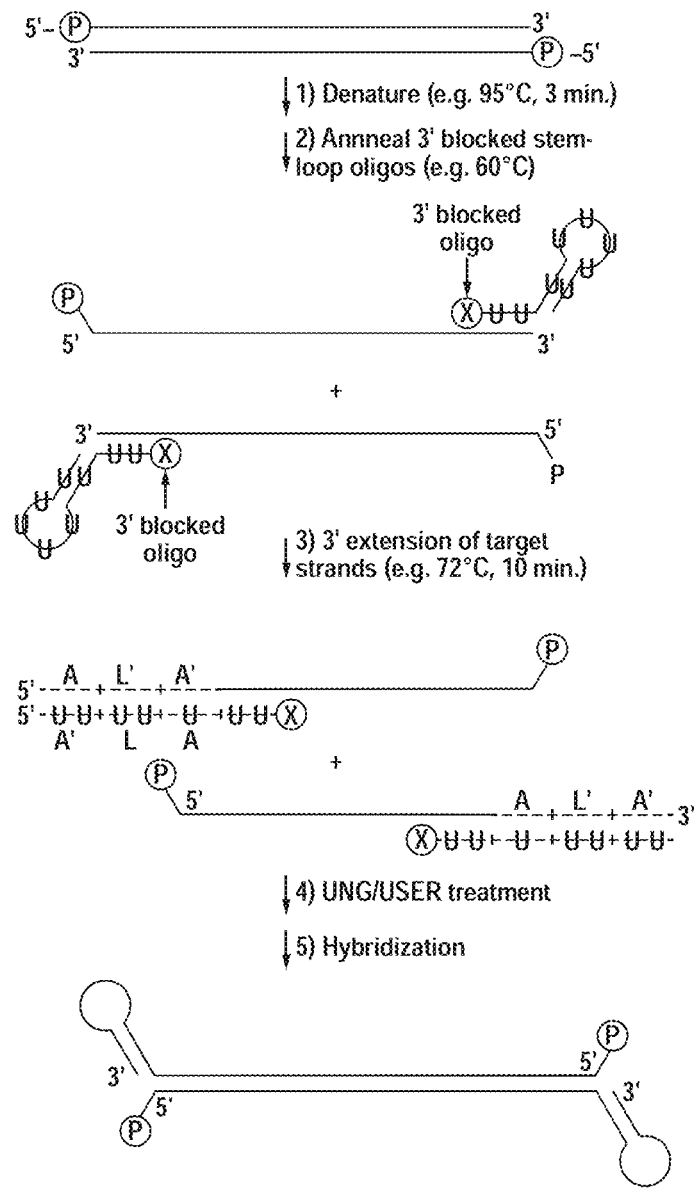
FIG. 19 illustrates an exemplary form of method 20 for generating a closed nucleic acid structure comprising an initial step of template extension with a pair of 3' blocked stem-loop oligonucleotides to add stem-loop structures to the 3' ends of a nucleic acid having defined ends, and a subsequent set of steps in which the 3' blocked stem-loop oligonucleotides are removed and the extended template strands are allowed to intramolecularly and intermolecularly hybridize to form a nicked intermediate that is readily ligated.

FIG. 19 shows an exemplary embodiment of method 20 wherein the strands of a double-stranded nucleic acid having defined ends (e.g., a target nucleic acid) are extended using 3' blocked stem-loop oligonucleotides. Basically, in the initial set of steps, a double-stranded nucleic acid having defined ends is denatured to yield two strands of denatured nucleic acid. Each strand of denatured nucleic acid includes a 5' phosphate group and a region of interest from a target nucleic acid, and a 3' end segment. A pair of 3' blocked stem-loop oligonucleotides is annealed to the strands of denatured nucleic acid. Each 3' blocked stem-loop oligonucleotide includes a 5' segment having a stem-loop structure, a 3' segment complementary to a 3' end segment of a strand of denatured nucleic acid, and a plurality of deoxyribo-uracil nucleobase units. Annealing of the 3' segment of each 3' blocked stem-loop oligonucleotide to a 3' end segment of a strand of denatured nucleic acid provides a template for extension of the denatured nucleic acid strand. Polymerase-mediated extension (e.g., using standard extension conditions, such as used in PCR) of the denatured nucleic acid strands produces 3' extended nucleic acid strands, wherein each extended strand includes the 5' phosphate group and target nucleic acid region of interest from a denatured nucleic acid strand and, in addition, a 3' extension that ends with a 3' hydroxyl group and is complementary to a portion of the 3' blocked stem-loop oligonucleotide (e.g., a 5' segment).

In the subsequent set of steps, the 3' blocked stem-loop oligonucleotides are removed (e.g., degraded) by enzymatic excision of the deoxyribo-uracil nucleobase units. The 3' extended nucleic acid strands are then allowed to intramolecularly and intermolecularly hybridize to form a nicked intermediate. The nicked intermediate includes a double-stranded segment formed from the intermolecular hybridization of the target nucleic acid segments of the 3' extended nucleic acid strands and two stem-loop structures formed from intramolecular hybridization of the 3' extensions. The stem-loop structures bring the 3' hydroxyl groups of each strand adjacent to a 5' phosphate group of the other strand, such that each 5' phosphate group is separated from a 3' hydroxyl group by a nick. The nicked intermediate is then contacted with a ligase that seals the nicks, thereby producing a closed nucleic acid structure. The closed nucleic acid structure includes a double-stranded segment of target nucleic acid wherein the two strands are joined to one another by stem-loop structures.

The double-stranded nucleic acid having defined ends can be a double-stranded target nucleic acid or can be obtained from a target nucleic acid, e.g., as described above in connection with Method 16. Target nucleic acid used to generate nucleic acid having defined ends can be double-stranded or single-stranded. The target nucleic acid can be any type of target nucleic acid described herein, including genomic DNA, cloned fragments, including large nucleic acid clones (e.g., cosmids, BACs, YACs and so forth), amplified fragments (e.g., amplified by PCR) such as cDNA or RNA among others. The nucleic acid having defined ends can be obtained (e.g., produced) from the target nucleic acid by amplification, e.g., using a linear primer pair, as discussed above. Thus, the linear primers can be standard PCR primers or they can include a sequence tag. Linear primers can include a 3' target-binding segment and a 5' segment (e.g., a target-binding segment or a sequence tag). Typically, one or both of the linear primers include a 5' phosphate.

A nucleic acid having defined ends can be obtained from target nucleic acid by means other than just amplification. For example, a primer and a blocker oligonucleotide can be used to generate a single-stranded nucleic acid having defined ends, e.g., as described in variation 4 of Method 16, and the single-stranded nucleic acid can be converted into a double-stranded nucleic acid, e.g., by amplification or extension of a primer that binds to the 3' end of the single-stranded nucleic acid. Alternatively, nucleic acid having defined ends can be generated by digesting double-stranded target nucleic acids with restriction endonucleases and, optionally, filling-in or removing any 3' or 5' overhangs generated by the restriction endonucleases.

The 3' blocked stem-loop oligonucleotides can be, e.g., any stem-loop oligonucleotide described herein, provided that (1) binding of the oligonucleotides to the strands of the nucleic acid having defined ends provides a template for extension of the nucleic acid strands, and (2) the 3'-most nucleobase unit of the oligonucleotide blocks polymerase-mediated extension of the oligonucleotide. 3'-most nucleobase units suitable for blocking polymerase-mediated extension are described, e.g., in the general description of target extension oligonucleotides provided above. Typically, the 3' blocked stem-loop oligonucleotides include a 5' segment having a sequence capable of forming a stem-loop structure and a 3' segment complementary to a 3' end segment of a strand of nucleic acid having defined ends. If the nucleic acid having defined ends is an amplification product, the 3' segment of the 3' blocked stem-loop oligonucleotide can be complementary to all or part (e.g., a 5' segment) of a linear primer used in the amplification reaction.

Preferably, the 3' blocked stem-loop oligonucleotides are removed from the reaction mixture following formation of the extended nucleic acid strands. Accordingly, the 3' blocked stem-loop oligonucleotide can include one or more (e.g., a plurality of) deoxyribo-uracil nucleobase units. Treatment of such oligonucleotides (either in monomeric form or when hybridized to extended nucleic acid strands) with enzymes that mediate uracil excision results in degradation of the oligonucleotides, thereby removing them from the reaction mixture. The deoxyribo-uracil nucleobase units can be in the 3' and/or 5' segments of the 3' blocked stem-loop oligonucleotides. For example, the deoxyribo-uracil nucleobase units can be located along the entire length of the oligonucleotide (e.g., one every 4 to 15, or every 5 to 12 nucleobase units) so as to ensure degradation of the oligonucleotide to an extent sufficient to prevent any remaining oligonucleotide fragments from interfering with subsequent steps in the method. Excision of deoxyribo-uracil nucleobase units from the oligonucleotides can, e.g., be performed as discussed in connection with Method 18 (e.g., using a combination of uracil DNA glycosidase (UNG) enzyme and either T4 endonuclease or DNA glycosylase-lyase endo VIII).

As an alternative to the inclusion of deoxyribo-uracil, the 3' blocked stem-loop oligonucleotides can be linked to a solid support. For example, the 3' blocked stem-loop oligonucleotides can be directly linked to a solid support or they can include one or more nucleobase units that comprise an affinity label, such as biotin, avidin, a his-tag, or the like, capable of providing an indirect linkage to a solid support. Following the formation of extended nucleic acid strands, the 3' blocked stem-loop oligonucleotides can be separated from the reaction mixture by means of the solid support linkage. For example, 3' blocked stem-loop oligonucleotides labeled with biotin can be separated from a reaction mixture by passing the mixture over a streptavidin affinity column. Alternatively, the reaction mixture can be incubated with streptavidin-conjugated beads. The eluate from the column or the supernatant obtained after removal of the beads are depleted of biotin-labeled 3' blocked stem-loop oligonucleotides. Optionally, 3' blocked stem-loop oligonucleotides can be dissociated from the extended nucleic acid strands (e.g., by denaturation) prior to being separated from the reaction mixture.

Other methods of removing 3' blocked stem-loop oligonucleotides from the reaction mixture can be used. For example, monomeric 3' blocked stem-loop oligonucleotides that do not contain deoxyribo-uracil or an affinity label and are not otherwise linked to a solid support can be removed from the reaction mixture by passing the reaction mixture through a size exclusion column. The molecular weight cut-off of the column can be selected such that monomeric 3' blocked stem-loop oligonucleotides are retained by the column while extended nucleic acid strands are not. Optionally, 3' blocked stem-loop oligonucleotides hybridized to extended nucleic acid strands can be dissociated from the extended nucleic acid strands (e.g., by denaturation) prior to passing the reaction mixture through a size exclusion column.

Denaturation of duplex nucleic acids (e.g., template nucleic acid, nucleic acids having defined ends, extended nucleic acids including stem-loop primers) and annealing of primers can be achieved using standard techniques, such as varying temperature and/or ionic strength of the buffer.

Variation 1

In a variation of Method 20, the initial set of steps in the method involve extension of denatured nucleic acid using a single 3' blocked stem-loop oligonucleotide. The 3' blocked stem-loop oligonucleotide can, e.g., anneal to one or both strands of the denatured nucleic acid. For example, the 3' segment of the 3' blocked stem-loop oligonucleotide can be complementary to the 3' end segments of both strands of the nucleic acid having defined ends, and therefore anneal to the 3' end segments of both strands of denatured nucleic acid. In such a situation, the method can proceed exactly as discussed above. Annealing of a single 3' blocked stem-loop oligonucleotide to both strands of the denatured nucleic acid can be achieved so long as the 3' end segments of the strands of the nucleic acid having defined ends share a common sequence. For example, if the nucleic acid having defined ends is prepared by amplification using linear primers, linear primers that include 5' segments that share a common sequence (e.g., a common sequence tag) produce a nucleic acid having defined ends wherein the 3' end segments of the strands of the nucleic acid likewise share a common sequence (i.e., the complement to the 5' segments of the linear primers).

Alternatively, the 3' blocked stem-loop oligonucleotide can be complementary to the 3' end segment of only one strand of the nucleic acid having defined ends, and therefore anneal to the 3' segment of only one strand of denatured nucleic acid. In such a situation, only a single strand of the denatured nucleic acid (and, thus, only a single strand of the nucleic acid having defined ends) is extended and thereafter incorporated into a closed nucleic acid structure. In this variation, the method is similar to that of Method 15 when only a single stem-loop primer is used (the key difference being that the present variation involves addition of a stem-loop structure by target strand extension rather that by stem-loop primer extension). With regards to the nucleic acid having defined ends used in this variation of the method, only the strand that is to be incorporated into a closed nucleic acid structure needs to have a 5' phosphate group. Accordingly, if the nucleic acid having defined ends is prepared by amplification, only one of the amplification primers (i.e., the amplification primer that becomes part of the strand to be incorporated into a closed nucleic acid structure) needs to include a 5' phosphate group. However, if both amplification primers include a 5' phosphate group, then each strand of the nucleic acid having defined ends can be incorporated into a closed nucleic acid structure, e.g., in separate reactions using different 3' blocked stem-loop oligonucleotides.

The 3' blocked stem-loop oligonucleotide used in this variation of Method 20 can be any of the 3' blocked stem-loop oligonucleotides described above. If the 3' blocked stem-loop oligonucleotide anneals to only one strand of denatured nucleic acid, it preferably includes a 5' segment having a sequence capable of forming a stem-loop structure, a 3' target-binding segment (e.g., complementary to a 3' end segment of a strand of nucleic acid having defined ends), and an additional intervening segment (e.g., a sequence of 1, 2, 3, 4, or more nucleobase units) that links the 3' and 5' segments. The intervening segment can, e.g., have a common sequence with a 5' end segment of the strand of denatured nucleic acid that gets extended. Such an intervening segment can, e.g., facilitate the formation of a closed nucleic acid structure (e.g., by providing a segment in the 3' extension of the extended nucleic acid strand that is complementary to the 5' end segment of the same strand). If the 3' blocked stem-loop oligonucleotide does not include an intervening segment, preferably the 3' end segment of the strand of nucleic acid having defined ends, or a 3'-most subsegment thereof (e.g., consisting of 1, 2, 3, 4 or more nucleobase units) is complementary to a 5' end segment of the same strand. The complementarity need not be perfect providing that at least the 3'-most nucleobase unit of the 3' end segment is complementary to the 5'-most nucleobase unit of the 5' end segment. Similar to the intervening segment, this complementarity can facilitate formation of a closed nucleic acid structure. Nucleic acids having 1, 2, 3, 4, or more complementary nucleobase units at their 5' and 3' ends can be prepared in a variety of ways, including selection of the 5' and 3' ends of a target nucleic acid, amplification of target nucleic acid using primers that have 5' segments that have a common sequence, restriction endonuclease digestion of double-stranded target nucleic acid, optionally followed by fill-in of 3' overhangs or removal of 5' overhangs.

When using a single 3' blocked stem-loop oligonucleotide for the incorporation of a single strand of denatured nucleic acid into a closed nucleic acid structure, the method can further include the use of blocker oligonucleotides to block intermolecular hybridization of the extended nucleic acid strand and the complementary strand of denatured nucleic acid. The blocker oligonucleotides can hybridize to the complementary strand of denatured nucleic acid, e.g., in the manner depicted in FIG. 15B.

XVI. Method 21

At a general level, method 21 involves two main steps, or sets of steps. In the initial set of steps, the strands of a double-stranded nucleic acid having defined ends are extended. In a subsequent set of steps, the extended nucleic acid strands are allowed to intermolecularly hybridize and stem-loop adaptors are annealed to the 3' extensions of the extended strands, thereby forming a nicked intermediate that is readily ligated into a closed nucleic acid structure.

Figure 20A:
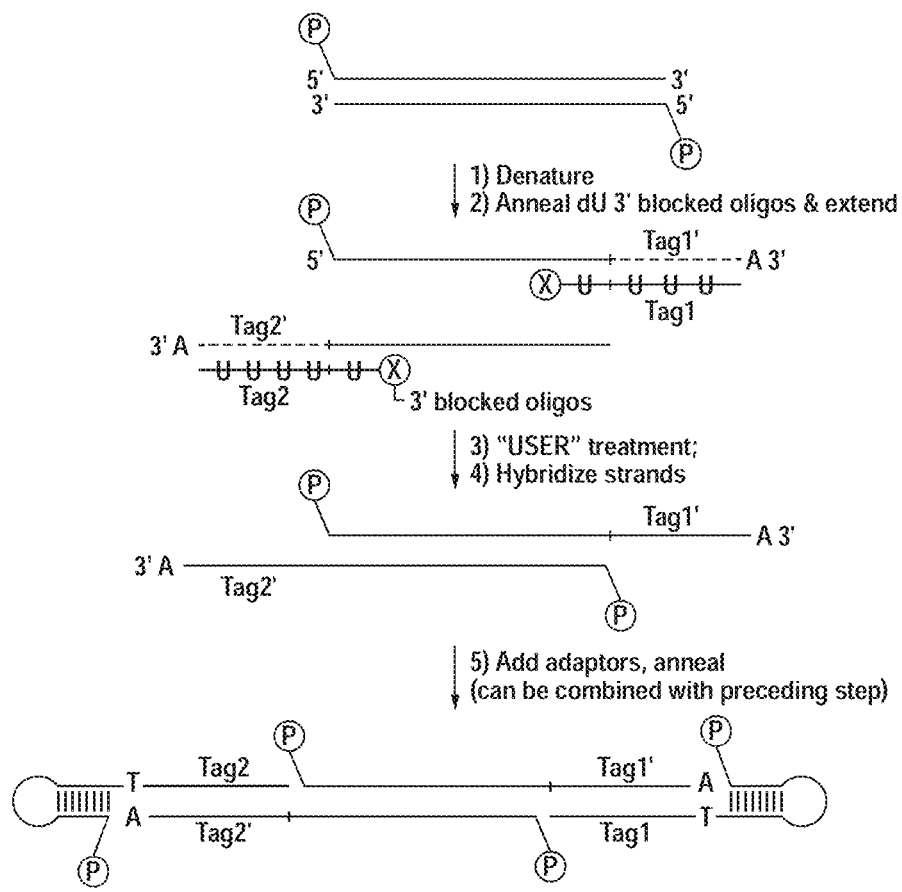
FIGS. 20A, B, and C illustrate exemplary forms of method 21 for generating a closed nucleic acid structure comprising an initial step of template extension with a pair of 3' blocked oligonucleotides to add tags to the 3' ends of the strands of a nucleic acid having defined ends, and a subsequent set of steps in which the 3' blocked oligonucleotides are removed and one or more stem-loop adaptors are annealed to the 3' ends of the strands of extended nucleic acid, thereby forming a nicked intermediate that is readily ligated.

FIG. 20A shows an exemplary embodiments of method 21 wherein the strands of a double-stranded nucleic acid having defined ends (e.g., a target nucleic acid) are extended using 3' blocked oligonucleotides. Basically, in the initial set of steps, a double-stranded nucleic acid having defined ends is denatured to yield two strands of denatured nucleic acid. Each strand of denatured nucleic acid includes a 5' phosphate group, a region of interest from a target nucleic acid, and a 3' end segment. A pair of 3' blocked oligonucleotides is annealed to the strands of denatured nucleic acid. Each 3' blocked oligonucleotide includes a 5' segment, a 3' segment complementary to a 3' end segment of a strand of denatured nucleic acid, and a plurality of deoxyribo-uracil nucleobase units. The 5' segments provide sequence tags. Annealing of the 3' segment of each 3' blocked oligonucleotide to a 3' end segment of a strand of denatured nucleic acid provides a template for extension of the denatured nucleic acid strand. Polymerase-mediated extension (e.g., using standard extension conditions, such as used in PCR) of the denatured nucleic acid strands produces 3' extended nucleic acid strands, wherein each strand includes the 5' phosphate group and target nucleic acid region of interest (or complement thereof) from a denatured nucleic acid strand and, in addition, a 3' extension that ends with a 3' hydroxyl group and is complementary to the 5' segment (e.g., sequence tag) of a 3' blocked oligonucleotide. As depicted in FIG. 20A, each 3' extension includes a 3'-most A nucleobase unit added in a template-independent manner by the polymerase used in the extension step.

In the subsequent set of steps, the 3' blocked oligonucleotides are removed (e.g., degraded) by enzymatic excision of the deoxyribo-uracil nucleobase units. The 3' extended nucleic acid strands are then allowed to intermolecularly hybridize to form a duplex nucleic acid intermediate. Each end of the duplex nucleic acid intermediate includes a 5' phosphate group and a single-stranded 3' extension ending in a 3' hydroxyl group. The single-stranded 3' extensions are the 3' extensions from the 3' extended nucleic acid strands and, thus, are complementary to the 5' segments of the 3' blocked oligonucleotides and include an additional 3'-most A nucleobase unit. The duplex nucleic acid intermediate is then contacted with a pair of stem-loop adaptors. Each adaptor includes a 5' phosphate group, a 5' segment having a stem-loop structure, an intervening T nucleobase unit, a 3' segment that has a common sequence with a 5' segment of one of the 3' blocked stem-loop oligonucleotides, and a 3' hydroxyl group. Annealing of the stem-loop adaptors to the 3' extensions of the duplex nucleic acid intermediate produces a nicked intermediate in which the 5' phosphate groups of the stem-loop adaptors are adjacent to, but separated by a nick from, the 3' hydroxyl groups at the ends of the duplex nucleic acid intermediate, and the 5' phosphate groups at the ends of the duplex nucleic acid intermediate are adjacent to, but separated by a nick from, the 3' hydroxyl groups of the stem-loop adaptors. The nicked intermediate is contacted with a ligase that seals the nicks, thereby producing a closed nucleic acid structure. The closed nucleic acid structure includes a double-stranded segment of target nucleic acid wherein the two strands are joined to one another by stem-loop structures.

The double-stranded nucleic acid having defined ends can be a double-stranded target nucleic acid or can be obtained from a target nucleic acid, e.g., as described above in connection with Method 16. Target nucleic acid used to generate nucleic acid having defined ends can be double-stranded or single-stranded. The target nucleic acid can be any type of target nucleic acid described herein, including genomic DNA, cloned fragments, including large nucleic acid clones (e.g., cosmids, BACs, YACs and so forth), amplified fragments (e.g., amplified by PCR) such as cDNA, RNA, and so forth. The nucleic acid having defined ends can be obtained (e.g., produced) from the target nucleic acid by amplification, e.g., using a linear primer pair, as discussed above. Thus, the linear primers can be standard PCR primers or they can include a sequence tag. Linear primers can include a 3' target-binding segment and a 5' segment (e.g., a target-binding segment or a sequence tag). Typically, one or both of the linear primers include a 5' phosphate.

A nucleic acid having defined ends can be obtained from target nucleic acid by means other than just amplification. For example, a primer and a blocker oligonucleotide can be used to generate a single-stranded nucleic acid having defined ends, e.g., as described in variation 4 of Method 16, and the single-stranded nucleic acid can be converted into a double-stranded nucleic acid, e.g., by amplification or extension of a primer that binds to the 3' end of the single-stranded nucleic acid. Alternatively, nucleic acid having defined ends can be generated by digesting double-stranded target nucleic acids with restriction endonucleases and, optionally, filling-in or removing any 3' or 5' overhangs generated by the restriction endonucleases.

The 3' blocked oligonucleotides can be, e.g., any linear oligonucleotide described herein, provided that (1) binding of the oligonucleotides to the strands of the nucleic acid having defined ends provides a template for extension of the nucleic acid strands, and (2) the 3'-most nucleobase unit of the oligonucleotide blocks polymerase-mediated extension of the oligonucleotide. 3'-most nucleobase units suitable for blocking polymerase-mediated extension are described, e.g., in the general description of target extension oligonucleotides provided above. Typically, the 3' blocked oligonucleotides include a 5' segment, a 3' segment complementary to a 3' end segment of a strand of nucleic acid having defined ends, and optionally an additional intervening segment that links the 3' and 5' segments. If the nucleic acid having defined ends is an amplification product, the 3' segment of the 3' blocked oligonucleotide can be complementary to all or part (e.g., a 5' segment) of a linear primer used in the amplification reaction. An intervening segment of a 3' blocked oligonucleotide can, e.g., include 1, 2, 3, 4, or more nucleobase units. An intervening segment can, e.g., have a common sequence with the 5' end of a denatured nucleic acid strand (e.g., a 5' segment, or a 5'-most sub-segment thereof, of the denatured nucleic acid strand to which the oligonucleotide hybridizes). The 5' segments of the 3' blocked oligonucleotides can, e.g., have different sequences (e.g., different sequence tags). Alternatively, the 5' segments can have a common sequence, in which case only a single stem-loop adaptor is required in the subsequent steps of the method.

Figure 20B:
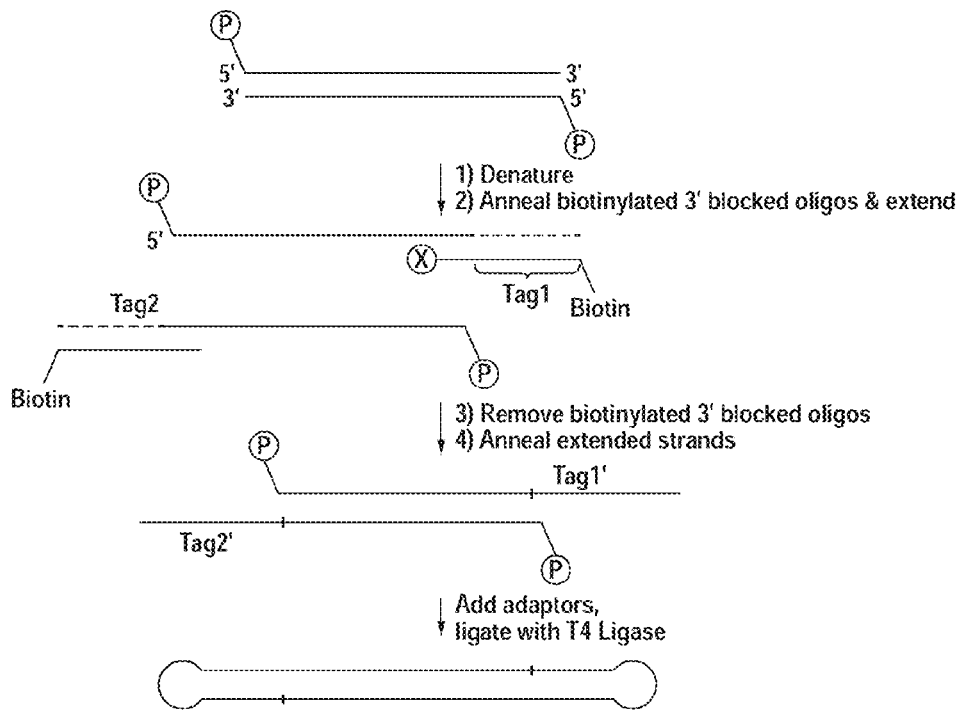
In FIG. 20B, the 3' blocked oligonucleotides are conjugated to biotin.

Preferably, the 3' blocked oligonucleotides are removed from the reaction mixture following formation of the extended nucleic acid strands. Accordingly, the 3' blocked stem-loop oligonucleotide can include one or more (e.g., a plurality of) modified nucleobase units, such as deoxyribouracil nucleobase units, nucleobase units directly linked to a solid support, or nucleobase units having an affinity tag (e.g., biotin, as shown in FIG. 20B). Such modifications are discussed above in connection with Method 20. Alternatively, the 3' blocked oligonucleotides can be separated based on size, e.g., in a size exclusion column. Depending on the method of separation, 3' blocked oligonucleotides hybridized to extended nucleic acid strands can be dissociated from the extended nucleic acid strands (e.g., by denaturation) prior to performing the separation step, particularly if the step involves affinity-based separation or size exclusion chromatography.

The stem-loop adaptor(s) used in the method can be, e.g., any stem-loop adaptor described herein. Typically, each stem-loop adaptor include a 5' phosphate group, a 5' segment having a stem-loop structure, a 3' segment, and a 3' end hydroxyl. The 3' segment can be complementary to a 3' extension, or a 3'-most sub-segment thereof, of a 3' extended nucleic acid. Thus, for example, the 3' segment can have a common sequence with the 5' segment of a 3' blocked oligonucleotide. The 5' and 3' segments of the stem-loop adaptor(s) can be directly linked to each other (e.g., with no intervening segment) or they can be linked by an intervening segment. An intervening segment can be particularly useful is the 3' extended nucleic acid is produced by extension using a polymerase, such as Taq polymerase, that tends to add additional, non-template directed nucleobase units at the 3' end of a polymerized strand. Accordingly, a suitable intervening segment can be, e.g., a T nucleobase unit or a poly-T sequence (e.g., a sequence of 2, 3, or 4 T nucleobase units).

Denaturation of duplex nucleic acids (e.g., template nucleic acid, nucleic acids having defined ends, extended nucleic acids including stem-loop primers) and annealing of primers can be achieved using standard techniques, such as varying temperature and/or ionic strength of the buffer.

Variation 1

In a variation of Method 21, the subsequent set of steps in the method involve the use of a single stem-loop adaptor that hybridizes to only one 3' extended nucleic acid strand. In this variation, only a single strand of 3' extended nucleic acid is incorporated into a closed nucleic acid structure, similar to Method 16 when only a single stem-loop adaptor is used (the key difference being that the present variation involves target strand extension during the initial steps of the method rather than target amplification).

With regards to the nucleic acid having defined ends used in this variation of the method, only the strand that is to be incorporated into a closed nucleic acid structure needs to have a 5' phosphate group. Accordingly, if the nucleic acid having defined ends is prepared by amplification, only one of the amplification primers (i.e., the amplification primer that becomes part of the strand to be incorporated into a closed nucleic acid structure) needs to include a 5' phosphate group. However, if both amplification primers include a 5' phosphate group, then each strand of the nucleic acid having defined ends can be incorporated into a closed nucleic acid structure, e.g., in separate reactions using different stem-loop adaptors.

Figure 20C:
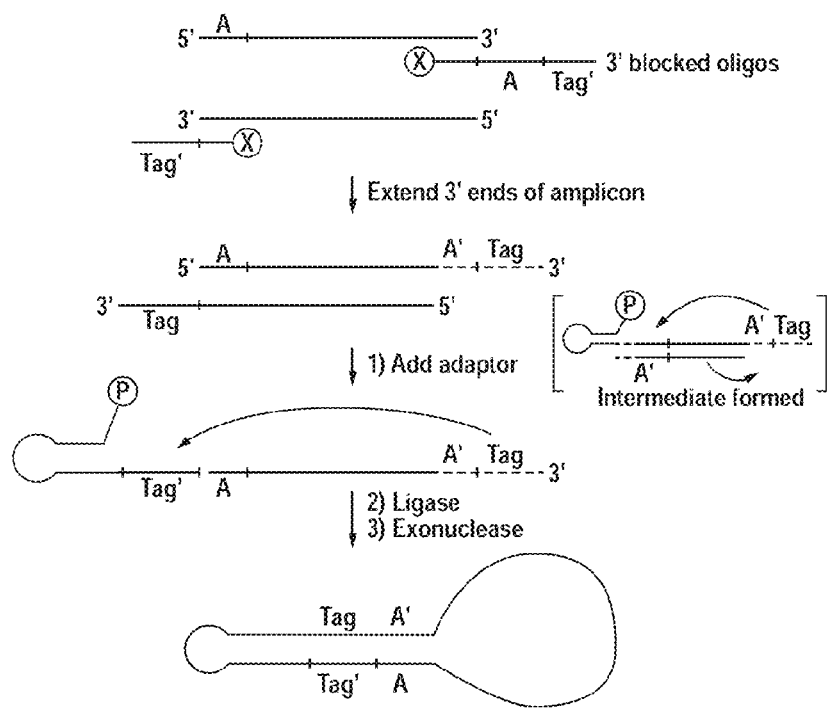
In FIG. 20C, a single stem-loop adaptor is used to generate a closed nucleic acid structure comprising a single strand of the template.

This variation of the method can be practiced with two 3' blocked oligonucleotides, as depicted in FIG. 20C, but only one 3' blocked oligonucleotide is needed (i.e., the 3' blocked oligonucleotide used to create the 3' extended nucleic acid strand that gets incorporated into a closed nucleic acid structure). The 3' blocked oligonucleotide(s) can be any of the 3' blocked oligonucleotides described above. When a pair of 3' blocked oligonucleotides is used, the oligonucleotides typically include 3' target-binding segments (i.e., segments complementary to 3' end segments of the nucleic acid having defined ends) and 5' segments that have a common sequence (e.g., a common sequence tag, as depicted in FIG. 20C). Preferably, at least one of the 3' blocked oligonucleotides includes an intervening segment. The intervening segment can be complementary to a 5' end segment of a strand of denatured nucleic acid (e.g., a 5' segment, or a 5'-most sub-segment thereof, of the denatured nucleic acid strand to which the oligonucleotide hybridizes, as depicted in FIG. 20C). Such an intervening segment can, e.g., facilitate the formation of a closed nucleic acid structure (e.g., by providing a segment in the 3' extension of the extended nucleic acid strand that is complementary to the 5' end segment of the same strand). Thus, for example, the method can be practiced with a single 3' blocked oligonucleotide that includes an intervening segment. Alternatively, the method can be practiced with a two 3' blocked oligonucleotides, wherein one of the oligonucleotides includes an intervening segment and the 5' segments of the two oligonucleotides have a common sequence.

If neither of the 3' blocked oligonucleotides includes an intervening segment, preferably the 3' end segment of the strand of nucleic acid having defined ends, or a 3'-most sub-segment thereof (e.g., consisting of 1, 2, 3, 4 or more nucleobase units) is complementary to a 5' end segment of the same strand. The complementarity need not be perfect providing that at least the 3'-most nucleobase unit of the 3' end segment is complementary to the 5'-most nucleobase unit of the 5' end segment. Similar to the intervening segment, this complementarity can facilitate formation of a closed nucleic acid structure. Nucleic acids having 1, 2, 3, 4, or more complementary nucleobase units at their 5' and 3' ends can be prepared in a variety of ways, including selection of the 5' and 3' ends of a target nucleic acid, amplification of target nucleic acid using primers that have 5' segments that have a common sequence, restriction endonuclease digestion of doublestranded target nucleic acid, optionally followed by fill-in of 3' overhangs or removal of 5' overhangs.

The stem-loop adaptor used in this variation of the method can, e.g., be as described above. Without intending to be bound by theory, it is believe that the stem-loop adaptor can form a complex with both the 3' extended nucleic acid strand and the complement strand thereof (whether extended or not). As depicted in FIG. 20C, having two 3' extended nucleic acid strands that have a common sequence in their 3' extensions (e.g., a common tag sequence) can facilitate the formation of the nicked intermediate by providing two 3' extensions (rather than just one) to which the 3' segment of the stem-loop adaptor can hybridize.

This variation of the method can further include the use of blocker oligonucleotides to block intermolecular hybridization of the extended nucleic acid strand to the complement strand thereof (e.g., complement denatured nucleic acid strand, when only one strand is extended). The blocker oligonucleotides can hybridize to the complement strand, e.g., in the manner depicted in FIG. 15B. The method can also include the use of an exonuclease step after ligation of the nicked intermediate to remove the complement strand.

XVII. Method 22

At a general level, method 22 involves two main steps, or sets of steps. In the initial set of steps, the strands of a double-stranded nucleic acid having defined ends are extended. In a subsequent set of steps, the extended nucleic acid strands are allowed to intermolecularly hybridize, thereby forming a circularized intermediate having a nicked duplex segment and a single-stranded segment. Ligation of the intermediate produces a closed nucleic acid structure having duplex and single-stranded segments.

Figure 21:
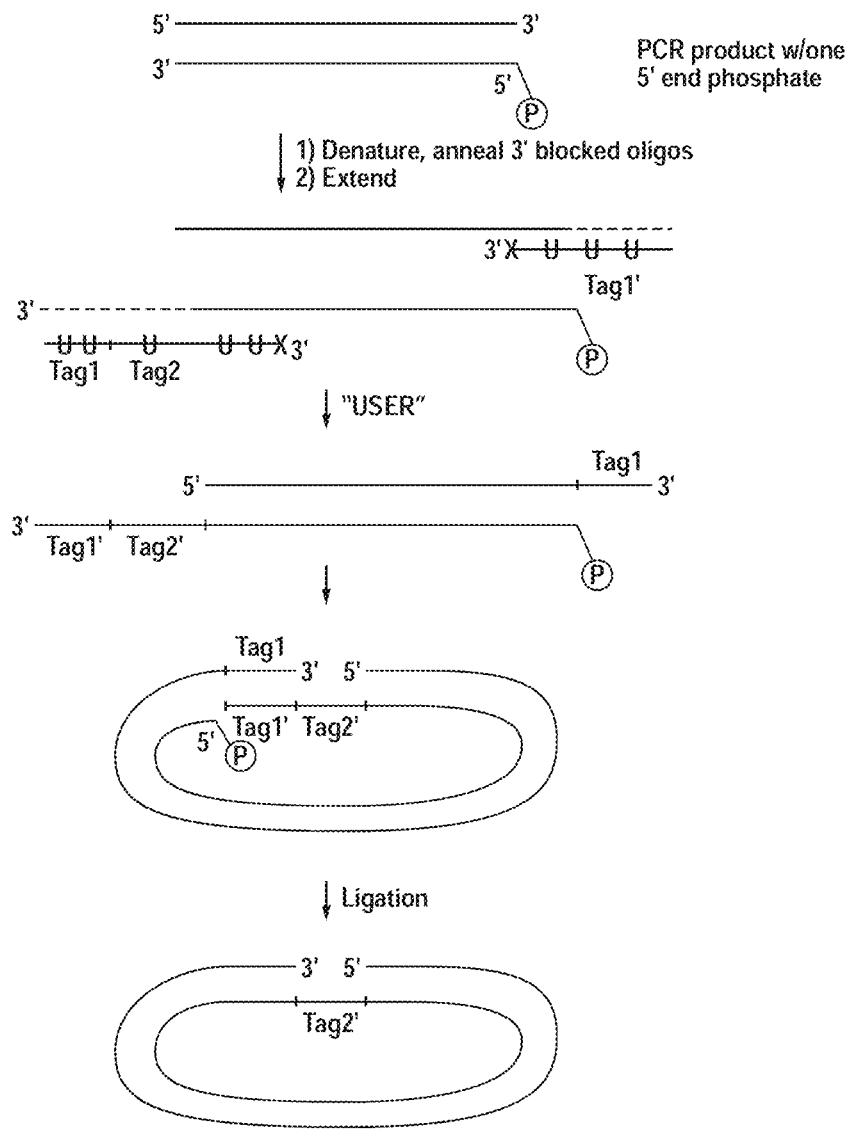
FIG. 21 illustrates an exemplary form of method 22 for generating a closed nucleic acid structure comprising an initial step of template extension with a pair of 3' blocked oligonucleotides to add tags to the 3' ends of the strands of a nucleic acid having defined ends, and a subsequent set of steps in which the 3' blocked oligonucleotides are removed and the strands of the extended nucleic acid are allowed to intermolecularly hybridize to form a nicked intermediate that is readily ligated.

FIG. 21 shows an exemplary form of method 22 wherein the strands of a double-stranded nucleic acid having defined ends (e.g., a target nucleic acid) are extended using 3' blocked oligonucleotides. Basically, in the initial set of steps, a double-stranded nucleic acid having defined ends is denatured to yield two strands of denatured nucleic acid. Each strand of denatured nucleic acid includes a 5' phosphate group, a region of interest from a target nucleic acid, and a 3' end segment. A pair of 3' blocked oligonucleotides is annealed to the strands of denatured nucleic acid. Each 3' blocked oligonucleotide includes a 5' segment, a 3' segment, and a plurality of deoxyribo-uracil nucleobase units. The 3' segments of the oligonucleotides are complementary to 3' end segments of the denatured nucleic acid strands and the 5' segments provide sequence tags that are complementary to each other. A first oligonucleotide of the pair further includes an intervening segment that links the 5' and 3' segments. Annealing of the 3' segment of each 3' blocked oligonucleotide to a 3' end segment of a strand of denatured nucleic acid provides a template for extension of the denatured nucleic acid strand. Polymerase-mediated extension of the denatured nucleic acid strands produces first and second 3' extended nucleic acid strands. The 3' extended nucleic acid strands include the 5' phosphate group and target nucleic acid region of interest (or complement thereof) from a denatured nucleic acid strand. In addition the 3' extended nucleic acid strands include 3' extensions that end with a 3' hydroxyl group. The 3' extension of the first 3' extended nucleic acid strand is complementary to the 5' and intervening segments of the first 3' blocked oligonucleotide, while the 3' extension of the second 3' extended nucleic acid strand is complementary to the 5' segment of the second 3' blocked oligonucleotide.

In the subsequent set of steps, the 3' blocked oligonucleotides are removed (e.g., degraded) by enzymatic excision of the deoxyribo-uracil nucleobase units. The 3' extended nucleic acid strands are then allowed to intermolecularly hybridize. The target nucleic acid region of interest from the first and second 3' extended strands form a duplex target nucleic acid and the segments of the 3' extensions complementary to the 5' segments of the first and second oligonucleotides likewise form a duplex. The resulting nucleic acid intermediate is circularized and includes a nicked duplex segment and a single-stranded segment complementary to the intervening segment of the first oligonucleotide. A nick in the duplex segment of the intermediate separates the 5' phosphate and 3' hydroxyl groups of the first 3' extended target nucleic acid strand. Ligation of the circularized nucleic acid intermediate produces a closed nucleic acid structure having duplex and single-stranded segments.

The double-stranded nucleic acid having defined ends can be a double-stranded target nucleic acid or can be obtained from a target nucleic acid, e.g., as described above in connection with Method 16. Target nucleic acid used to generate nucleic acid having defined ends can be double-stranded or single-stranded. The target nucleic acid can be any type of target nucleic acid described herein, including genomic DNA, cloned fragments, including large nucleic acid clones (e.g., cosmids, BACs, YACs and so forth), amplified fragments (e.g., amplified by PCR) such as cDNA, RNA, and so forth. The nucleic acid having defined ends can be obtained (e.g., produced) from the target nucleic acid by amplification, e.g., using a linear primer pair, as discussed above. Thus, the linear primers can be standard PCR primers or they can include a sequence tag. Linear primers can include a 3' target-binding segment and a 5' segment (e.g., a target-binding segment or a sequence tag). Typically, at least one of the linear primers include a 5' phosphate (i.e., the primer that is incorporated into the strand of nucleic acid having defined ends that is extended to become the first 3' extended nucleic acid strand).

A nucleic acid having defined ends can be obtained from target nucleic acid by means other than just amplification. For example, a primer and a blocker oligonucleotide can be used to generate a single-stranded nucleic acid having defined ends, e.g., as described in variation 4 of Method 16, and the single-stranded nucleic acid can be converted into a double-stranded nucleic acid, e.g., by amplification or extension of a primer that binds to the 3' end of the single-stranded nucleic acid. Alternatively, nucleic acid having defined ends can be generated by digesting double-stranded target nucleic acids with restriction endonucleases and, optionally, filling-in or removing any 3' or 5' overhangs generated by the restriction endonucleases.

The 3' blocked oligonucleotides can be, e.g., any linear oligonucleotide described herein, provided that (1) binding of the oligonucleotides to the strands of the nucleic acid having defined ends provides a template for extension of the nucleic acid strands, and (2) the 3'-most nucleobase unit of the oligonucleotide blocks polymerase-mediated extension of the oligonucleotide. 3'-most nucleobase units suitable for blocking polymerase-mediated extension are described, e.g., in the general description of target extension oligonucleotides provided above. Typically, the 3' blocked oligonucleotides include a 5' segment complementary to the 5' segment of the other oligonucleotide in the pair and a 3' segment complementary to a 3' end segment of a strand of nucleic acid having defined ends. If the nucleic acid having defined ends is an amplification product, the 3' segment of a 3' blocked oligonucleotide can be complementary to all or part (e.g., a 5' segment) of a linear primer used in the amplification reaction. One of the 3' blocked oligonucleotides in the pair (e.g., a first 3' blocked oligonucleotide) includes an additional intervening segment (i.e., segment) that links the 3' and 5' segments. The intervening segment can, e.g., include at least 1, 2, 3, 4, 5, 6, 7, 8 or more nucleobase units and up to 10, 15, 20 or more nucleobase units, including all permutations of upper and lower limits. The intervening segment can have a size sufficient (e.g., optimized) to provide a polymerase binding site on a closed nucleic acid structure that includes a single-stranded segment complementary to the intervening segment.

Preferably, the 3' blocked oligonucleotides are removed from the reaction mixture following formation of the extended nucleic acid strands. Accordingly, the 3' blocked stem-loop oligonucleotide can include one or more (e.g., a plurality of) modified nucleobase units, such as deoxyribouracil nucleobase units, nucleobase units directly linked to a solid support, or nucleobase units having an affinity tag (e.g., biotin). Such modifications are discussed above in connection with Method 20. Alternatively, the 3' blocked oligonucleotides can be separated based on size, e.g., in a size exclusion column. Depending on the method of separation employed, 3' blocked oligonucleotides hybridized to extended nucleic acid strands can be dissociated from the extended nucleic acid strands (e.g., by denaturation) prior to performing the separation step, particularly if the step involves affinity-based separation or size exclusion chromatography.

Denaturation of duplex nucleic acids (e.g., template nucleic acid, nucleic acids having defined ends, extended nucleic acids including stem-loop primers) and annealing of primers can be achieved using standard techniques, such as varying temperature and/or ionic strength of the buffer.

XVIII. Method 23

At a general level, method 23 involves two main steps, or sets of steps. In the initial set of steps, a target nucleic acid is amplified and the ends of the amplicon are extended. In a subsequent set of steps, stem-loop adaptors are annealed to 3' extensions of the amplicon, thereby forming a nicked intermediate that is readily ligated to form a closed nucleic acid structure.

Figure 22A:
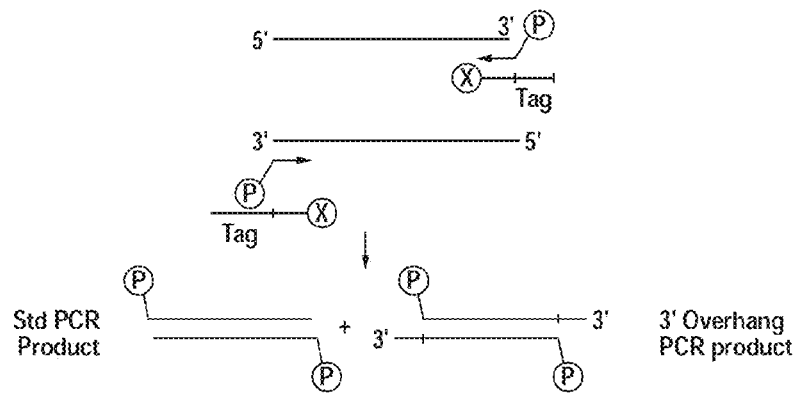
FIGS. 22A, B illustrate an exemplary form of method 23 for generating a closed nucleic acid structure comprising an initial step wherein a mixture of a linear primer pair and a pair of 3' blocked oligonucleotides are used to amplify and add sequence tags to a target nucleic acid having defined ends, and a subsequent step wherein a pair of stem-loop adaptors are annealed to the amplified nucleic acid to form a nicked intermediate that is readily ligated.
Figure 22B:
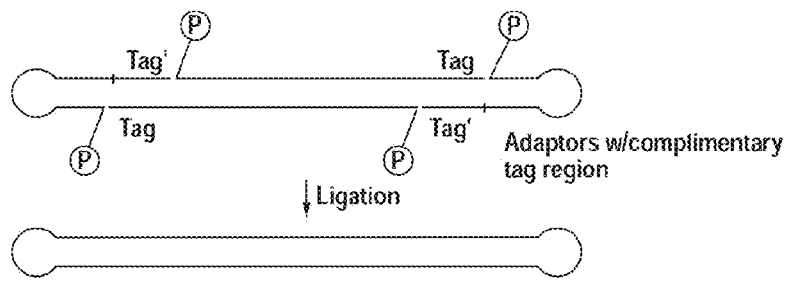

FIGS. 22A, B show an exemplary form of method 23 wherein a target nucleic acid is amplified and the 3' ends of the amplified nucleic acid are extended in the same reaction mixture. Basically, in the initial set of steps, a target nucleic acid is amplified using a pair of linear primers. The linear primers each include a 5' phosphate group and a 3' target-binding segment. The amplification reaction further includes a pair of 3' blocked oligonucleotides. Each 3' blocked oligonucleotide includes a 5' segment and a 3' segment complementary to a 3' end segment of a strand of amplified nucleic acid. The 5' segments of the oligonucleotides provide sequence tags. The reaction is set up (e.g., as a PCR reaction) so that primer-dependent amplification and oligonucleotide-dependent template extension can occur at the same time. After running the reaction, there is a mixture of different amplification/extension products, including 3' extended, amplified nucleic acid, as depicted in FIGS. 22A and B. Each strand of the 3' extended, amplified nucleic acid (i.e., 3' extended target nucleic acid duplex) includes a 5' phosphate group, a segment of the target nucleic acid (or the complement thereof), and a 3' extension complementary to a 5' segment of a 3' blocked oligonucleotide.

In the subsequent set of steps, the 3' extended, amplified nucleic acid is contacted with a pair of stem-loop adaptors. Each adaptor includes a 5' phosphate group, a 5' segment having a stem-loop structure, a 3' segment that has a common sequence with a 5' segment of one of the 3' blocked oligonucleotides, and a 3' hydroxyl group. Annealing of the stem-loop adaptors to the 3' extensions of the 3' extended, amplified nucleic acid produces a nicked intermediate in which the 5' phosphate groups of the stem-loop adaptors are adjacent to, but separated by a nick from, a 3' hydroxyl groups of a strand of the 3' extended, amplified nucleic acid and the 5' phosphate groups of the strands of the 3' extended, amplified nucleic acid are adjacent to, but separated by a nick from, the 3' hydroxyl groups of the stem-loop adaptors. The nicked intermediate is contacted with a ligase that seals the nicks, thereby producing a closed nucleic acid structure. The closed nucleic acid structure includes a double-stranded segment of target nucleic acid wherein the two strands are joined to one another by stem-loop structures.

The target nucleic acid used in this method can be double-stranded or single-stranded. The target nucleic acid can be any type of target nucleic acid described herein, including genomic DNA, cloned fragments, including large nucleic acid clones (e.g., cosmids, BACs, YACs), amplified fragments (e.g., amplified by PCR) such as cDNA or RNA, among others. The target nucleic acid can be a nucleic acid having defined ends. Nucleic acid having defined ends can be obtained (e.g., produced) by amplification, e.g., using a linear primer pair. The linear primers can be standard PCR primers or they can include a sequence tag. Alternatively, nucleic acid having defined ends can be obtained, e.g., as described in variation 4 of Method 16, using a primer and blocker oligonucleotide. Nucleic acid having defined ends can also be generated by digesting double-stranded target nucleic acids with restriction endonucleases and, optionally, filling-in or removing any 3' or 5' overhangs generated by the restriction endonucleases.

The primers used to amplify the target nucleic acid can be, e.g., linear primers, as described herein. Typically, the primers include a 5' phosphate group and a 3' target-binding segment. The primers can further include a 5' segment, such as a sequence tag. The sequence tag can be relatively short, e.g., consisting of less than 10 nucleobase units (e.g., consisting of 1, 2, 3, 4, or 5 nucleobase units). Short sequence tags preferably have a high GC content. Alternatively, the sequence tag can be relatively long, e.g., consisting of at least 10 nucleobase units (e.g., at least 15, 20, 25 or more nucleobase units). The longer sequence tags can be highly selective, hybridizing only poorly or not at all to other nucleic acids (e.g., the target nucleic acid) present in the amplification reaction. Examples of selective sequence tags include, e.g., xTAG®'s, as described herein.

The 3' blocked oligonucleotides can be, e.g., any linear oligonucleotide described herein, provided that (1) hybridization of the oligonucleotides to the strands of amplified nucleic acid provides a template for extension of the amplified nucleic acid strands, and (2) the 3'-most nucleobase unit of the oligonucleotide blocks polymerase-mediated extension of the oligonucleotide. 3'-most nucleobase units suitable for blocking polymerase-mediated extension are described, e.g., in the general description of target extension oligonucleotides provided above. Typically, the 3' blocked oligonucleotides include a 5' segment and a 3' segment. The 3' segment is complementary to a 3' end segment of a strand of amplified nucleic acid. For example, the 3' segment of a 3' blocked oligonucleotide can have a common sequence with all or part (e.g., a 5'-most sub-segment) of a linear primer of the primer pair. The 5' segments of the 3' blocked oligonucleotides can provide sequence tags. The sequence tags can, e.g., have different sequences or they can have a common sequence. If the sequence tags of the 5' segments have a common sequence, only a single stem-loop adaptor is required in the subsequent steps of the method.

Optionally, one or both of the primers used to amplify the target nucleic acid and/or one or both of the 3' blocked oligonucleotides is attached to a solid support, such as glass, a polymeric surface, a microchip, a column, or a bead. Attaching the primers and/or 3' blocked oligonucleotides to a solid support can facilitate their removal from the reaction prior to annealing stem-loop adaptors to the 3' extended amplified nucleic acid. Accordingly, the primers and/or 3' blocked oligonucleotides can be directly linked to a solid support or can include one or more modified nucleobase units that can provide an indirect linkage to a solid support, such as an affinity tag (e.g., biotin, avidin, his-tag and the like). Removal of primers and/or oligonucleotides that are linked to a solid support can be performed, e.g., as described herein. Alternate methods of removing the primers and/or oligonucleotides include uracil excision of primers and oligonucleotides that include one or more deoxyribo-uracil nucleobase units, or size exclusion chromatography, as discussed herein.

The stem-loop adaptor(s) used in the method can be, e.g., any stem-loop adaptor described herein. Typically, each stem-loop adaptor include a 5' phosphate group, a 5' segment having a stem-loop structure, a 3' segment, and a 3' end hydroxyl. The 3' segment can be complementary to a 3' extension of a 3' extended, amplified nucleic acid. Thus, for example, the 3' segment can have a common sequence with the 5' segment of a 3' blocked oligonucleotide. The 5' and 3' segments of the stem-loop adaptor(s) can be directly linked to each other (e.g., with no intervening segment) or they can be linked by an intervening segment. An intervening segment can be particularly useful if the 3' extended, amplified nucleic acid is produced using a polymerase, such as Taq polymerase, that tends to add additional, non-template directed nucleobase units at the 3' end of a polymerized strand. Accordingly, a suitable intervening segment can be, e.g., a T nucleobase unit or a poly-T sequence (e.g., a sequence of 2, 3, or 4 T nucleobase units).

Denaturation of duplex nucleic acids (e.g., template nucleic acid, nucleic acids having defined ends, extended nucleic acids including stem-loop primers) and annealing of primers can be achieved using standard techniques, such as varying temperature and/or ionic strength of the buffer.

XIX. Amplification

The target nucleic acid is contacted with a primer or a pair of primers under conditions suitable for amplification, usually but not necessarily by the polymerase chain reaction PCR. Suitable PCR conditions include a suitable buffer, polymerase, nucleobase units for incorporation and thermocycling. Exemplary conditions use 2-50 cycles each cycle including a denaturing step (e.g. 10 seconds at 94° C.), an annealing step (e.g. 15 sec at 68° C.), and an extension step (e.g. 1 minute at 72° C.). The number of cycles can be at least 1, 2, 5, 10, 20, 30, 50 thermocycles but is sometimes less than conventional PCR (e.g., between 2, 3, 4 to 5 on the lower end and 10, 15 or 20 cycles on the upper end including any permutation of upper and lower limits).

PCR is described by (U.S. Pat. Nos. 4,683,195, 4,683,202, 4,800,159 and 4,965,188, commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988). For example, the target is RNA it can first be converted to DNA by RT-PCR. An RNA target can also be directly amplified in a PCR reaction or cycled primer extension reaction using a RNA-directed DNA polymerase such as Tth DNA polymerase.

Other amplification techniques that can be used include transcription-mediated amplification (e.g., TMA), ligase chain reaction (LCR), strand displacement amplification (SDA), and nucleic acid sequence based amplification (NASBA). Whereas PCR reverse transcribes RNA to DNA prior to amplification (e.g., RT-PCR), TMA and NASBA can directly amplify RNA.

Transcription-Mediated Amplification (U.S. Pat. Nos. 5,480,784 and 5,399,491), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518. In a variation described in U.S. Publ. No. 20060046265, TMA optionally incorporates the use of blocking moieties, terminating moieties, and other modifying moieties to improve TMA process sensitivity and accuracy.

Strand displacement amplification (Walker et al., *Proc. Natl. Acad. Sci. USA* 89: 392-396 (1992); U.S. Pat. Nos. 5,270,184 and 5,455,166), commonly referred to as SDA, uses cycles of annealing pairs of primer sequences to opposite strands of a target sequence, primer extension in the presence of a dNTPs to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

The ligase chain reaction (Weiss, *Science* 254: 1292 (1991) commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Other amplification methods include, for example: nucleic acid sequence based amplification (U.S. Pat. No. 5,130,238), commonly referred to as NASBA; one that uses an RNA replicase to amplify the probe molecule itself (Lizardi et al., *BioTechnol.* 6: 1197 (1988, commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990). For further discussion of known amplification methods see Persing, "In Vitro Nucleic Acid Amplification Techniques" in *Diagnostic Medical*

*Microbiology: Principles and Applications* (Persing et al., Eds.), pp. 51-87 (American Society for Microbiology, Washington, D.C. (1993)).

If an amplification technique other than PCR is used, standard conditions including a polymerase, nucleobase units, and buffer for such other technique can be used.

Following amplification, primer extension, or 3' extension, the resulting nucleic acid (e.g., amplicon, extension product, 3' extended nucleic acid strand) can be purified, as needed, to facilitate subsequent steps in the methods of the invention. Such purification is performed according to conventional techniques including the use of standard kits, such as the QIAquick PCR Purification Kit, elution columns, (e.g., Qiagen MinElute columns), and the like.

XX. Ligation

The closed nucleic acids containing nicks can be ligated using a nucleic acid ligase. The ligase joins a 5' phosphate group on a first strand to an adjacent hydroxyl on the same or a different strand.

A variety of ligases can be used. Nucleic acid ligases are a family of enzymes which catalyze the formation of a covalent phosphodiester bond between two distinct nucleic acid strands, i.e. a ligation reaction. Examples of nucleic acid ligases include DNA ligases and RNA ligases. A DNA ligase means any protein or peptide, of synthetic, recombinant or natural origin, exhibiting a DNA ligase activity, i.e., catalyzing the formation of a covalent phosphodiester bond between two distinct DNA strands. Examples of DNA ligases include the ATP-dependent T4 DNA ligase (isolated from the T4 phage) and the $NAD^+$-dependent DNA ligase from *E. coli*. Both enzymes catalyze the synthesis of a phosphodiester bond between the 3'-hydroxyl group of one nucleic acid strand, and the 5'-phosphoryl group, of a second nucleic acid strand, for instance at a nick between the two strands which are both hybridized to a third DNA strand. RNA ligases, which are a related family of enzymes, catalyze the ligation of nicked RNA ends hybridized on to RNA or DNA in an analogous fashion.

Thermostable or non-thermostable ligases can be used. DNA ligases useful for the present method also include natural DNA ligases or fragments, derivatives or analogues with at least 90%, 95%, or 98% identity to a natural DNA ligase, such as an *E. coli* DNA ligase, a DNA ligase from thermophilic bacteria, e.g., ligases from the genus *Thermus* including ligases from *T. aquaticus, T. thermophilus, T. rubber, T. filiformis, T. brockianus, T. flavus* and *T. scotoductus*. When a thermophilic DNA ligase is used, the ligation can be performed at a temperature, e.g., over 40, 50, 60, or 70 degrees.

The ligated nucleic acid product can be purified to remove linear nucleic acids or other impurities and undesired side products. Standard methods such as gel purification, nucleic acid binding supports (e.g., AMPure beads from Beckman genomics), or affinity chromatography can be utilized. Furthermore, linear nucleic acids can be removed from the mixture with the use of exonucleases.

For example, the ligated nucleic acid product can be purified by using a "capture probe" bound to a substrate, such as a magnetic bead. Examples of capture probe methodologies are described by Ranki et al., U.S. Pat. No. 4,486,539, Stabinsky, U.S. Pat. No. 4,751,177, Weisburg et al., U.S. Pat. No. 6,110,678, Becker et al., U.S. Pat. No. 8,034,554, and Becker et al., U.S. Pat. App. Pub. No. 2009/0286249. Capture probes are generally short sequences of nucleic acid (i.e., oligonucleotide) capable of hybridizing, under stringent hybridization conditions, with the ligated nucleic acid product. Magnets in close proximity to the reaction vessel are used to draw and hold the magnetic beads to the side of the vessel. Once the ligated nucleic acid product is immobilized, the hybridized nucleic acid can be separated from non-hybridized nucleic acid by aspirating fluid from the reaction vessel and optionally performing one or more wash steps.

XXI. Sequencing

A closed nucleic acid structure as generated by the above methods is suitable for a number of subsequent procedures, including sequence analysis of the target nucleic acid. Sequencing can be performed by template-directed extension starting from a sequencing primer or a free 3' hydroxyl of the closed nucleic acid structure. The extension is directed by the closed nucleic acid structure and incorporates supplied nucleobase units into a nascent chain. Extension initiated at the sequencing primer or the free 3'-hydroxyl can proceed around the closed nucleic acid structure and can continue around the circle multiple times generating alternating copies of one or both strands of the target nucleic segment and a portion of the template other than the target segment. The target nucleic acid segment is usually of unknown sequence and the rest of the template, which can originate from the primers or adaptors in the present methods, is usually of known sequence. The multiple reads of a strand of the target nucleic acid segment may contain sequencing errors. Combination of these multiple reads to provide a consensus sequence can eliminate at least some of the sequencing errors and improve sequencing accuracy. Some methods used an extension blocking primer in one or more steps for constructing the closed nucleic acid molecule, resulting in a closed nucleic acid structure containing one or more extension blockers. Subsequent procedures for which the closed nucleic acid structure is used in a reaction that includes nucleobase unit extension by a nucleic acid polymerase, will require that the extension blocker inhibition is reversed. For example, if the extension blocker was a non-canonical nucleobase for which a base paring non-canonical nucleobase is available, then that base pairing nucleobase is included in the reaction. Similarly, if the extension blocker was a reversibly modified nucleotide, then that modification is removed. Also, if the extension blocker was a nucleotide that is incompatible with a certain polymerase, then a compatible polymerase is added to the reaction.

The sequencing can be in real-time or non-real time. Real-time sequencing means that incorporated nucleobase units can be detected contemporaneous with incorporation (i.e., before a subsequent nucleobase unit is incorporated). Alternatively sequencing can be non-real time meaning that incorporated nucleobase units are detected after formation of a nascent chain or at least after incorporation of the next nucleobase unit.

The sequencing can be single-molecule template or multi-molecule template. Single-molecule sequencing means that an individual sequence is read from an individual closed nucleic acid structure molecule. Multi-molecule sequencing means that a plurality of template molecules are sequenced together to generate a consensus sequence without resolving individual template sequences. A consensus sequence means a sequence formed from the most frequently represented nucleobase units at each position with the possible exception that at certain positions a majority nucleobase unit and at least one minority nucleobase unit are designated. In such sequencing, the plurality of templates usually contain copies of the same target nucleic acid segment, which can be identical among different templates or show variation due to variants of the target nucleic acid sequence (e.g., allelic or viral variants). Sequencing a plurality of templates simultaneously detects incorporation of a consensus nucleobase unit at successive positions of a nascent chain. If variation is present among the target nucleic acid segments in the template, majority and minority nucleobase units can sometimes be detected at the positions of such variation.

In some methods, the nucleobase units being incorporated include fluorescent (or other detectable) labels. Preferably, each of the different nucleobase units used bears a different fluorescent (or other) label to allow differential detection of the nucleobase units. However, in some methods different nucleobase units have the same label. In such methods, the different nucleobase units can be distinguished by being supplied sequentially.

Incorporation of a nucleobase unit can be detected by measuring the presence of label on a nucleobase unit being incorporated. In some methods, the incorporation of nucleobase units is detected by measuring the release of a label from the nucleobase unit being incorporated. A preferred approach as with SMRTbell™ template sequencing is to use nucleobase units fluorescently labeled on the terminal phosphate of the nucleobase unit (Korlach et al., *Nucleosides, Nucleotides and Nucleic Acids,* 27:1072-1083, 2008). The label is cleaved from the nucleotide monomer on incorporation of the nucleotide into the polynucleotide. Accordingly, the label is not incorporated into a nascent nucleic acid, increasing the signal:background ratio. Sequencing can be performed in a single-molecule, real-time (SMRT™) format as described in U.S. Pat. Nos. 7,181,122, 7,302,146, and 7,313,308. In such a format, closed nucleic acid structures are sequenced individually and an incorporated nucleobase unit is detected in real time before incorporation of the next incorporated nucleobase unit. Sequencing of an individual templates can take place in a cylindrical metallic chamber known as a zero mode waive guide, and many such individual templates each in its own zero mode waive guide can be sequenced in parallel.

Another nucleobase unit uses a fluorescent dye linked to photocleavable chemical moiety to cap the 3'-OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777,013; Williams et al., U.S. Pat. No. 7,645,596; Kao et al, U.S. Pat. No. 6,399,335; Nelson et al., U.S. Pat. Nos. 7,052,839 & 7,033,762; Kumar et al., U.S. Pat. No. 7,041,812; Sood et al, US Pat. App. No. 2004-0152119; Eid et al., Science 323, 133 (2009)).

In some methods, the incorporation of nucleobase units into the nascent chain is detected by measuring a chemical change that occurs during the incorporation of nucleobase units. The chemical change can be a change in pH as for the Ion Torrent Personal Genome Machine (Guilform, Conn.), which detects hydrogen ions. The chemical change can alternatively or additionally be release of a pyrophosphate. Pyrosequencing detects the release of inorganic pyrophosphate (PPi) as particular nucleotides are incorporated into the nascent strand (Ronaghi, et al., *Analytical Biochemistry* 242 (1):84-9, 1996; Ronaghi, M., *Genome Res.* 11(1):3-11, 2001; Ronaghi, et al., *Science* 281(5375):363, 1998; U.S. Pat. Nos. 6,210,891, 6,258,568 and 6,274,320). Released PPi can be detected by, e.g., a process in which the released PPi is immediately converted to adenosine triphosphate (ATP) by ATP sulfurylase, and the level of ATP generated is detected via luciferase-produced photons measuring pyrophosphate release on testing DNA/polymerase complexes with each deoxyribonucleotide triphosphate (dNTP) separately and sequentially.

XXII. Target Nucleic Acids

A target nucleic acid refers to a nucleic acid molecule or population of related nucleic acid molecules that is or may be present within a sample. A target nucleic acid segment is part of a target nucleic acid defined by the primers used for its amplification. The length of the target segment is determined by the capacity of amplification technology, sequencing technology (length of sequencing read) and whether some or all of the target nucleic acid is of interest to sequence. The segment can range from about ten nucleotides to more than 1000 nucleotides or up to 10,000 nucleotides or even greater than 10,000 nucleotides. Segments of target nucleic acids having 25-10,000 nucleotides are common.

A target nucleic acid can exist in different forms, i.e., single-stranded, double-stranded, triple-stranded, or mixtures thereof, such as in a partially double-stranded hairpin structure or partially double-stranded duplex structure, and a target segment can present on any strand (sense or anti-sense) of the structure. A target nucleic acid can be RNA (e.g., viral RNA, micro RNA, mRNA, cRNA, rRNA, hnRNA or DNA (genomic DNA, extrachromasomal DNA, mitochondrial DNA, plasmid DNA or cDNA) among others. The target nucleic acid can be from a pathogenic microorganism, such as a virus, bacteria or fungus, or can be endogenous to a patient. A target nucleic acid can be synthetic or naturally occurring.

Viral nucleic acids (e.g., genomic, mRNA) form a useful target for analyses of viral sequences. Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is particularly useful for analyzing drug resistance. Viruses mutate rapidly so that a patient is often infected with a heterogeneous population of viral nucleic acids including majority and minority forms, which changes over time. Some of the mutations differentiating species of the heterogeneous population may be associated with resistance to a drug that the patient has been treated with or may be treated with in the future. Deconvolution of the population to detect individual variants allows detection of drug resistant mutations and their change over time, thus allowing treatment regimes to be customized to take into account the drug resistance of strains infecting a particular patient. Because drug-resistant or other mutations may present as only a small proportion of viral nucleic acid molecules, sequencing of a large number of molecules in the viral nucleic population may be required to provide a high likelihood of identifying all drug resistant mutations or at least all, whose representation as a percentage of the total viral nucleic acid population exceeds a threshold.

Human nucleic acids are useful for diagnosing diseases or susceptibility towards disease (e.g., cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses. The methods are particularly useful for analyzing target nucleic acids or segments thereof including site(s) of polymorphic variation between individuals, such as multiallelic genes. In heterozygotic individuals, two or more variants of a target nucleic acid are present in a single sample. The variants can pair with one another in PCR forming a heteroduplex. If both strands of a target nucleic acid are read from a circular duplex, then the different allelic sequences may be unwittingly combined into a single consensus sequence. However, in the present methods only one strand target strand is read from a given template so that variant alleles read from different templates are kept separate.

rRNA is particularly useful for detecting and/or typing pathogenic bacteria. Examples of such bacteria include chlamydia, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, Lymes disease bacteria, streptococci, or *neisseria*.

Small RNA can also be sequenced. For example, small RNAs (about 17-27 nt), such as microRNA (miRNA), small or short interfering RNAs (siRNA), short hairpin RNAs (shRNA), and small nuclear RNAs.

EXAMPLES

Example 1

Generation of a Closed Template for Sequencing from a Target Nucleic Acid

This example describes the preparation of a closed template for sequencing from a target nucleic acid selected by the user. For example, DNA or RNA from human, animal, plant, viral, bacterial, fungal or viral sources can be used. For purposes of describing this example (and not meant as a limitation), human genomic DNA (hgDNA) is used. For further purposes of example, PCR is used to amplify a targeted region of the hgDNA. Other amplification methods can be used, and a procedure without amplification can also be utilized.

First, hgDNA is isolated from whole blood (or other source) by any conventional method (e.g., QIAamp DNA Mini kit from Qiagen). Next, an aliquot of the DNA is amplified using PCR. The primers each include a 5' region and a cushion region that do not hybridize with the target nucleic acid. The primers also each include a 3' region that hybridizes with the target nucleic acid. Thus, the pair of primers are configured as follows: (SEQ ID NO:3, first primer) 5'-GGGCCGTTTCCCGGTCTT-AAAAAA-NNN...NNN-3', wherein underlined residues 1-18 are the 5' region, double underlined residues 19-24 are the cushion region, and residues depicted as "NNN...NNN" are the 3' region (complementary to a sequence in the target region of interest); and (SEQ ID NO:4, second primer) 5'-TGGTTGTGTCCGCATCTG-AAAAAA-XXX...XXX-3', wherein underlined residues 1-18 are the 5' region, double underlined residues 19-24 are the cushion region, and residues depicted as "XXX...XXX" are the 3' region (complementary to another sequence in the target region of interest). In this example, the 5' residue of both the first and second primers has a 5'-phosphate.

The PCR reaction is performed generally as follows: Approximately 200 ng of the target nucleic acid, the first and second primers described above (SEQ ID NOs:3 and 4) and a PCR reaction mixture (including e.g., buffer, dNTPs, magnesium, and DNA polymerase) are combined in the well of a microtiter plate in a volume of, for example, 50 microliters. After brief mixing, the microtiter plate is placed in a thermocycler and amplification is conducted using an initial denaturation step at 95° C. followed by 30-40 thermal cycles. The PCR product (amplicon) is then purified using any conventional method (e.g., QIAquick PCR Purification Kit).

An aliquot of the purified PCR amplicon is then subjected to conditions for generating overhangs. Approximately 1 microgram of the amplicon is combined with T4 DNA Polymerase, dTTP and the appropriate buffer. The mixture is then incubated at 25° C. for 10 minutes. The T4 DNA Polymerase is then deactivated by heating the reaction mixture at 70° C. for 10 minutes.

Adaptors are hybridized to the overhang products described above. The adaptor sequences each contain a 5' region that is the complement of the sequence of the 5' region of the first or second primers described above (SEQ ID NO's:3 and 4) and a 3' region that comprises a stem/loop structure. The stem/loop structures of the 2 adaptors can be the same or different. Furthermore, if additional target regions are amplified in the same reaction using additional primer pairs (i.e., multiplex amplification), the stem/loop structures used to create closed templates for those regions can be the same or different than those used in the first region. If different, they are used to uniquely identify each sequence in the multiplex reaction (i.e., bar coding). The pair of adaptors used in this example are configured as follows: (SEQ ID NO:5 first adaptor) 5'-AAGACCGGGAAACGGCCC-ATCTCTCTC-TTTTCCTCCTCCTCCGTTGTTGTTGTT-GAGAGAGAT-3', wherein underlined residues are the 5' region, double underlined residues are the stem regions of the adaptor, and the non-underlined residues are the loop region of the adaptor; and (SEQ ID NO:6 second adaptor) 5'-CAGATGCGGACACAACCA-ATCTCTCTC-TTTTCCTCCTCCTCCGTTGTTGTTGTT-GAGAGAGAT-3', wherein underlined residues are the 5' region, double underlined residues are the stem regions of the adaptor, and the non-underlined residues are the loop region of the adaptor. In this example, the 5' residues of both the first and second adaptors have a 5'-phosphate. An approximately 2-fold molar excess of each adaptor over the PCR amplicon is added to the reaction mix described above for creation of overhangs. The mixture is incubated at 25° C. for 15 minutes.

Ligation to close the templates created as described above is performed by adding T4 DNA Ligase to the above reaction mix. The mixture is then incubated at 25° C. for 30 minutes, followed by incubation at 70° C. for 10 minutes to inactivate the enzyme.

Excess adaptors and template that failed to completely ligate are removed by treating the reaction mixture with Exonucleases III and VII for 1 hour at 37° C. Closed template is then purified by an appropriate method (e.g., AMPureXP® kit). Purified templates are quantitated if necessary using a Qubit fluorometer. Further analysis is performed using gel electrophoresis, such as with a 1.2% E-gel.

Closed template is then prepared for a sequencing reaction on a Pacific Biosciences RS sequencer. Briefly, closed template is annealed with the sequencing primer and polymerase provided in the DNA Polymerase Binding Reagent Kit 8 according to manufacturer instructions. Closed template with bound sequencing primer and polymerase are then be loaded into SMRTcells and a sequencing reaction is performed on an RS sequencing instrument.

Example 2

Generation of a Closed Template for Sequencing from a Target Nucleic Acid, Shorter Protocol The materials and protocols for this example are the same as Example 1 above through the step of generating overhangs. At that point the protocol changes in that some of the steps are combined.

After generation of the overhangs using T4 Polymerase and inactivation of the enzyme via incubation at 70° C. for 10 minutes, an approximate 2-fold molar excess over the PCR amplicon of the first (SEQ ID NO:5) and second (SEQ ID NO:6) adaptors as well as T4 DNA Ligase are added to the reaction mixture. The mixture is then incubated at 25° C. for 30 minutes.

Excess adaptors and template that failed to completely ligate are removed by treating the reaction mixture with Exonucleases III and VII for 1 hour at 37° C. Closed template is then purified by a conventional method (e.g., AMPureXP® kit). Purified templates are quantitated if necessary using a Qubit fluorometer. Further analysis is performed using gel electrophoresis, such as with a 1.2% E-gel.

Closed template is then prepared for a sequencing reaction on a Pacific Biosciences RS sequencer. Briefly, closed template is annealed with the sequencing primer and polymerase provided in the DNA Polymerase Binding Reagent Kit 8 according to manufacturer instructions. Closed template with bound sequencing primer and polymerase is then loaded into SMRTcells and a sequencing reaction is performed on an RS sequencing instrument.

Example 3

Generation of a Closed Nucleic Acid Structure from a Target Nucleic Acid

This example describes the preparation of a closed nucleic acid structure from a target nucleic acid according to Method 21. A 765 bp amplicon of the 5' LTR region of HIV was amplified from a plasmid by PCR. The PCR used 5' phosphorylated primers targeting the plasmid sequence at flanking ends of the inserted 5' LTR sequence (SEQ ID NOs:7 & 8). The amplification reaction mixture was generated using Phusion® High-Fidelity DNA Polymerase kit (New England Biolabs, U.S.A., Cat# M0530L) according to manufacturer's instructions. Following amplification the resulting amplicon was purified using a QIAquick PCR Purification kit (Qiagen, U.S.A., Cat# 28106). An aliquot containing 5 micrograms of the purified amplicon was combined with two 3' blocked oligonucleotides having 3' segments identical to the PCR primers used in the initial amplification step except that a reverse polarity C was added to the 3'-end of each primer (reverse polarity phosphoramadites are available from Biosearch Technologies, Inc., U.S.A., Cat# BG1-1100I-1), and further having 5' segments that were an additional 6 nucleotides in length [SEQ ID NO:9 (5'-TAATCCGTAAAACGACGGCCAGT-3-3'-C-5') and SEQ ID NO:10 (5'-TAATCCGGAAACAGCTATGACCATG-3'-3'-C-5')]. The 5' segment of each primer served as a template for extension of the 3' ends of each of the two strands from the purified amplicon. An extension reaction was performed using Taq polymerase (Go-Taq hotstart DNA polymerase, Promega, U.S.A., part #M5005) under the following conditions: 2 minutes at 95° C. for initial denaturation and enzyme activation, 1 minute at 50° C. for annealing and 30 second at 72° C. for extension. The extended template was then purified using the QIAquick PCR Purification Kit.

Figure 23:
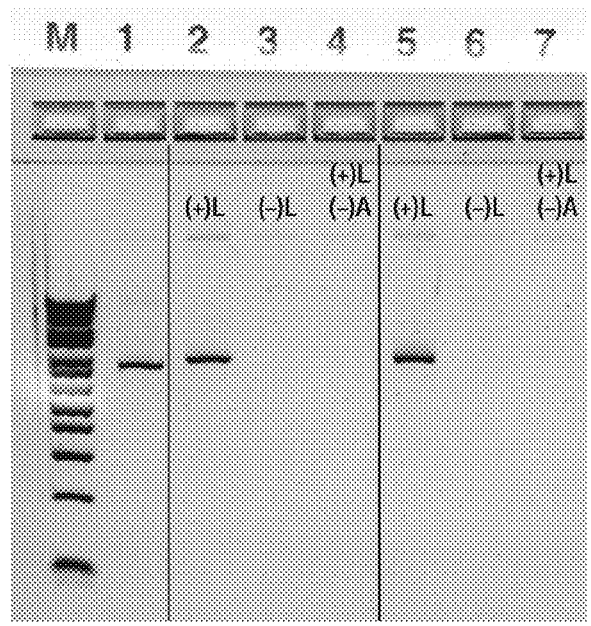
FIG. 23 depicts results obtained from Method 21, as described in Example 3, and is an image of an agarose gel showing closed nucleic acid structures obtained under different conditions, including +/−ligase and +/−stem-loop adaptor.

An aliquot containing 0.5 micrograms of this second amplification product was then combined with a 2-3 fold molar excess of a 5' phosphorylated stem-loop adapter equipped on its 3'-end with the same 6 nucleotide sequence tag in the 3-blocked oligonucleotides used in the second round PCR (SEQ ID NO:11: (5'-TCTCTCTCTTTTCCTC-CTCCTCCGTTGTTGTTGTTGAGAGAGATAATCC-3') (SEQ ID NO:11) and 600 U T4 DNA Ligase (New England Biolabs, Cat# M0202). The reaction mixture was incubated at 25° C. for 30 minutes, followed by an enzyme inactivation step for 10 minutes at 70° C. To remove non-ligated material, the reaction mixture was then treated with 5 U Lambda Exonuclease (New England Biolabs, U.S.A., part # M0262), 100 U of Exonuclease III (New England Biolabs, U.S.A., Cat#M0206S) and 5 U Exonuclease VII (USB Affymetrix, U.S.A., Cat# 70082Z) at 37° C. for 30 minutes, followed by an enzyme inactivation step for 10 minutes at 70° C. The closed nucleic acids were purified using MinElute columns (Qiagen, U.S.A., Cat # 28006) and visualized on a 2% E-gel (Life Technologies, U.S.A., Cat#G402002). The bands indicated by the arrows in FIG. 23 represent the closed nucleic acid both before and after nuclease treatment. The contents of the lanes shown in FIG. 23 are as follows:

Left Gel
M. 100 bp size ladder (E-gel 1 Kb Plus)
1. Amplified template (765 bp)
2. Extended template
3. Extended template+adaptor+Ligase; before exonuclease treatment
4. Extended template+adaptor; before exonuclease treatment
5. Extended template+Ligase; before exonuclease treatment Right Gel
M. 100 bp size ladder (E-gel 1 Kb Plus)
1. Amplified template (765 bp)
2. Extended template
3. Extended template+adaptor+Ligase; after exonuclease treatment
4. Extended template+adaptor; after exonuclease treatment
5. Extended template+Ligase; after exonuclease treatment The results clearly demonstrate formation of a closed nucleic acid structure using the method described herein.

Example 4

Exemplary Nucleic Acid Sequences

The instant example provides exemplary sequences that are useful with the present invention. This table does not limit the scope of the invention. Sequences are presented according to World Intellectual Property Organization (WIPO) Handbook on Industrial Property Information and Documentation, Standard ST.25 (1998), including Tables 1 through 6 of Appendix 2.

| SEQ ID NO: 33 | | Misc |
|---|---|---|
| 1 | GCGCCG | Exemplary first primer 5' segment sequence that is complementary to a 5' segment sequence in a second primer. |
| 2 | CGGCGC | Exemplary second primer 5' segment sequence that is complementary to a 5' segment sequence in a first primer. |

-continued

| SEQ ID NO: 33 | | Misc |
|---|---|---|
| 3 | GGGCCGTTTCCCGGTCTTAA AAAANNN...NNN | Exemplary first primer used in Example 1. |
| 4 | TGGTTGTGTCCGCATCTGAA AAAAXXX...XXX | Exemplary second primer used in Example 1. |
| 5 | AAGACCGGGAAACGGCCCA TCTCTCTCTTTTCCTCCTCCT CCGTTGTTGTTGTTGAGAGA GAT | Exemplary first adaptor used in Example 1. |
| 6 | CAGATGCGGACACAACCAA TCTCTCTCTTTTCCTCCTCCT CCGTTGTTGTTGTTGAGAGA GAT | Exemplary second adaptor used in Example 1. |
| 7 | GTAAAACGACGGCCAGT | Forward primer for amplifying HIV 5' LTR from a plasmid, used in Example 3. |
| 8 | GGAAACAGCTATGACCATG | Reverse primer for amplifying HIV 5' LTR from a plasmid, used in Example 3. |
| 12 | TAATCC | Exemplary 5' segment of 3' blocked oligonucleotides used in Example 3. |
| 9 | TAATCCGTAAAACGACGGC CAGT-3-3'-C | 3' blocked oligonucleotide used in Example 3. |
| 10 | TAATCCGGAAACAGCTATG ACCATG-3'-3'-C | 3' blocked oligonucleotide used in Example 3. |

-continued

| SEQ ID NO: 33 | | Misc |
|---|---|---|
| 11 | TCTCTCTCTTTTCCTCCTCC TCCGTTGTTGTTGTTGAGA GAGATAATCC | 5' phosphorylated stem-loop adapter used in Example 3. |

* Sequences in this Table are written 5' to 3' except where indicate by 3'-3'. In these instances, the nucleobases following the 3'-3' are reverse polarity nucleobases.

All patent filings, other publications including websites, accession numbers and the like cited above are incorporated by reference in their entirety for all purposes to the same extent as if each individual item were specifically and individually indicated to be so incorporated by reference. If different variants of a sequence are associated with an accession number at different times, the version associated with the accession number at the effective filing date of this application is meant. Likewise if different versions of any citation occur at different times, the version existing at the effective filing date is meant. Effective filing date means the earlier of the actual filing date or filing date of an earlier application from which priority is claimed disclosing the accession number of other citation. Any feature, step, element, embodiment, or aspect of the invention can be used in combination with any other unless specifically indicated otherwise. Although the present invention has been described in some detail by way of illustration and example for purposes of clarity and understanding, it is apparent that certain changes and modifications may be practiced within the scope of the appended claims.

What is claimed is:

1. A method of forming a closed nucleic acid structure comprising a target nucleic acid, the method comprising:
   (a) providing a denatured target nucleic acid, at least one strand of the denatured target nucleic acid having a 5' phosphate, a 5' segment, and a 3' segment;
   (b) contacting the strand of the denatured target nucleic acid with a 3' blocked oligonucleotide having a 5' segment, a 3' segment, and an intervening segment that links the 5' and 3' segments, the 3' segment being complementary to the 3' end segment of the denatured target nucleic acid strand and the intervening segment having a common sequence with the 5' segment of the denatured target nucleic acid strand;
   (c) annealing the 3' segment of the 3' blocked oligonucleotide to the 3' segment of the denatured target nucleic acid strand, whereby the 3' blocked oligonucleotide provides a template for extension of the denatured target nucleic acid strand;
   (d) extending the denatured target nucleic acid strand to form a 3' extended nucleic acid strand having from 5'-3' a 5' phosphate group, the target nucleic acid strand, a 3' extension complementary to the 5' and intervening segments of the 3' blocked oligonucleotide, and a 3' hydroxyl group;
   (e) separating the 3' blocked oligonucleotide from the 3' extended nucleic acid strand;

(f) contacting the 3' extended nucleic acid with a stem-loop adaptor having a 3' segment and a 5' segment, the 5' segment having a 5' phosphate group and a sequence capable of forming a stem-loop structure and the 3' segment having a common sequence with the 3' segment of the 3' blocked oligonucleotide and ending in a 3' hydroxyl group;

(g) allowing the 3' extended nucleic acid strand to intermolecularly hybridize with the stem-loop adaptor and intramolecularly hybridize with itself; thereby forming a nicked intermediate wherein the 3' extended nucleic acid strand has a stem-loop structure, the 5' phosphate group of the 3' extended nucleic acid strand is separated from the 3' hydroxyl group of the stem-loop adaptor by a nick, and the 5' phosphate group of the stem-loop adaptor is separated from the 3' hydroxyl group of the 3' extended nucleic acid strand by a nick; and (h) providing a ligase that seals nicks between the ends of the stem-loop adaptor and the ends of the 3' extended nucleic acid, thereby forming a closed nucleic acid structure including the strand of the target nucleic acid circularized by a stem-loop structure.

2. The method of claim 1, wherein the 3' blocked oligonucleotide contains deoxyribo-uracil and is separated from the extended target nucleic acid strand by digestion with a uracil DNA glycosidase (UNG) and an endonuclease.

3. The method of claim 1, wherein the 3' blocked oligonucleotide comprises an affinity label.

4. The method of claim 3, wherein the affinity label is biotin.

5. The method of claim 1, wherein the 3' blocked oligonucleotide is linked to a solid support.

6. The method of claim 1, wherein the 3' blocked oligonucleotide is separated from the 3' extended nucleic acid strand by denaturation and purification.

* * * * *